United States Patent
Cohen et al.

(10) Patent No.: US 12,051,509 B2
(45) Date of Patent: Jul. 30, 2024

(54) METHODS AND MACHINE LEARNING SYSTEMS FOR PREDICTING THE LIKELIHOOD OR RISK OF HAVING CANCER

(71) Applicant: 20/20 GeneSystems Inc., Gaithersburg, MD (US)

(72) Inventors: Jonathan Cohen, Rockville, MD (US); Jodd Readick, New York, NY (US); Victoria Doseeva, Rockville, MD (US); Peichang Shi, Rockville, MD (US); Jose Miguel Flores-Fernandez, Edmonton (CA)

(73) Assignee: 20/20 GeneSystems Inc., Gaithersburg, MD (US)

( * ) Notice: Subject to any disclaimer, the term of this patent is extended or adjusted under 35 U.S.C. 154(b) by 0 days.

(21) Appl. No.: 18/130,426

(22) Filed: Apr. 4, 2023

(65) Prior Publication Data

US 2024/0112811 A1 Apr. 4, 2024

Related U.S. Application Data

(63) Continuation of application No. 15/617,899, filed on Jun. 8, 2017, now Pat. No. 11,621,080, which is a
(Continued)

(51) Int. Cl.
*G16H 50/30* (2018.01)
*G16B 40/00* (2019.01)
(Continued)

(52) U.S. Cl.
CPC ............ *G16H 50/30* (2018.01); *G16B 40/00* (2019.02); *G16B 40/20* (2019.02); *G16B 40/30* (2019.02);
(Continued)

(58) Field of Classification Search
CPC ..................................................... G16B 40/00
See application file for complete search history.

(56) References Cited

U.S. PATENT DOCUMENTS

| 5,188,934 A | 2/1993 | Menchen et al. |
| 5,366,860 A | 11/1994 | Bergot et al. |

(Continued)

FOREIGN PATENT DOCUMENTS

| WO | 9745539 A1 | 12/1997 |
| WO | 9921881 A1 | 5/1999 |

(Continued)

OTHER PUBLICATIONS

American Cancer Society, Cancer Facts & Figures 2011, Atlanta, American Cancer Society, 2011.
(Continued)

*Primary Examiner* — Joseph D Burgess
(74) *Attorney, Agent, or Firm* — Koren Anderson

(57) ABSTRACT

Embodiments of the present invention relate generally to non-invasive methods and tests that measure biomarkers (e.g., tumor antigens) and collect clinical parameters from patients, and computer-implemented machine learning methods, apparatuses, systems, and computer-readable media for assessing a likelihood that a patient has a disease, relative to a patient population or a cohort population. In one embodiment, a classifier is generated using a machine learning system based on training data from retrospective data and subset of inputs (e.g. at least two biomarkers and at least one clinical parameter), wherein each input has an associated weight and the classifier meets a predetermined Receiver Operator Characteristic (ROC) statistic, specifying a sensitivity and a specificity, for correct classification of patients. The classifier may then be used to assesses the likelihood that a patient has cancer relative to a population by classify the patient into a category indicative of a (Continued)

likelihood of having cancer or into another category indicative of a likelihood of not having cancer.

16 Claims, 23 Drawing Sheets

Related U.S. Application Data continuation-in-part of application No. PCT/US2015/064344, filed on Dec. 7, 2015.

(60) Provisional application No. 62/089,061, filed on Dec. 8, 2014.

(51) Int. Cl.
| | | |
|---|---|---|
| *G16B 40/20* | (2019.01) | |
| *G16B 40/30* | (2019.01) | |
| *G16B 50/00* | (2019.01) | |
| *G16B 50/30* | (2019.01) | |
| *G16H 10/60* | (2018.01) | |
| *G16H 50/20* | (2018.01) | |
| *G16H 50/70* | (2018.01) | |

(52) U.S. Cl.
CPC ............. *G16B 50/00* (2019.02); *G16B 50/30* (2019.02); *G16H 10/60* (2018.01); *G16H 50/20* (2018.01); *G16H 50/70* (2018.01)

(56) References Cited

U.S. PATENT DOCUMENTS

| | | | |
|---|---|---|---|
| 5,411,876 | A | 5/1995 | Bloch et al. |
| 5,413,924 | A | 5/1995 | Kosak et al. |
| 5,432,272 | A | 7/1995 | Benner |
| 5,538,848 | A | 7/1996 | Livak et al. |
| 5,550,044 | A | 8/1996 | Kosak et al. |
| 5,800,996 | A | 9/1998 | Lee et al. |
| 5,847,162 | A | 12/1998 | Lee et al. |
| 5,863,727 | A | 1/1999 | Lee et al. |
| 5,925,517 | A | 7/1999 | Tyagi et al. |
| 5,936,087 | A | 8/1999 | Benson et al. |
| 5,945,526 | A | 8/1999 | Lee et al. |
| 5,965,364 | A | 10/1999 | Benner |
| 5,985,619 | A | 11/1999 | Sutherland et al. |
| 6,001,983 | A | 12/1999 | Benner |
| 6,008,379 | A | 12/1999 | Benson et al. |
| 6,020,481 | A | 2/2000 | Benson et al. |
| 6,051,719 | A | 4/2000 | Benson et al. |
| 6,103,476 | A | 8/2000 | Tyagi et al. |
| 6,140,054 | A | 10/2000 | Wittwer et al. |
| 6,140,500 | A | 10/2000 | Yan et al. |
| 6,150,097 | A | 11/2000 | Tyagi et al. |
| 6,191,278 | B1 | 2/2001 | Lee et al. |
| 6,329,144 | B1 | 12/2001 | Kubista et al. |
| 6,355,421 | B1 | 3/2002 | Coull et al. |
| 6,383,752 | B1 | 5/2002 | Agrawal et al. |
| 6,403,341 | B1 | 6/2002 | Barnes et al. |
| 6,485,901 | B1 | 11/2002 | Gildea et al. |
| 6,548,250 | B1 | 4/2003 | Sorge |
| 6,589,743 | B2 | 7/2003 | Sorge |
| 6,590,091 | B2 | 7/2003 | Albagli et al. |
| 6,593,091 | B2 | 7/2003 | Keys et al. |
| 6,596,490 | B2 | 7/2003 | Dattagupta |
| 6,649,349 | B2 | 11/2003 | Gildea et al. |
| 7,060,809 | B2 | 6/2006 | Wengel et al. |
| 2006/0078894 | A1 | 4/2006 | Winkler et al. |
| 2007/0178504 | A1 | 8/2007 | Colpitts et al. |
| 2008/0057502 | A1 | 3/2008 | Kopreski |
| 2008/0133141 | A1 | 6/2008 | Frost |
| 2008/0160546 | A1 | 7/2008 | Colpitts et al. |
| 2009/0075258 | A1 | 3/2009 | Latham et al. |
| 2011/0053158 | A1 | 3/2011 | Mambo et al. |
| 2012/0071334 | A1 | 3/2012 | Colpitts et al. |
| 2012/0108462 | A1 | 5/2012 | Keller et al. |
| 2013/0196868 | A1* | 8/2013 | Lebowitz ......... G01N 33/57484 702/19 |
| 2014/0095201 | A1* | 4/2014 | Farooq ................... G16H 50/30 705/3 |

FOREIGN PATENT DOCUMENTS

| | | | |
|---|---|---|---|
| WO | 1999021881 | A1 | 5/1999 |
| WO | 2009006323 | A2 | 1/2009 |

OTHER PUBLICATIONS

Bach, P.B., et al, Screening for Lung Cancer: ACCP Evidence-Based clinical Practice Guidelines (2nd Edition), Chest, 2007;132(Suppl 3):69S-77S.

Bach, PB, et al., Benefits and harms of CT screening for lung cancer: a systematic review, JAMA, 2012;307(22):2418-29.

Bianchi, F., et al., A serum circulating miRNA diagnostic test to identify asymptomatic high-risk individuals with early stage lung cancer, EMBO Molecular Medicine, 2011;3(8):495-503.

Bigbee, W.L.P., et al., A multiplexed serum biomarker immunoassay panel discriminates clinical lung cancer patients from high-risk individuals found to be cancer-free by CT screening, Journal of Thoracic Oncology, Apr. 2012;7(4):698-708.

Callister, ME, et al., British Thoracic Society guidelines for the investigation and management of pulmonary nodules, Thorax, 2015;70(Suppl 2):ii1-1154.

Chen, C., et al., Real-time quantification of microRNAs by stem-loop RT-PCR, Nucleic Acids Research, 2005;33(20):e179.

Chen, X., et al., Identification of ten serum microRNAs from a genome-wide serum microRNA expression profile as novel noninvasive biomarkers for non-small cell lung cancer diagnosis, International Journal of Cancer, 2012;130(7):1620-1628.

Croswell, JM, et al., Cumulative incidence of false-positive results in repeated, multimodal cancer screening. Annals of Family Med, 2009;7(3):212-22.

Devos, T., et al., Circulating Methylated SEPT9 DNA in Plasma is a biomarkers for colorectal cancer, Clinical Chemistry, 2009;55(7):1337-1346.

Farlow, E., et al., Development of multiplexed tumor-associated autoantibody-based blood test for the detection of non-small cell lung cancer, Clinical Cancer Research, Jun. 22, 2010;16(13):3452-3462.

Feng et al., The Effect of Artificial Neural Network model Combined with Six Tumor Markers in Auxiliary Diagnosis of Lung Cancer, J Med Syst, 2012;36(5):2973-2980.

Gould, MK, et al., Evaluation of individuals with pulmonary nodules: when is it lung cancer? Diagnosis and management of lung cancer, 3rd ed: American College of Chest Physicians evidence-based clinical practice guidelines, Chest, 2013;143(5 Suppl):e93S-e120S.

Greenberg, AK, et al, Biomarkers for lung cancer: Clinical Uses, Curr Opin Pulm Med, 2007;13(4):249-55.

Greenhalgh, T., Evidence based medicine: a movement in crisis?, BMJ, 2014;348:g3725.

Guergova-Kuras, M., et al., Discovery of lung cancer biomarkers by profiling the plasma proteome with monoclonal antibody libraries, Molecular & Cellular Proteomics, 2011;10(12):M111.010298.

Hennessey, P., et al., Serum microRNA biomarkers for detection of non-small cell lung cancer, PLoS One, Feb. 2012;7(2):e32307 (6 pages).

Higgins, G., et al., Variant Ciz1 is a circulating biomarker for early-stage lung cancer, PNAS, Nov. 6, 2012;109(45):E3128-E3135.

International Search Report, PCT/US15/64344, issued Jun. 14, 2016.

Izbicka, E., et al., Plasma biomarkers distinguish non-small cell lung cancer from asthma and differ in men and women, Cancer Genomics & Proteomics, 2012;9(1):27-35.

(56) References Cited

OTHER PUBLICATIONS

Lam, S., et al., EarlyCDT-lung: An immunobiomarker test as an early aid to early detection of lung cancer, Cancer Prevention Research, 2011;4(7):1126-1134.

Menon, U., et al., Risk Algorithm Using Serial Biomarker Measurements Doubles the number of Screen-Detected Cancers Compared With a Single-Threshold Rule in the United Kingdom Collaborative Trial of Ovarian Cancer Screening, J Clin Oncol, 2015;33(18):2062-71.

Molina et al., Assessment of a Combined Panel of Six Serum Marker for Lung Cancer; Am J Repir Crit Care Med, Feb. 15, 2016;193(4):427-437.

Molina et al., Tumor Markers in Patients with Non-Small Cell Lung Cancer as an Aid in Histological Diagnosis and Prognosis, Tumor Biol, 2003;24(4):209-218.

Mor, G., et al., Serum protein markers for early detection of ovarian cancer, PNAS, May 24, 2005; 102(21):7977-7982.

National Lung Screening Trial Research Team, et al., Reduced Lung-cancer mortality with low dose computed tomographic screening, N Engl J Med, Aug. 4, 2011;365(5):395-409.

Ostroff, R.M., et al., Unlocking biomarker discovery: large scale applicaiton of aptamer proteomic technology for early detection of lung cancer, PLoS ONE, Dec. 2010;5(12):E15003 (10 pages).

Patnaik, S.K., et al., MicroRNA Expression Profiles of Whole Blood in Lung Adenocarcinoma, PLoS ONE, 2012;7(9):e46045.

Patz, E.F., et al., Panel of serum biomarkers for the diagnosis of lung cancer, Journal of Clinical Oncology, 2007;25(35):5578-5583.

Pine, S.R., et al., Increased levels of circulating interleukin 6, interleukin 8, C-reactive protein, and risk of lung cancer, Journal of the National Cancer Institute, 2011;103(14):1112-1122.

Schneider, J., Tumor markers in detection of lung cancer, Adv Clin Chem, 2006;42:1-41.

Schouten, et al., Relative quantification of 40 nucleic acid sequences by multiplex ligation-dependent probe amplification, Nucleic Acids Research, 2002;30(12):e57.

Shen, J., et al., Plasma microRNAs as potential biomarkers for non-small-cell lung cancer, Lab Invest, 2011;91(4):579-587.

Shortliffe, Eh, et al., "The public health informatics infrastructure: anticipating its role in cancer", Cancer Causes Control, Sep. 2006;17(7):861-9.

Siemes, C., et al., C-reactive protein levels, variation in the C-reactive protein gene, and cancer risk: the Rotterdam Study, J Clin Oncol, 2006;24(33):5216-5222.

Sturgeon, CM, et al., National Academy of Clinical Biochemistry laboratory medicine practice guidelines for use of tumor markers in testicular, prostate, colorectal, breast, and ovarian cancers, Clin Chem, 2008;54(12):e11-e79.

Wen, Y.-H et al., "Cancer screening through a multi-analyte serum biomarker panel during health check-up examinations: results from a 12-year experience", Clinica Chimica Acta, 2015;450:273-276.

Wood, De, et al., Lung cancer screening. J Natl Cancer Compr Netw, 2012;10(2):240-265.

\* cited by examiner

| Aggregate MoM Values "Master Composite Score" | Risk Identifier | Increased Likelihood of Having Lung Cancer "Risk Score" |
|---|---|---|
| >20 | Highest | 13.4x |
| 15-20 | Intermediate High Risk | 5x |
| 10-14 | Intermediate Risk | 2.1x |
| 7-9 | Intermediate Low Risk | 0.7x |
| <=6 | Low Risk | 0.4x |

FIG. 10

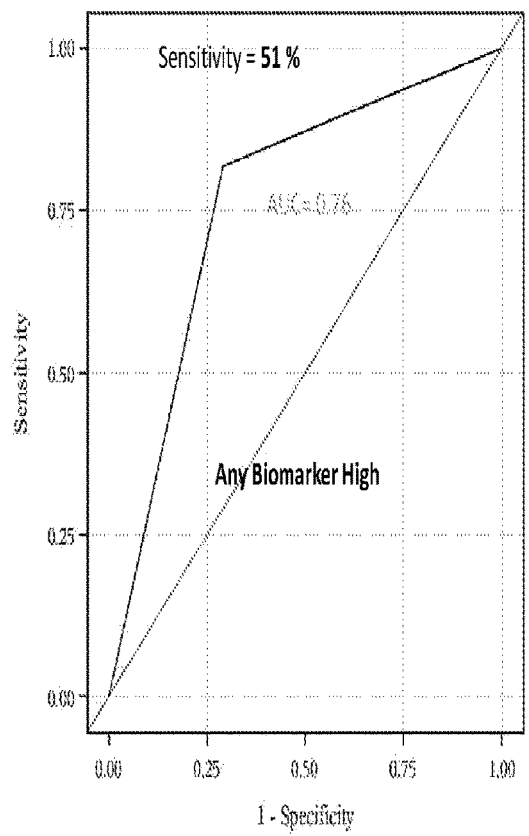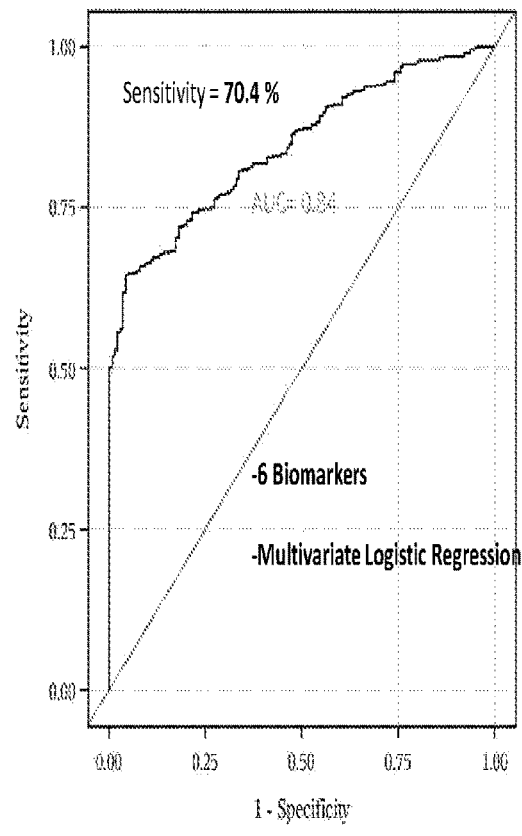
Figure 15A
Figure 15B

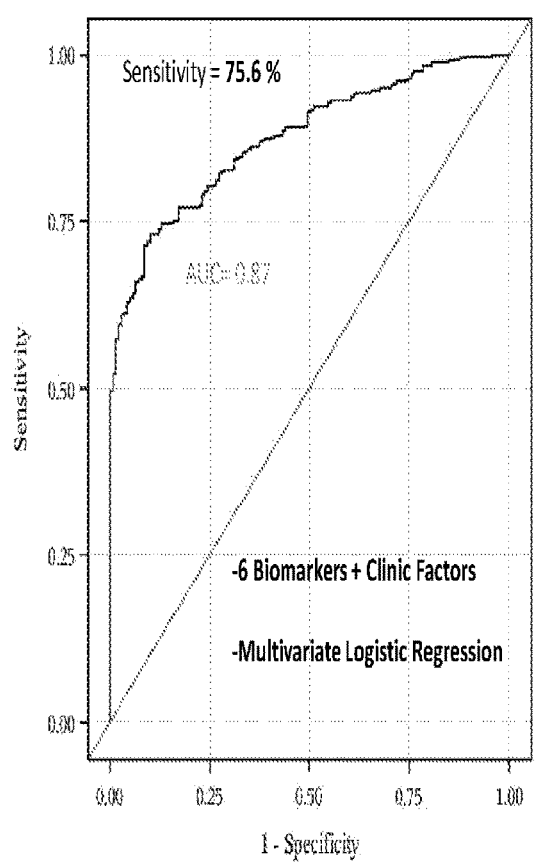
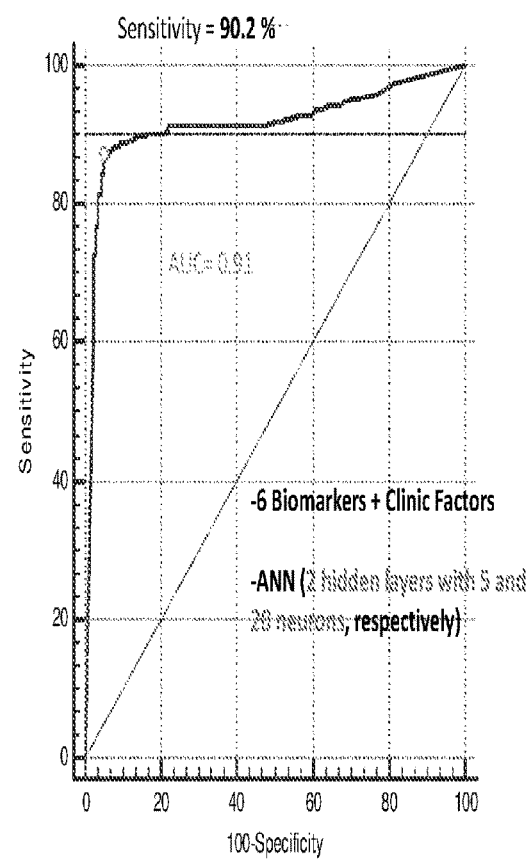
Figure 15C
Figure 15D

METHODS AND MACHINE LEARNING SYSTEMS FOR PREDICTING THE LIKELIHOOD OR RISK OF HAVING CANCER

CROSS-REFERENCE TO RELATED APPLICATION

This application is a continuation-in-part of PCT/US15/64344 filed 7 Dec. 2015, which claims the benefit of U.S. Provisional Patent Application No. 62/089,061, filed 8 Dec. 2014, the contents of which are each incorporated herein by reference in their entirety.

TECHNICAL FIELD

Present invention embodiments relate generally to using an artificial intelligence/machine learning system for analyzing data and making predictions based upon the data, and more specifically, to predicting the likelihood or risk for having a disease such as cancer, especially in an otherwise asymptomatic or vaguely symptomatic patient.

BACKGROUND

Early Detection of Cancer

For many types of cancers, patient outcomes improve significantly if surgery and other therapeutic interventions commence before the tumor has metastasized. Accordingly, imaging and diagnostic tests have been introduced into medical practice in an attempt to help physicians detect cancer early. These include various imaging modalities such as mammography as well as diagnostic tests to identify cancer specific "biomarkers" in the blood and other bodily fluids such as the prostate specific antigen (PSA) test. The value of many of these tests is often questioned particularly with regard to whether the costs and risks associated with false positives, false negatives, etc. outweigh the potential benefits in terms of actual lives saved. Furthermore, in order to demonstrate this value, data from large numbers of patients-many thousands or even tens of thousands—must be generated in real world (prospective) studies rather laboratory stored (retrospective) studies. Unfortunately, the costs of conducting large prospective studies for screening tools is outweighed by reasonably anticipated financial returns so these large prospective studies are almost never done by the private sector and are only occasionally sponsored by governments. As a result, the use paradigms for blood testing for the early detection of most cancers has progressed little in several decades. In the United States, for example, PSA remains the only widely utilized blood test for cancer screening and even its utilization has become controversial. It other parts of the world, especially the Far East, blood tests for detecting various cancers is more commonplace but there is little standardization or empirical methods to ascertain or improve the accuracy of such testing in those parts of the world.

It would therefore be desirable to improve the accuracy and standardization of cancer screening in those regions where it is common and, in so doing, generate tools and technologies that may improve and/or encourage cancer screening in those regions where it is less common.

Cancer detection poses significant technical challenges as compared to detecting viral or bacterial infections since cancer cells, unlike viruses and bacteria, are biologically similar to and hard to distinguish from normal, healthy cells. For this reason, tests used for the early detection of cancer often suffer from higher numbers of false positives and false negatives than comparable tests for viral or bacterial infections or for tests that measure genetic, enzymatic, or hormonal abnormalities. This often causes confusion among healthcare practitioners and their patients leading in some cases to unnecessary, expensive, and invasive follow-up testing while in other cases to a complete disregard for follow-up testing resulting in cancers being detected too late for useful intervention. Physicians and patients welcome tests that yield a binary decision or result, e.g., either the patient is positive or negative for a condition, such as observed in the over the counter pregnancy test kits which present, for example, an immunoassay result in the shape of a plus sign or a negative sign as an indication of pregnancy or not. However, unless the sensitivity and specificity of diagnosis approaches 99%, a level not obtainable for most cancer tests, such binary outputs can be highly misleading or inaccurate.

It would therefore be desirable to provide healthcare practitioners and their patients with more quantitative information about their likelihood of having a particular cancer, even if a binary output is not practical.

Detecting early stage cancer is also challenging due to factors associated with the modern day practice of medicine. Primary care providers in particular typically see a high volume of patients per day and the demands of healthcare cost containment has dramatically shortened the amount of time they can spend with each patient. Accordingly, physicians often lack sufficient time to take in depth family and lifestyle histories, to counsel patients on healthy lifestyles, or to follow-up with patients who have been recommended testing beyond that which is provided in their office practice.

It would therefore be desirable to provide high-volume primary care providers, in particular, with useful tools to help them triage or compare the relative risks for their patients of having cancer so they can order additional testing for those patients at the highest risks.

Lung Cancer and Early Detection

Lung cancer is by far the leading cause of cancer deaths in North America and in most of the world killing more people than the next three most lethal cancers combined, namely breast, prostate, and colorectal cancer. Lung cancer results in over 156,000 deaths per year in the United States alone (American Cancer Society. Cancer Facts & FIGS. 2011. Atlanta: American Cancer Society; 2011). Tobacco use has been identified as a primary causal factor for lung cancer and is thought to account for some 90% of cases. Thus, individuals over 50 years of age with a smoking history of greater than 20 pack-years have a 1 in 7 lifetime risk of developing the disease. Lung cancer is a relatively silent disease displaying few if any specific symptoms until it reaches the later more advanced stages. Therefore, most patients are not diagnosed until after their cancer has metastasized beyond the lung and the cancer is no longer treatable by surgery alone. Thus, while the best way to prevent lung cancer is likely tobacco avoidance or cessation, for many current and former smokers, the transforming, cancer-causing event has already occurred and even though the cancer is not yet manifest, the damage has already been done. Thus, perhaps the most effective means of reducing lung cancer mortality is early stage detection when the tumor is still localized and amenable to surgery with intent to cure.

The importance of early detection was recently demonstrated in a large 7-year clinical study, the National Lung Cancer Screening Trial (NLST), which compared chest x-ray and chest computed topography (CT) scanning as potential modalities for the early detection of lung cancer (National Lung Screening Trial Research Team, Aberle D. R., Adams A. M., Berg C. D., Black W. C., Clapp J. D., Fagerstrom R. M., Gareen I. F., Gatsonis C., Marcus P. M., Sicks J. D. *Reduced lung-cancer mortality with low-dose computed tomographic screening.* N. Engl. J. Med. 2011 Aug. 4; 365(5):395-409). The trial concluded that the use of chest CT scans to screen the at-risk population identified significantly more early stage lung cancers than chest x-rays and resulted in a 20% overall reduction in disease mortality. This study has clearly indicated that identifying lung cancer early can save lives. Unfortunately, the broad application of CT scanning as a screening method for lung cancer is problematic. The NLST design utilized a serial CT screening paradigm in which patients received a CT scan annually for only three years. Nearly 40% of the participants receiving the annual CT scan over 3 years had at least one positive screening result and 96.4% of these positive screening results were false positives. This very high rate of false positives can cause patient anxiety and place a burden on the healthcare system, as the work-up following a positive finding on low-dose CT scans often includes advanced imaging and biopsies. Although CT scanning is an important tool for the early detection of lung cancer, more than two years after the NLST results were announced, very few patients at high risk for lung cancer due to smoking history have initiated a program of annual CT scans. This reluctance to undergo yearly CT scans is likely due to a number of factors including costs, perceived risks of radiation exposure, especially by serial CT scans, the inconvenience or burden to asymptomatic patients of scheduling a separate diagnostics procedure at a radiology center, as well as concerns by physicians that the very high false positive rates of CT scanning as a standalone test will result in a significant number of unnecessary follow up diagnostic tests and invasive procedures.

While the overall lifetime risk for lung cancer amongst smokers is high, the chance that any individual smoker has cancer at a specific point in time is on the order of 1.5-2.7% [Bach, P. B., et al., Screening for Lung Cancer*ACCP Evidence-Based Clinical Practice Guidelines (2nd Edition). CHEST Journal, 2007. 132(3_suppl): p. 69S-77S.]. Due to this low disease prevalence, identifying which patients are at highest risk is challenging and complex.

It would be desirable to have blood tests to compliment use of radiographic screening for the early detection of lung cancer.

Artificial Intelligence/Machine Learning Systems

Artificial intelligence/machine learning systems are useful for analyzing information, and may assist human experts in decision making. For example, machine learning systems comprising diagnostic decision-support systems may use clinical decision formulas, rules, trees, or other processes for assisting a physician with making a diagnosis.

Although decision-making systems have been developed, such systems are not widely used in medical practice because these systems suffer from limitations that prevent them from being integrated into the day-to-day operations of health organizations. For example, decision-making systems may provide an unmanageable volume of data, rely on analysis that is marginally significant, and not correlate well with complex multimorbidity (Greenhalgh, T. Evidence based medicine: a movement in crisis? *BMJ* (2014) 348: g3725)

Many different healthcare workers may see a patient, and patient data may be scattered across different computer systems in both structured and unstructured form. Also, the systems are difficult to interact with (Berner, 2006; Shortliffe, 2006). The entry of patient data is difficult, the list of diagnostic suggestions may be too long, and the reasoning behind diagnostic suggestions is not always transparent. Further, the systems are not focused enough on next actions, and do not help the clinician figure out what to do to help the patient (Shortliffe, 2006).

It would, therefore, be desirable to provide methods and technologies to permit artificial intelligence/machine learning systems to be used to aid in the early detection of cancer, especially with blood testing.

SUMMARY

Embodiments of the present invention relate generally to non-invasive methods, diagnostic tests, especially blood (including serum or plasma) tests that measure biomarkers (e.g. tumor antigens), and computer-implemented machine learning methods, apparatuses, systems, and computer-readable media for assessing a likelihood that a patient has a disease, such as cancer, relative to a patient population or a cohort population to determine whether that patient should be followed up with additional, more invasive testing.

In embodiments are provided a computer implemented method for predicting a likelihood of having cancer in a patient, in a computer system having one or more processors coupled to a memory storing one or more computer readable instructions for execution by the one or more processors, the one or more computer readable instructions comprising instructions for: storing a set of data comprising a plurality of patient records, each patient record including a plurality of parameters and corresponding values for a patient, and wherein the set of data also includes a diagnostic indicator indicating whether or not the patient has been diagnosed with cancer. In embodiments, the patient records are retrospective data which includes both a diagnosis and patient data such as measured biomarkers and clinical parameters. The computer implemented methods comprises selecting a subset of the plurality of parameters for inputs into a machine learning system, wherein the subset includes a panel of at least two different biomarkers and at least one clinical parameter; randomly partitioning the set of data into training data and validation data; generating a classifier using a machine learning system based on the training data and the subset of inputs, wherein each input has an associated weight; and determining whether the classifier meets a predetermined Receiver Operator Characteristic (ROC) statistic, specifying a sensitivity and a specificity, for correct classification of patients.

In embodiments, the predetermined ROC statistic is a sensitivity of at least 70% with at least an 80% specificity. In certain embodiments, the sensitivity, with an 80% specificity, is at least 75%, 80%, 82%, 85%, 87%, 90%, 91%, 92%, 93%, 94%, 95%, 96%, 97% or 98%. In other embodiments, the sensitivity, with an 85% specificity, is at least 70%, 75%, 80%, 82%, 85%, 87%, 90%, 91%, 92%, 93%, 94%, 95%, 96%, 97% or 98%. In embodiments, the sensitivity, with an 90% specificity, is at least 70%, 75%, 80%, 82%, 85%, 87%, 90%, 91%, 92%, 93%, 94%, 95%, 96%, 97% or 98%.

In embodiments, the computer implemented method further comprises iteratively regenerating the classifier when the classifier does not meet the predetermined ROC statistic, by using a different subset of inputs and/or by adjusting the associated weights of the inputs until the regenerated classifier meets the predetermined ROC statistic. In certain embodiments, the computer implemented method further comprises generating a static configuration of the classifier when the machine learning system meets the predetermined ROC statistic. The classifier may be used, for example by a physician, when the classifier is static, semi-static (e.g. the classifier may be updated at designated intervals) or dynamic (e.g. the classifier is updated as additional data for a patient is inputted into the system included as a diagnosis). Typically, a diagnosis for the presence of cancer is confirmed with radiographic screening and/or by histology of a biopsy sample.

In embodiments, the method comprises classifying the validation data using the classifier; determining whether the classifier meets the predetermined ROC statistic; and when the classifier does not meet the predetermined ROC statistic, iteratively regenerating the classifier by using a different subset of inputs and/or by adjusting the associated weights of the inputs, until the regenerated classifier meets the predetermined ROC statistic. In embodiments, the method further comprising configuring a computing device accessible by a user with the static classifier; entering values for the subset of the plurality of parameters corresponding to a patient into the computing device; and classifying, using the static classifier, the patient into a category indicative of a likelihood of having cancer or into another category indicative of a likelihood of not having cancer.

In embodiments, the category indicative of a likelihood of having cancer is further categorized into qualitative groups such as low, medium, high, or some combination or subcombination thereof. In alternative embodiments, the category indicative of a likelihood of having cancer is further categorized into quantitative groups. Those quantitative groups may be provided to the user as a percentage, multiplier value, composite score or risk score for the likelihood of having cancer or an increased risk of having cancer. In certain embodiments, the methods further comprise providing a notification to the user recommending diagnostic testing when the patient is classified into the category indicative of a likelihood of having cancer. In embodiments, the diagnostic testing is radiographic screening or analysis of a biopsy sample.

In embodiments, wherein the classifier is updated, the method further comprises obtaining test results from the diagnostic testing which confirm or deny the presence of cancer, incorporating the test results into the training data for further training of the machine learning system; and generating an improved classifier by the machine learning system.

In embodiments, the biomarkers may be any two, any three, any four, any five, or any six or more biomarkers associated with the presence of cancer. In embodiments, the panel of biomarkers is selected from the group consisting of: AFP, CA125, CA 15-3, CA 19-19, CEA, CYFRA 21-1, HE-4, NSE, Pro-GRP, PSA, SCC, anti-Cyclin E2, anti-MAPKAPK3, anti-NY-ESO-1, and anti-p53. In embodiments, a sample is obtained from a patent for measurement of biomarkers wherein the sample is sample is blood, blood serum, blood plasma, or a component thereof. In embodiments, the clinical parameters may be one or more of age; gender; smoking status (e.g. lung cancer); number of pack years; symptoms; family history of cancer; concomitant illnesses; number of nodules (e.g. pulmonary nodules); size of nodules; and imaging data. See Example 4 for a ranking of biomarkers and clinical factors for lung cancer. In embodiments, clinical parameters for lung cancer include smoking status, pack years, and age. In certain embodiments, clinical parameters for lung cancer include an age of at least 50; and at least a 20 pack year smoking history.

In embodiments, the classifier is a support vector machine, a decision tree, a random forest, a neural network, or a deep learning neural network. In certain embodiments, the classifier is a neural net that has any one or more of the following features: at least two hidden layers; at least two outputs, with a first output indicating that lung cancer is likely and a second output indicating that lung cancer is not likely; and 20-30 nodes. See Example 3 for training of a neural net with retrospective patient data with lung cancer.

In embodiments, the cancer is selected from the group consisting of: breast cancer, bile duct cancer, bone cancer, cervical cancer, colon cancer, colorectal cancer, gallbladder cancer, kidney cancer, liver or hepatocellular cancer, lobular carcinoma, lung cancer, melanoma, ovarian cancer, pancreatic cancer, prostate cancer, skin cancer, and testicular cancer. In illustrative embodiments, the cancer is lung cancer.

In embodiments, a computer implemented method for predicting a likelihood of cancer in a subject is provided using a computer system having one or more processors coupled to a memory storing one or more computer readable instructions for execution by the one or more processors, the one or more computer readable instructions comprising instructions for: storing a set of data comprising a plurality of patient records, each patient record including a plurality of parameters for a patient, and wherein the set of data also includes a diagnostic indicator indicating whether or not the patient has been diagnosed with cancer; selecting a plurality of parameters for inputs into a machine learning system, wherein the parameters include a panel of at least two different biomarker values and at least one type of clinical data; and generating a classifier using the machine learning system, wherein the classifier comprises a sensitivity of at least 70% and a specificity of at least 80%, and wherein the classifier is based on a subset of the inputs.

In other embodiments are provided use of the classifier in a method of assessing the likelihood that a patient has lung cancer relative to a population comprising measuring the values of a panel of biomarkers in a sample from a patient and obtaining clinical parameters from the patient; utilizing a classifier generated by a machine learning system to classify the patient into a category indicative of a likelihood of having cancer or into another category indicative of a likelihood of not having cancer, wherein the classifier comprises a sensitivity of at least 70% and a specificity of at least 80%, and wherein the classifier is generated using a panel of biomarkers comprising at least two different biomarkers, and at least one clinical parameter; and when a patient is classified into a category indicating a likelihood of having cancer, providing a notification to a user for diagnostic testing.

In other embodiments, techniques are provided for the use of artificial intelligence/machine learning systems that can incorporate and analyze structured and preferably also unstructured data to perform a risk analysis to determine a likelihood for having cancer, initially lung cancer, but also, other types of cancer, including pan-cancer testing (i.e. testing of multiple tumors from a single patient sample). By utilizing algorithms generated from the biomarker levels (e.g. tumor antigens) from large volumes of longitudinal or prospectively collected blood samples (e.g., real world data from one or more regions where blood based tumor biomarker cancer screening is commonplace) together with one or more clinical parameters (e.g. age, smoking history, disease signs or symptoms) a risk level or percentage of that patient having a cancer type is provided. The machine learning system determines a quantifiable risk for the presence of cancer in patients, preferably before they have symptoms or advanced disease, in terms of an increase over the population (e.g., a cohort population). By determining an individual patient's risk relative to the cohort, physicians may recommend further follow-up testing (e.g. radiography) for those patients who are at higher risks relative to the cohort population and also hope to change patient's behavior which may be increasing the risk of cancer.

In another embodiment, in addition to the aforementioned biomarker levels and one more clinical parameters, the biomarker change over time following serial testing—"velocity"—is included in the algorithm.

In yet another embodiment, in addition to the aforementioned biomarker levels and one more clinical parameters, environment and or occupational (workplace) exposure to carcinogens is included in the algorithm.

In yet another embodiment, in addition to the aforementioned biomarker levels and one more clinical parameters, the patient's personal family history of cancer is included in the algorithm.

In yet another embodiment, in addition to the aforementioned biomarker levels and one more clinical parameters, published information from the medical and scientific literature is included in the algorithm as unstructured data.

According to embodiments of the present invention, a machine learning system utilizes a plurality of data sources, determines which types of data from the data sources are most predictive for determining a risk of having cancer, and outputs a likelihood (e.g., in the form of a percentage risk score or a multiplier, etc.) of developing cancer relative to a population or a cohort population. Instead of simply making a determination of the risk of cancer based upon a single marker or multiple biomarkers, wherein the concentrations of the biomarker(s) are evaluated with respect to fixed threshold concentration(s), the machine learning system may also optionally consider a plurality of different types of data including electronic medical records (EMRs), publically available data, biomarkers, biomarker velocities, and other factors associated with the development of cancer to generate the likelihood of having cancer. The risk of the presence of cancer in a given individual may be quantified in terms of an increase over other individuals in the same risk population (e.g., cohort population). Risk relative to a cohort population provides a clear and quantitative way of providing a risk for developing cancer, while avoiding a binary or absolute "yes" or "no" result associated with false positives or negatives. By using more than one neural net in the system to determine which risk factors are the most important (e.g., most predictive), an improved manner of determining which patients are at increased risk of having cancer may be achieved.

Other more specific embodiments of the invention may include a blood test for assessing a likelihood that a patient has lung cancer relative to a population or a cohort population of individuals, e.g., individuals of a similar age range and smoking history. In this example, one or more biomarkers are analyzed from the patient's fluid sample, e.g., a blood sample, which is used, at least in part, to determine a biomarker composite score and a risk score as compared to a cohort population, known to have lung cancer as well as non-cancer and other controls. This permits the patient's risk of having lung cancer to be categorized using identifiers as low, intermediate, high, very high, etc. As sufficient data is generated, the system will calculate a risk percentage, as well as a margin of error. Based on this information, physicians and other healthcare practitioners, patients, and health insurance companies, can better determine which patients are most likely to benefit from follow-up testing, including CT screening. Such a method reduces the costs, anxiety, and radiation exposure associated with having lower risk patients undergo CT scans while helping to ensure that patients at higher risk of having lung cancer undergo CT scanning in hopes of detecting the tumor at an early stage when curative surgery is an option.

According to another specific embodiment of the invention, the aforementioned artificial intelligence/machine learning system may be used to enhance or improve a blood test for the simultaneous detection of multiple tumor types from a single blood or serum sample. Such "pan-cancer" tests are common in the Far East such as the test disclosed by Y. H. Wen, et al. "Cancer screening through a multi-analyte serum biomarker panel during health check-up examinations; Results from a 12-year experience," *Clinica Chimica Acta* 450 (2015) 273-276. As another example, six biomarkers, CEA, CYFRA, SCC, CA 15.3, NSE and Pro-GRP, were identified that were related to the presence of lung cancer [Molina, R. et al. "Assessment of a Combined Panel of Six Serum Tumor Markers for Lung Cancer", Am. J. Respir. Crit. Care Med. (2015)]. The real world, prospective, raw patient data generated in Taiwan that was used to create that published report could be used, for example, to generate an algorithm according to the present invention that would improve testing both in the region or clinical center where the test was run as well as in regions of the world where such screening paradigms are less common (e.g. the United States).

These and other advantages of the techniques presented herein may be better understood by referring to the following description, accompanying drawings and claims. The embodiments presented herein, set out below to enable one to practice an implementation of the invention, are intended to be non-limiting. Those skilled in the art should readily appreciate that the conceptions and specific embodiments disclosed herein may be used as a basis for modifying or designing other methods and systems for carrying out the same purposes of the present invention. Those skilled in the art should also realize that such equivalent assemblies do not depart from the spirit and scope of the invention in its broadest form.

BRIEF DESCRIPTION OF THE FIGURES

The numerous advantages of the present invention may be better understood by those skilled in the art by reference to the accompanying figures in which:

FIG. 10 shows an example of a risk categorization table for a disease such as lung cancer. In this risk categorization table, the inflection point between having a risk greater than the observed risk of smokers of 2% occurs with an aggregate MoM score of above 9. With an aggregate score of 9 or less, that patient has a risk of lung cancer no greater than does any other heavy smoker not yet diagnosed. A MoM score greater than 9 indicates a greater risk of cancer or a higher likelihood of cancer as compared to the smoking population.

FIGS. 15A-D show various receiver operator characteristic (ROC) curves using various statistical and machine learning approaches, in accordance with example embodiments.

DETAILED DESCRIPTION

Figure 1A:
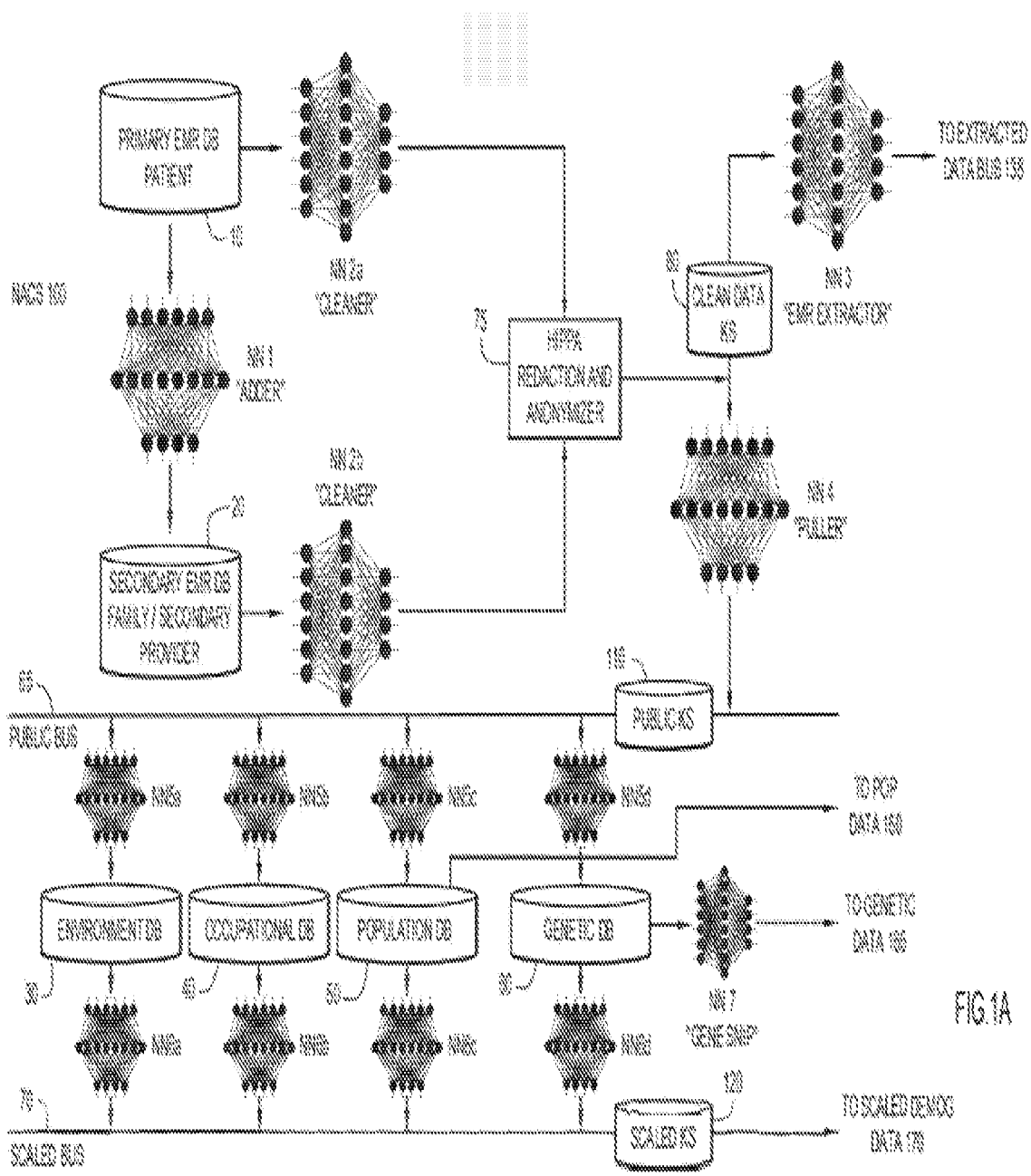
FIGS. 1A-1B are schematic diagrams of an example computing environment in accordance with example embodiments.

Embodiments of the present invention relate generally to non-invasive methods, diagnostic tests, especially blood (including serum or plasma) tests that measure biomarkers (e.g. tumor antigens) in combination with clinical parameters, and computer-implemented machine learning methods, apparatuses, systems, and computer-readable media for assessing a likelihood that a patient has a disease, such as cancer, relative to a patient population or a cohort population to determine whether that patient should be followed up with additional, more invasive testing.

A. Introduction

Embodiments of the present invention provide for non-invasive methods, diagnostic tests, and computer-implemented machine learning methods, apparatuses, systems, and computer-readable media for assessing a likelihood that a patient has a disease, such as cancer, relative to a population or a cohort population by generating, e.g., stratified risk categories to more accurately predict the presence of cancer in an otherwise asymptomatic or vaguely symptomatic patient.

As used herein "machine learning" refers to algorithms that give a computer the ability to learn without being explicitly programmed including algorithms that learn from and make predictions about data. Machine learning algorithms include, but are not limited to, decision tree learning, artificial neural networks (ANN) (also referred to herein as a "neural net"), deep learning neural network, support vector machines, rule base machine learning, random forest, etc. For the purposes of clarity, algorithms such as linear regression or logistic regression can be used as part of a machine learning process. However, it is understood that using linear regression or another algorithm as part of a machine learning process is distinct from performing a statistical analysis such as regression with a spreadsheet program such as Excel. The machine learning process has the ability to continually learn and adjust the classifier as new data becomes available, and does not rely on explicit or rules-based programming. Statistical modeling relies on finding relationships between variables (e.g., mathematical equations) to predict an outcome.

In the present invention, the machine learning algorithms are "trained" by building a model from inputs. Those inputs may be retrospective data with a known diagnosis of cancer (including matched controls) and data from measured biomarkers and clinical factors of those patients. See Example 3 for training of an ANN using retrospective lung cancer patient data. In that instance the classifier, the trained machine learning algorithm, can classify new patient data into a category indicative of a likelihood of having cancer or into another category indicative of a likelihood of not having cancer. The category indicative of a likelihood of having cancer can be further divided into qualitative or quantitative sub-groups. Those qualitative groups may include identifiers such as low, medium, intermediate, high, or a combination thereof for a likelihood of having cancer. The quantitative groups may include identifiers such as a percentage, multiplier value, risk score, composite score or any numerical value that can be provided to the user for indicating the likelihood of having cancer. Those quantitative and qualitative groups may also be presented in a table, such as a "risk categorization table" as disclosed herein.

For example, according to one aspect of the present invention, a risk categorization of a population or cohort population of individuals is used to determine a quantified risk level for the presence of a cancer in an asymptomatic human subject. In some aspects, data used to determine the risk level may include, but is not limited to, a blood test that measures multiple biomarkers in the blood (only once or preferably serially to measure changes over time), a patient's medical records and person history such as smoking, as well as publically available sources of information pertaining to cancer risk. In certain embodiments, the risk categorization is herein referred to as a risk categorization table. As used herein, the term "table" is used in its broadest sense to refer to a grouping of data into a format providing for ease of interpretation or presentation, this includes, but is not limited to data provided from execution of computer program instructions or a software application, a table, a spreadsheet, etc. Thus, in one embodiment the risk categorization table is a grouping of a stratified population or cohort population (e.g., a human subject population). This stratification of human subjects is based on analysis of retrospective clinical samples (and may include other data) from subjects diagnosed as having cancer wherein the actual incidence of cancer, herein referred to as the positive predictive score (PPS) is determined for each stratified grouping. Ideally, the data from the population or cohort is collected on a longitudinal or prospective basis whereupon the determination of the presence or absence of cancer is made after the blood sample is taken and the biomarkers have been measured. Data collected in this manner can often overcome various limitations and biases inherent in retrospective studies which measure biomarkers in stored or archived samples already classified as being from cancer patients ("cases") versus patients without apparent cancers ("controls"). The data used to create the quantified risk levels preferably comes from very large numbers of patients, more than one thousand, more than ten thousand, or even more than one-hundred thousand patients. (Means for continuous improvements to the risk algorithms and tables using machine learning systems are described in the sections that follow.) The PPS is then converted to a multiplier indicating an increased likelihood of having the cancer by dividing the PPS by the reported incidence of cancer in the population or cohort of the population subject to stratification, (e.g., human subjects 50 years or older). Each grouping or cohort grouping is given a risk categorization identifier, including, but not limited to, low risk, intermediate-low risk, intermediate risk, intermediate-high risk and highest risk. Thus, in one embodiment, each category of the risk categorization table comprises 1) an increased likelihood of having the cancer, 2) a risk identifier and 3) a range of composite scores.

It is understood that the basis for the stratification of a population or of a cohort of a population of human subjects is based on, at least in part, 1) an identification of a certain cancer, 2) biomarkers that are associated with the cancer, (3) clinical parameter data, and in some cases, (4) publically available data including risk factors for having the cancer. A cohort shares the same cancer risk factors as the asymptomatic individual. Validation of the biomarkers to be used in the present methods may be provided by analyzing retrospective cancer samples along with age matched normal (non-cancer) samples and/or other controls. But, as stated above, prospective validation is better.

The present invention further provides a machine learning system, methods and computer readable media for analyzing results from a panel of biomarkers for a cancer along with data from a patient's medical record, and other publically available sources of information, and quantifying a human subject's increased risk (or in certain circumstances decreased risk) for the presence of the cancer in an asymptomatic human subject relative to a population. As used herein, the term "increased risk" refers to an increase for the presence of the cancer as compared to the known prevalence of that particular cancer across the population cohort. The present methods are based on the generation of a risk categorization table for a certain cancer; wherein there is no intended limitation on when this table is generated. Thus, the present method and risk categorization table is based, at least in part, on 1) the identification and clustering of a set of proteins and/or resulting autoantibodies to those proteins that can serve as markers for the presence of a cancer, 2) normalization and aggregation of the markers measured to generate a biomarker composite score; and, 3) medical data for a patient and other publically available sources of data for risk factors for having cancer; and (4) determination of threshold values used to divide patients into groups with varying degrees of risk for the presence of cancer in which the likelihood of an asymptomatic human subject having a quantified increased risk for the presence of the cancer is determined. A machine learning system may be utilized to determine the best cohort grouping as well as determine how biomarker composite data, medical data and other data are to be combined in order to generate a risk categorization in an optimal or near-optimal manner, e.g., correctly predicting which individuals have cancer with a low false positive rate. The machine learning system yields a numerical risk score for each patient tested, which can be used by physicians to make treatment decisions concerning the therapy of cancer patients or, importantly, to further inform screening procedures to better predict and diagnose early stage cancer in asymptomatic patients. Also, as described in more detail herein, the machine learning system is adapted to receive additional data as the system is used in a real-world clinical setting and to recalculate and improve the risk categories and algorithm so that the system becomes "smarter" the more that it is used.

B. Definitions

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

As used herein, the term "asymptomatic" refers to a patient or human subject that has not previously been diagnosed with the same cancer that their risk of having is now being quantified and categorized. For example, human subjects may show signs such as coughing, fatigue, pain, etc., but have not been previously diagnosed with lung cancer but are now undergoing screening to categorize their increased risk for the presence of cancer and for the present methods are still considered "asymptomatic".

As used herein, the term "AUC" refers to the Area Under the Curve, for example, of a ROC Curve. That value can assess the merit of a test on a given sample population with a value of 1 representing a good test ranging down to 0.5 which means the test is providing a random response in classifying test subjects. Since the range of the AUC is only 0.5 to 1.0, a small change in AUC has greater significance than a similar change in a metric that ranges for 0 to 1 or 0 to 100%. When the % change in the AUC is given, it will be calculated based on the fact that the full range of the metric is 0.5 to 1.0. A variety of statistics packages can calculate AUC for an ROC curve, such as, JMP™ or Analyse-It™. AUC can be used to compare the accuracy of the classification algorithm across the complete data range. Classification algorithms with greater AUC have, by definition, a greater capacity to classify unknowns correctly between the two groups of interest (disease and no disease). The classification algorithm may be the measure of a single molecule or as complex as the measure and integration of multiple molecules.

As used herein, the terms "biological sample" and "test sample" refer to all biological fluids and excretions isolated from any given subject. In the context of embodiments of the present invention such samples include, but are not limited to, blood, blood serum, blood plasma, urine, tears, saliva, sweat, biopsy, ascites, cerebrospinal fluid, milk, lymph, bronchial and other lavage samples, or tissue extract samples. In certain embodiments, blood, serum, plasma and bronchial lavage or other liquid samples are convenient test samples for use in the context of the present methods.

As used herein, the terms "cancer" and "cancerous" refer to or describe the physiological condition in mammals that is typically characterized by unregulated cell growth. Examples of cancer include but are not limited to, lung cancer, breast cancer, colon cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

As used herein, the term "cancer risk factors" refers to biological or environmental influences that are known risks associated with a particular cancer. These cancer risk factors include, but are not limited to, a family history of cancer (e.g., breast cancer), age, weight, sex, history of smoking tobacco, environmental factors (e.g., exposure to asbestos, exposure to radiation, etc.), occupational risk factors (e.g., coal miner, hazmat worker, etc.), genetic factors and mutations, and so forth. It is understood that these cancer risk factors, either individually or a combination thereof, contribute to selecting a cohort of the population used to develop a Risk Categorization Table and that this same cohort is then tested using the present methods and machine learning system to determine their increased risk for the presence of cancer as compared to the known prevalence of cancer across the cohort. In certain embodiments, cancer risk factors for lung cancer are a human subject aged 50 years or older with a history of smoking tobacco.

As used herein, the term "cohort" or "cohort population" refers to a group or segment of human subjects with shared factors or influences, such as age, family history, cancer risk factors, environmental influences, medical histories, etc. In one instance, as used herein, a "cohort" refers to a group of human subjects with shared cancer risk factors; this is also referred to herein as a "disease cohort". In another instance, as used herein, a "cohort" refers to a normal population group matched, for example by age, to the cancer risk cohort; also referred to herein as a "normal cohort". A "same cohort" refers to a group of human subjects having the same shared cancer risk factors as the individual undergoing assessment for a risk of having a disease such as cancer.

As used herein, the term "normalized" refers to data that has been normalized by any normalization technique known in the art, including but not limited to MoM, standard deviation normalization, sigmoidal normalization, etc.

As used herein, the term "environmental database" refers to a database comprising environmental risk factors for cancer, including but not limited to location, zip code. For patients who have lived or worked at a particular location for a number of years, the environmental database may be able to indicate whether those locations are associated with the presence of cancer. Information from the database may be based on journal articles, scientific studies, etc.

As used herein, the term "employment database" or "occupational database" refers to a database comprising occupational risk factors for cancer. Such data includes, but is not limited to, occupations known to be associated with the development of cancer, chemicals or carcinogens that a person employed in a particular occupation is likely to encounter, correlation between number of years in an occupation and risk (e.g., employment in an occupation for 5 years has a 5% increase in the risk of cancer, employment in the same occupation for 10 years has a 55% increase in the risk of cancer as compared to other occupations, etc.)

As used herein, the term "population database" refers to a database comprising demographics (e.g., gender, age, smoking history, family history, blood tests, biomarker tests, etc.) for a population of individuals. This data is supplied to a neural net for cohort analysis, and the neural net identifies the factors most predictive of the presence of cancer.

As used herein, the term "genetic database" refers to a database comprising information linking various types of genetic information to the presence of cancer (e.g., BRAF, V600E mutation, EGFP, gene SNPS, etc.)

As used herein, the term "raw images" refers to imaging studies prior to processing, e.g., XRAYs, CT scans, MRI, EEG, ECG, ultrasound etc.

As used herein, the term "medical history" refers to any type of medical information associated with a patient. In some embodiments, the medical history is stored in an electronic medical records database. Medical history may include clinical data (e.g., imaging modalities, blood work, biomarkers, cancerous samples and control samples, labs, etc.), clinical notes, symptoms, severity of symptoms, number of years smoking, family history of a disease, history of illness, treatment and outcomes, an ICD code indicating a particular diagnosis, history of other diseases, radiology reports, imaging studies, reports, medical histories, genetic risk factors identified from genetic testing, genetic mutations, etc.

As used herein, the term "converted numeric fields" refers to numeric data that has been extracted by natural language processing from unstructured data (e.g., years of smoking, frequency, etc.)

As used herein, the term "unstructured data" refers to text, free form text, etc. For example, unstructured data may include patient notes entered by a physician, annotations accompanying imaging studies, etc.

As used herein, the term "composite score" refers to an aggregation of the normalized values for the predetermined markers measured in the sample from the human subject and clinical parameter values. When used in the context of the risk categorization table and correlated to a stratified population grouping or cohort population grouping based on a range of composite scores in the Risk Categorization Table, the "composite score" is used, at least in part, by the machine learning system to determine the "risk score" for each human subject tested wherein the numerical value (e.g., a multiplier, a percentage, etc.) indicating increased likelihood of having the cancer for the stratified grouping becomes the "risk score". See, FIG. 10.

As used herein, the term "master composite score" refers to a composite score generated by the master neural net system, which includes one or more of biomarker composite scores, medical history, publically available sources of data related to cancer risk, etc., and is used to determine a risk category (e.g., low, medium, high, etc.) as well as to quantify risk for an individual.

In certain aspects the "cohort score" is also referred to herein as the "test score".

As used herein, the terms "differentially expressed gene," "differential gene expression" and their synonyms, which are used interchangeably, are used in the broadest sense and refer to a gene and/or resulting protein whose expression is activated to a higher or lower level in a subject suffering from a disease, specifically cancer, such as lung cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products (e.g., proteins), or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages.

As used herein, the term "gene expression profiling" is used in the broadest sense, and includes methods of quantification of mRNA and/or protein levels in a biological sample.

As used herein, the term "large volume of patients" is used in the broadest sense, and includes a number of patients including, e.g., several hundred patients, a thousand patients, several thousand patients, ten thousand patients, several tens of thousands of patients, and so forth, with any amount in between. In some embodiments, the number of patients is a number sufficient to train the system.

As used herein, the term "increased risk" refers to an increase in the risk level, for a human subject after biomarker testing and/or data analysis by the machine learning system, for the presence of a cancer relative to a population's known prevalence of a particular cancer before testing. In other words, a human subject's risk for cancer before biomarker testing and/or data analysis may be 2% (based on the understood prevalence of cancer in the population), but after biomarker testing and/or data analysis (based on the measure of one or more of biomarker concentration, a patient's medical data, public sources of data, etc.) the patient's risk for the presence of cancer may be 30% or alternatively reported as an increase of 15 times compared to the cohort. The machine learning system calculates the 30% risk of having the cancer and the increased risk of 15 times relative to the population or cohort population is provided in more detail herein. It is also contemplated, as will be apparent from the present risk categorization table and accompanying machine learning system, that it is possible that the re-categorization of a patient's risk for the presence of a cancer results in a risk that is less than the known prevalence of a particular cancer across a population or cohort population. For example, a human subject's risk for cancer before biomarker testing and/or data analysis may be 2% (based on the understood prevalence of cancer in the population), but after biomarker testing and/or data analysis (based on the measure of biomarkers and the patient's medical data and other data), their risk for the presence of cancer may be 1% or alternatively reported as an increase of 0.5 times compared to the cohort population. In this instance, "increased risk" refers to a change in risk level relative to a population before testing.

As used herein, the term "decreased risk" refers to a decrease in the risk level, for a human subject after biomarker testing and/or data analysis, for the presence of a cancer relative to a population's known prevalence of a particular cancer before testing. In this instance, "decreased risk" refers to a change in risk level relative to a population before testing.

As used herein, the term "lung cancer" refers to a cancer state associated with the pulmonary system of any given subject. In the context of another embodiment of the present invention, lung cancers include, but are not limited to, adenocarcinoma, epidermoid carcinoma, squamous cell carcinoma, large cell carcinoma, small cell carcinoma, non-small cell carcinoma, and bronchoalveolar carcinoma. Within the context of another embodiment of the present invention, lung cancers may be at different stages, as well as varying degrees of grading. Methods for determining the stage of a lung cancer or its degree of grading are well known to those skilled in the art.

As used herein, the terms "marker", "biomarker" (or fragment thereof) and their synonyms, which are used interchangeably, refer to molecules that can be evaluated in a sample and are associated with a physical condition. For example, markers include expressed genes or their products (e.g., proteins) or autoantibodies to those proteins that can be detected from human samples, such as blood, serum, solid tissue, and the like, that is associated with a physical or disease condition. Such biomarkers include, but are not limited to, biomolecules comprising nucleotides, amino acids, sugars, fatty acids, steroids, metabolites, polypeptides, proteins (such as, but not limited to, antigens and antibodies), carbohydrates, lipids, hormones, antibodies, regions of interest which serve as surrogates for biological molecules, combinations thereof (e.g., glycoproteins, ribonucleoproteins, lipoproteins) and any complexes involving any such biomolecules, such as, but not limited to, a complex formed between an antigen and an autoantibody that binds to an available epitope on said antigen. The term "biomarker" can also refer to a portion of a polypeptide (parent) sequence that comprises at least 5 consecutive amino acid residues, preferably at least 10 consecutive amino acid residues, more preferably at least 15 consecutive amino acid residues, and retains a biological activity and/or some functional characteristics of the parent polypeptide, e.g. antigenicity or structural domain characteristics. The present markers refer to both tumor antigens present on or in cancerous cells or those that have been shed from the cancerous cells into bodily fluids such as blood or serum. The present markers, as used herein, also refer to autoantibodies produced by the body to those tumor antigens. In one aspect, a "marker" as used herein refers to both tumor antigens and autoantibodies that are capable of being detected in serum of a human subject. It is also understood in the present methods that use of the markers in a panel may each contribute equally to the composite score or certain biomarkers may be weighted wherein the markers in a panel contribute a different weight or amount to the final composite score. Biomarker may include any biological substance indicative of the presence of cancer, including but not limited to, genetic, epigenetic, proteomic, glycomic or imaging biomarkers. Biomarkers include molecules secreted by tumors or cancer, including gene, gene expression, and protein-based products (tumor markers or antigens, cell free DNA, mRNA, etc.)

As used herein, the term "multiplier indicating an increased likelihood of having the cancer" refers to a numerical value of the risk categorization table and assigned to a patient sample after quantifying that patient's increased risk, relative to the cohort population, for the presence of having cancer. When used in the context of the risk categorization table when testing a human subject and correlated to a range of composite scores, the "multiplier indicating increased likelihood of having the cancer" becomes the "risk score" for each human subject tested. See, FIG. 10.

As used herein, the term "normalization" and its derivatives, when used in conjunction with measurement of biomarkers across samples and time, refer to mathematical methods where the intention is that these normalized values allow the comparison of corresponding normalized values from different datasets in a way that eliminates or minimizes differences and gross influences between the datasets. In one embodiment, multiple of median is used as the normalization methodology for the present methods.

As used herein, the terms "panel of markers", "panel of biomarkers" and their synonyms, which are used interchangeably, refer to more than one marker that can be detected from a human sample that together, are associated with the presence of a particular cancer. In an embodiment of the present application, the presence of the biomarkers are not individually quantified as an absolute value to indicate the presence of a cancer, but the measured values are normalized and the normalized value is aggregated (e.g., summed or weighted and summed, etc.) for inclusion within a biomarker composite score. As disclosed above, each marker in the panel may be given a weight of 1, or some other value that is either a fraction of 1 or a multiple of 1, depending on the contribution of the marker to the cancer being screened and the overall composition of the panel.

As used herein, the term "pathology" of (tumor) cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the term "known prevalence of cancer" refers to a prevalence of a cancer in a population before the human subject is tested and undergoes data analysis using the present methods. This known prevalence of cancer, can be a prevalence reported in the literature based on retrospective data or be determined by a machine learning system that takes into account factors such as age and more immediate and relevant history or a combination thereof. In this instance, a known prevalence of cancer in a cohort refers to a risk of having cancer prior to testing and analysis by the present methods and systems.

As used herein, the term "a positive predictive score," "a positive predictive value," or "PPV" refers to the likelihood that a score within a certain range on a biomarker test is a true positive result. It is defined as the number of true positive results divided by the number of total positive results. True positive results can be calculated by multiplying the test sensitivity times the prevalence of disease in the test population. False positives can be calculated by multiplying (1 minus the specificity) times (1—the prevalence of disease in the test population). Total positive results equal True Positives plus False Positives.

As used herein, the term "risk score" refers to a single numerical value that indicates an asymptomatic human subject's increased (or decreased) risk for the presence of a cancer as compared to the known prevalence of cancer in the disease cohort. In certain embodiments of the present methods, the composite score is calculated for a human subject and correlated to a multiplier indicating an increased likelihood of having the cancer, wherein the composite score is correlated based on the range of composite scores for each stratified grouping or cohort population grouping in the risk categorization table. In this way the composite score is converted to a risk score based on the multiplier indicating increased likelihood of having the cancer for the grouping that is the best match for the composite score. See, FIG. 10.

As used herein the term, "Receiver Operating Characteristic Curve," or, "ROC curve," is a plot of the performance of a particular feature for distinguishing two populations, patients with lung cancer, and controls, e.g., those without lung cancer. Data across the entire population (namely, the patients and controls) are sorted in ascending order based on the value of a single feature. Then, for each value for that feature, the true positive and false positive rates for the data are determined. The true positive rate is determined by counting the number of cases above the value for that feature under consideration and then dividing by the total number of patients. The false positive rate is determined by counting the number of controls above the value for that feature under consideration and then dividing by the total number of controls.

ROC curves can be generated for a single feature as well as for other single outputs, for example, a combination of two or more features that are combined (such as, added, subtracted, multiplied, weighted, etc.) to provide a single combined value which can be plotted in a ROC curve.

The ROC curve is a plot of the true positive rate (sensitivity) of a test against the false positive rate (1-specificity) of the test. ROC curves provide another means to quickly screen a data set.

As used herein, the term "screening" refers to a strategy used in a population to identify an unrecognized cancer in asymptomatic subjects, for example those without signs or symptoms of the cancer. As used herein, a cohort of the population (e.g., smokers aged 50 or older) are screened for a particular cancer (e.g., lung cancer) wherein the present method and system is applied to determine the quantified increased risk to those asymptomatic subjects for the presence of the cancer.

As used herein, the term "subject" refers to an animal, preferably a mammal, including a human or non-human. The terms "patient" and "human subject" may be used interchangeably herein.

As used herein, clinical data includes symptoms, differential diagnosis, active diseases, current medications, allergies, past disease history, family disease history, As used herein, the term "tumor," refers to all neoplastic cell growth and proliferation, whether malignant or benign, and all pre-cancerous and cancerous cells and tissues.

As used herein, the phrase "Weighted Scoring Method" refers to a method that involves converting the measurement of one biomarker that is identified and quantified in a test sample into one of many potential scores. A ROC curve can be used to standardize the scoring between different markers by enabling the use of a weighted score based on the inverse of the false positive % defined from the ROC curve. The weighted score can be calculated by multiplying the AUC by a factor for a marker and then dividing by the false positive % based on a ROC curve. The weighted score can be calculated using the formula:

$$\text{Weighted Score} = (AUC_x \times \text{factor})/(1 - \% \text{ specificity}_x)$$

wherein x is the marker; the, "factor," is a real number or integer (such as 0, 1, 2, 3, 4, 5, 6, 7, 8, 9, 10, 11, 12, 13, 14, 15, 16, 17, 18, 19, 20, 21, 22, 23, 24, 25 and so on)

throughout the panel; and the, "specificity," is a chosen value that does not exceed 95%. Multiplication of a factor for the panel allows the user to scale the weighted score. Hence, the measurement of one marker can be converted into as many or as few scores as desired.

The weighting provides higher scores for biomarkers with a low false positive rate (thereby having higher specificity) for the population of interest. The weighting paradigm can comprise electing levels of false positivity (1-specificity) below which the test will result in an increased score. Thus, markers with high specificity can be given a greater score or a greater range of scores than markers that are less specific.

Foundation for assessing the parameters for weighing can be obtained by determining presence of a marker in a population of patients with lung cancer and in normal individuals. The information (data) obtained from all the samples are used to generate a ROC curve and to create an AUC for each biomarker. A number of predetermined cutoffs and a weighted score are assigned to each biomarker based on the % specificity. That calculus provides a stratification of aggregate marker scores, and those marker scores can be used to define ranges that correlate to arbitrary risk categories of whether one has a higher or lower risk of having lung cancer. The number of categories can be a design choice or may be driven by the data. For example, a machine learning system may determine parameters for weighting markers, for thresholds, as well as for creating cohort populations.

C. Methods for Determining a Likelihood for the Presence of a Cancer in an Asymptomatic (or Vaguely Symptomatic) Human Using Machine Learning Classifiers In certain embodiments, provided herein is a computer implemented method for assessing the likelihood that a patient has cancer relative to a population. The asymptomatic patients that, after testing, have a likelihood for the presence of cancer relative to the population are those that a physician may select for follow-up diagnostic testing such as CT screening or analysis of a biopsy sample. Therefore, in certain embodiments, the method for assessing the likelihood that a patient has cancer relative to a population comprises 1) measuring the values of a panel of biomarkers in a sample from a patient; 2) obtaining clinical parameters from the patient; 3) utilizing a classifier generated by a machine learning system to classify the patient into a category indicative of a likelihood of having cancer or into another category indicative of a likelihood of not having cancer, wherein the classifier comprises a sensitivity of at least 70% and a specificity of at least 80%, and wherein the classifier is generated using a panel of biomarkers comprising at least two different biomarkers, and at least one clinical parameter; and, 4) providing a notification to a user for diagnostic testing when a patient is classified into a category indicating a likelihood of having cancer. The generation of the classifier used in the method herein is disclosed in detail below. Example 3 provides illustrative embodiments of a trained ANN for use to classify patients into a category indicative of a likelihood of having lung cancer or into another category indicative of a likelihood of not having lung cancer In certain embodiments, is provided a method of determining a quantified increased risk for the presence of a disease such as cancer in an asymptomatic human subject, may comprise: 1) measuring a concentration or an amount of each marker of a panel of markers in a sample from the human subject; 2) determining a normalized value of each marker in a sample from a human subject; 3) aggregating (e.g., summing, weighting, etc.) each normalized value to obtain a biomarker composite score for the human subject; 4) determining a biomarker velocity for one or more biomarkers; 5) obtaining data pertaining to a patient's medical records related to determining a risk for having cancer; 6) obtaining publically available information (e.g., environmental data, occupational data, genetic data, etc.) pertaining to an increased risk of cancer; 7) generating a master composite score for the human subject based on data from items 1-6 using a machine learning system; 8) quantifying the increased risk for the presence of cancer for the human subject as a risk score, by matching the master composite score to a risk category of a stratified cohort population or population, wherein each risk category comprises a numeric value indicating an increased likelihood of having the disease, e.g., cancer, correlated to a range of master composite scores, and wherein the risk categories, cohort population, and weighting of risk factors are determined by a machine learning system; and 9) providing a risk score for the human subject, whereby the quantified increased relative risk for the presence of a cancer in an asymptomatic patient relative to a population or cohort population has been determined.

One or more steps of the techniques presented herein can be performed in an automated or partially automated manner by a machine learning system, as described herein. If the method were to be performed via a machine learning system, then the performance of the method would further necessitate the use of the appropriate hardware, such as input, memory, processing, display and output devices, etc. and software.

i) Measuring Markers in a Sample

As part of the present method, a panel of markers from an asymptomatic human subject may be measured. There are many methods known in the art for measuring either gene expression (e.g., mRNA) or the resulting gene products (e.g., polypeptides or proteins) that can be used in the present methods. However, for at least 2-3 decades tumor antigens (e.g. CEA, CA-125, PSA, etc.) have been the most widely utilized biomarkers for cancer detection throughout the world and are the preferred tumor marker type for the present invention.

For tumor antigen detection, testing is preferably conducted using an automated immunoassay analyzer from a company with a large installed base. Representative analyzers include the Elecsys® system from Roche Diagnostics or the Architect® Analyzer from Abbott Diagnostics. Using such standardized platforms permits the results from one laboratory or hospital to be transferable to other laboratories around the world. However, the methods provided herein are not limited to any one assay format or to any particular set of markers that comprise a panel. For example, PCT International Pat. Pub. No. WO 2009/006323; US Pub. No. 2012/0071334; US Pat. Pub. No. 2008/0160546; US Pat. Pub. No. 2008/0133141; US Pat. Pub. No. 2007/0178504 (each herein incorporated by reference) teaches a multiplex lung cancer assay using beads as the solid phase and fluorescence or color as the reporter in an immunoassay format. Hence, the degree of fluorescence or color can be provided in the form of a qualitative score as compared to an actual quantitative value of reporter presence and amount.

For example, the presence and quantification of one or more antigens or antibodies in a test sample can be determined using one or more immunoassays that are known in the art. Immunoassays typically comprise: (a) providing an antibody (or antigen) that specifically binds to the biomarker (namely, an antigen or an antibody); (b) contacting a test sample with the antibody or antigen; and (c) detecting the presence of a complex of the antibody bound to the antigen in the test sample or a complex of the antigen bound to the antibody in the test sample.

Well known immunological binding assays include, for example, an enzyme linked immunosorbent assay (ELISA), which is also known as a "sandwich assay", an enzyme immunoassay (EIA), a radioimmunoassay (RIA), a fluoro-immunoassay (FIA), a chemiluminescent immunoassay (CLIA), a counting immunoassay (CIA), a filter media enzyme immunoassay (META), a fluorescence-linked immunosorbent assay (FLISA), agglutination immunoassays and multiplex fluorescent immunoassays (such as the Luminex Lab MAP), immunohistochemistry, etc. For a review of the general immunoassays, see also, Methods in Cell Biology: Antibodies in Cell Biology, volume 37 (Asai, ed. 1993); Basic and Clinical Immunology (Daniel P. Stites; 1991).

The immunoassay can be used to determine a test amount of an antigen in a sample from a subject. First, a test amount of an antigen in a sample can be detected using the immunoassay methods described above. If an antigen is present in the sample, it will form an antibody-antigen complex with an antibody that specifically binds the antigen under suitable incubation conditions as described herein. The amount, activity, or concentration, etc. of an antibody-antigen complex can be determined by comparing the measured value to a standard or control. The AUC for the antigen can then be calculated using techniques known, such as, but not limited to, a ROC analysis.

In another embodiment, gene expression of markers (e.g., mRNA) is measured in a sample from a human subject. For example, gene expression profiling methods for use with paraffin-embedded tissue include quantitative reverse transcriptase polymerase chain reaction (qRT-PCR), however, other technology platforms, including mass spectroscopy and DNA microarrays can also be used. These methods include, but are not limited to, PCR, Microarrays, Serial Analysis of Gene Expression (SAGE), and Gene Expression Analysis by Massively Parallel Signature Sequencing (MPSS).

Any methodology that provides for the measurement of a marker or panel of markers from a human subject is contemplated for use with the present methods. In certain embodiments, the sample from the human subject is a tissue section such as from a biopsy. In another embodiment, the sample from the human subject is a bodily fluid such as blood, serum, plasma or a part or fraction thereof. In other embodiments, the sample is a blood or serum and the markers are proteins measured therefrom. In yet another embodiment, the sample is a tissue section and the markers are mRNA expressed therein. Many other combinations of sample forms from the human subjects and the form of the markers are contemplated.

ii) Biomarkers

However, before measurement can be performed a panel of markers needs to be selected for a particular cancer being screened. Many markers are known for diseases, including cancers and a known panel can be selected, or as was done by the present Applicants, a panel can be selected based on measurement of individual markers in retrospective clinical samples wherein a panel is generated based on empirical data for a desired disease such as cancer, and preferably lung cancer. For example, US Publication No. 2013/0196868, the contents of which are herein incorporated by reference.

Examples of biomarkers that can be employed include molecules detectable, for example, in a body fluid sample, such as, antibodies, antigens, small molecules, proteins, hormones, enzymes, genes and so on. However, the use of tumor antigens has many advantages due to their widespread use over many years and the fact that validated and standardized detection kits are available for many of them for use with the aforementioned automated immunoassay platforms.

In a particular embodiment, a panel of markers is selected based on their association with lung cancer. The tumor antigens used in the study reported by Molina, et al., *Am J Respir Crit Care Med.* published online 14 Oct. 2015 "Assessment of a Combined Panel of Six Serum Tumor Markers for Lung Cancer", namely, CEA, CA15.3, SCC, CYFRA 21-1, NSE and ProGRP, are representative of those that may be used with the present invention.

In embodiments, a panel of biomarkers in combination with clinical parameters is selected from: 1) CA-125, CEA, CYFRA, NYESO Age, Smoking Status, Pack Years, COPD; and 2) CEA, CYFRA, NSE, Smoking Status, Age, Nodule Size. In other embodiments, a panel of biomarkers is selected from CA 19-9, CEA, CYFRA, NSE, Pro-GRP, SCC, CA 125, CA 15-3. CA 72.

Alternatively, the panel of markers is selected from anti-p53, anti-NY-ESO-1, anti-ras, anti-Neu, anti-MAPKAPK3, cytokeratin 8, cytokeratin 19, cytokeratin 18, CEA, CA125, CA15-3, CA19-9, Cyfra 21-1, serum amyloid A, proGRP and ai-anti-trypsin (US 20120071334; US 20080160546; US 20080133141; US 20070178504 (each herein incorporated by reference)). Many circulating proteins have more recently been identified as possible biomarkers for the occurrence of lung cancer, for example the proteins CEA, RBP4, hAAT, SCCA [Patz, E. F., et al., Panel of Serum Biomarkers for the Diagnosis of Lung Cancer. Journal of Clinical Oncology, 2007. 25(35): p. 5578-5583.]; the proteins IL6, IL-8 and CRP [Pine, S. R., et al., Increased Levels of Circulating Interleukin 6, Interleukin 8, C-Reactive Protein, and Risk of Lung Cancer. Journal of the National Cancer Institute, 2011. 103(14): p. 1112-1122.]; the proteins TNF-a, CYFRA 21-1, IL-1ra, MMP-2, monocyte chemotactic protein-1 & sE-selectin [Farlow, E. C., et al., Development of a Multiplexed Tumor-Associated Autoantibody-Based Blood Test for the Detection of Non-Small Cell Lung Cancer. Clinical Cancer Research, 2010. 16(13): p. 3452-3462.]; the proteins prolactin, transthyretin, thrombospondin-1, E-selectin, C—C motif chemokine 5, macrophage migration inhibitory factor, plasminogen activator inhibitor, receptor tyrosine-protein kinase, erbb-2, cytokeratin fragment 21.1, and serum amyloid A [Bigbee, W. L. P., et al.,—A Multiplexed Serum Biomarker Immunoassay Panel Discriminates Clinical Lung Cancer Patients from High-Risk Individuals Found to be Cancer-Free by CT Screening [Journal of Thoracic Oncology April, 2012. 7(4): p. 698-708.]; the proteins EGF, sCD40 ligand, IL-8, MMP-8 [Izbicka, E., et al., Plasma Biomarkers Distinguish Non-small Cell Lung Cancer from Asthma and Differ in Men and Women. Cancer Genomics-Proteomics, 2012. 9(1): p. 27-35.].

Additional tumor markers include human epididymal protein 4 [Roche Diagnostics (2015)]; calcitonin, PAP, BR 27.29, Her-2 [Siemens (2015)]; and HE-4 [Abbott (2015) and Fujirebio (2015)].

Novel ligands that bind to circulating, lung-cancer associated proteins which are possible biomarkers include nucleic acid aptamers to bind cadherin-1, CD30 ligand, endostatin, HSP90a, LRIG3, MIP-4, pleiotrophin, PRKCI, RGM-C, SCF-sR, sL-selectin, and YES [Ostroff, R. M., et al., Unlocking Biomarker Discovery: Large Scale Application of Aptamer Proteomic Technology for Early Detection of Lung Cancer. PLoS ONE, 2010. 5(12): p. e15003.]; monoclonal antibodies that bind leucine-rich alpho-2 glycoprotein 1 (LRG1), alpha-1 antichymotrypsin (ACT), complement C9, haptoglobin beta chain [Guergova-Kuras, M., et al., Discovery of Lung Cancer Biomarkers by Profiling the Plasma Proteome with Monoclonal Antibody Libraries. Molecular & Cellular Proteomics, 2011. 10(12).]; and the protein CizI [Higgins, G., et al., Variant CizI is a circulating biomarker for early-stage lung cancer. Proceedings of the National Academy of Sciences, 2012.].

Autoantibodies that are proposed to be circulating markers for lung cancer include p53, NY-ESO-1, CAGE, GBU4-5, Annexin 1, and SOX2 [Lam, S., et al., EarlyCDT-Lung: An Immunobiomarker Test as an Aid to Early Detection of Lung Cancer. Cancer Prevention Research, 2011. 4(7): p. 1126-1134.] and IMPDH, phosphoglycerate mutase, ubiquillin, Annexin I, Annexin II, and heat shock protein 70-9B (HSP70-9B) [Farlow, E. C., et al., Development of a Multiplexed Tumor-Associated Autoantibody-Based Blood Test for the Detection of Non-Small Cell Lung Cancer. Clinical Cancer Research, 2010. 16(13): p. 3452-3462.].

Micro-RNAs that are proposed to be circulating markers for lung cancer include miR-21, miR-126, miR-210, miR-486-5p [Shen, J., et al., Plasma microRNAs as potential biomarkers for non-small-cell lung cancer. Lab Invest, 2011. 91(4): p. 579-587.]; miR-15a, miR-15b, miR-27b, miR-142-3p, miR-301 [Hennessey, P. T., et al., Serum microRNA Biomarkers for Detection of Non-Small Cell Lung Cancer. PLOS ONE, 2012. 7(2): p. e32307.]; let-7b, let-7c, let-7d, let-7e, miR-10a, miR-10b, miR-130b, miR-132, miR-133b, miR-139, miR-143, miR-152, miR-155, miR-15b, miR-17-5p, miR-193, miR-194, miR-195, miR-196b, miR-199a*, miR-19b, miR-202, miR-204, miR-205, miR-206, miR-20b, miR-21, miR-210, miR-214, miR-221, miR-27a, miR-27b, miR-296, miR-29a, miR-301, miR-324-3p, miR-324-5p, miR-339, miR-346, miR-365, miR-378, miR-422a, miR-432, miR-485-3p, miR-496, miR-497, miR-505, miR-518b, miR-525, miR-566. miR-605, miR-638, miR-660, and miR-93 [United States Patent Application 20110053158]; hsa-miR-361-5p, hsa-miR-23b, hsa-miR-126, hsa-miR-527, hsa-miR-29a, hsa-let-7i, hsa-miR-19a, hsa-miR-28-5p, hsa-miR-185*, hsa-miR-23a, hsa-miR-1914*, hsa-miR-29c, hsa-miR-505*, hsa-let-7d, hsa-miR-378, hsa-miR-29b, hsa-miR-604, hsa-miR-29b, hsa-let-7b, hsa-miR-299-3p, hsa-miR-423-3p, hsa-miR-18a*, hsa-miR-1909, hsa-let-7c, hsa-miR-15a, hsa-miR-425, hsa-miR-93*, hsa-miR-665, hsa-miR-30e, hsa-miR-339-3p. hsa-miR-1307, hsa-miR-625*, hsa-miR-193a-5p, hsa-miR-130b, hsa-miR-17*, hsa-miR-574-5p and hsa-miR-324-3p. [United States Patent Application 20120108462]; miR-20a, miR-24, miR-25, miR-145, miR-152, miR-199a-5p, miR-221, miR-222, miR-223, miR-320 [Chen, X., et al., Identification of ten serum microRNAs from a genome-wide serum microRNA expression profile as novel noninvasive biomarkers for nonsmall cell lung cancer diagnosis. International Journal of Cancer, 2012. 130(7): p. 1620-1628.]; hsa-let-7a, hsa-let-7b, hsa-let-7d, hsa-miR-103, hsa-miR-126, hsa-miR-133b, hsa-miR-139-5p, hsa-miR-140-5p, hsa-miR-142-3p, hsa-miR-142-5p, hsa-miR-148a, hsa-miR-148b, hsa-miR-17, hsa-miR-191, hsa-miR-22, hsa-miR-223, hsa-miR-26a, hsa-miR-26b, hsa-miR-28-5p, hsa-miR-29a, hsa-miR-30b, hsa-miR-30c. hsa-miR-32, hsa-miR-328, hsa-miR-331-3p, hsa-miR-342-3p, hsa-miR-374a, hsa-miR-376a, hsa-miR-432-staR, hsa-miR-484, hsa-miR-486-5p, hsa-miR-566, hsa-miR-92a, hsa-miR-98 [Bianchi, F., et al., A serum circulating miRNA diagnostic test to identify asymptomatic high-risk individuals with early stage lung cancer. EMBO Molecular Medicine, 2011. 3(8): p. 495-503.] miR-190b, miR-630, miR-942, and miR-1284 [Patnaik, S. K., et al., MicroRNA Expression Profiles of Whole Blood in Lung Adenocarcinoma. PLOS ONE, 2012. 7(9): p. e46045.1.

In one embodiment, a panel of markers for lung cancer is selected from CEA (GenBank Accession CAE75559), CA125 (UniProtKB/Swiss-Prot: Q8WXI7.2), Cyfra 21-1 (NCBI Reference Sequence: NP_008850.1), anti-NY-ESO-1 (antigen NCBI Reference Sequence: NP_001318.1), anti-p53 (antigen GenBank: BAC16799.1) and anti-MAPKAPK3 (antigen NCBI Reference Sequence: NP_001230855.1), the first three are tumor marker proteins and the last three are autoantibodies.

In certain embodiments, a panel of markers comprises circulating markers associated with colorectal cancer (CRC); those include the microRNA miR-92 [Ng, E. K. O., et al., Differential expression of microRNAs in plasma of patients with colorectal cancer: a potential marker for colorectal cancer screening. Gut, 2009. 58(10): p. 1375-1381.]; aberrantly methylated SEPT9 DNA [deVos, T., et al., Circulating Methylated SEPT9 DNA in Plasma Is a Biomarker for Colorectal Cancer. Clinical Chemistry, 2009. 55(7): p. 1337-1346.]

In certain embodiments, a panel of markers comprises markers associated with a cancer selected from bile duct cancer, bone cancer, pancreatic cancer, cervical cancer, colon cancer, colorectal cancer, gallbladder cancer, liver or hepatocellular cancer, ovarian cancer, testicular cancer, lobular carcinoma, prostate cancer, and skin cancer or melanoma. In other embodiments, a panel of markers comprises markers associated with breast cancer.

A panel can comprise any number of markers as a design choice, seeking, for example, to maximize specificity or sensitivity of the assay. Hence, an assay of interest may ask for presence of at least one of two or more biomarkers, three or more biomarkers, four or more biomarkers, five or more biomarkers, six or more biomarkers, seven or more biomarkers, eight biomarkers or more as a design choice.

Thus, in one embodiment, the panel of biomarkers may comprise at least two, at least three, at least four, at least five, at least six, at least seven, at least eight, at least nine or at least ten or more different markers. In one embodiment, the panel of biomarkers comprises about two to ten different markers. In another embodiment, the panel of biomarkers comprises about four to eight different markers. In yet another embodiment, the panel of markers comprises about six different markers.

Generally, a sample is committed to the assay and the results can be a range of numbers reflecting the presence and level (e.g., concentration, amount, activity, etc.) of presence of each of the biomarkers of the panel in the sample.

The choice of the markers may be based on the understanding that each marker, when measured and normalized, contributed equally to determine the likelihood of the presence of the cancer. Thus in certain embodiments, each marker in the panel is measured and normalized wherein none of the markers are given any specific weight. In this instance each marker has a weight of 1.

In other embodiments, the choice of the markers may be based on the understanding that each marker, when measured and normalized, contributed unequally to determine the likelihood of the presence of the cancer. In this instance, a particular marker in the panel can either be weighted as a fraction of 1 (for example if the relative contribution is low), a multiple of 1 (for example if the relative contribution is high) or as 1 (for example when the relative contribution is neutral compared to the other markers in the panel). Thus, in certain embodiments, the present methods further comprising weighting the normalized values prior to aggregation (e.g., summation, weighting and summation, etc.) of the normalized values to obtain a composite score.

In still other embodiments, a neural net system may analyze values from biomarker panels without normalization of the values. Thus, the raw value obtained from the instrumentation to make the measurement may be analyzed directly.

The collection of markers in a multiplex assay may comprise varying levels of value or predictability in diagnosing disease. Hence, the impact of any one marker on the ultimate determination may be weighted based on the aggregated data obtained in screening populations and correlated with actual pathology to provide a more discriminating or effective diagnostic assay.

One approach is to find an intermediate ground by expanding the qualitative transformation of quantitative data into multiple categories, as compared to only a binary classification scheme.

a) Lung Cancer Biomarkers

One embodiment is directed to a method for assessing the likelihood of lung cancer. A research effort to identify panels of biomarkers that included a survey of known tumor protein biomarkers coupled with a discovery project for novel lung cancer specific biomarkers was previously conducted (PCT Publ. No. 2009/006323, incorporated herein by reference). This work indicates that a combination of markers can be used to increase sensitivity of testing for cancer without greatly affecting the specificity of the test. To accomplish this, markers were tested and analyzed in a way that is very different from the standard methods. This effort culminated in the establishment of a panel of six biomarkers that in the aggregate yield significant sensitivity and specificity for the early detection of lung cancer using the present methods. As disclosed herein, Applicants provide a new method and machine learning system that can be utilized to identify smokers at the highest levels of risk, based on a population or a cohort population, for follow-up testing by CT scanning.

In certain embodiments, the lung cancer biomarker panel comprises a series of three tumor marker proteins and three autoantibodies. Tumor markers, in such embodiments, are proteins released by the cancer itself into the patient's serum. Since the presence of these proteins or their increased expression is directly related to the cancer cells these markers tend to be specific to cancer, however they may often be found in more than one type of cancer. Furthermore, because these markers are derived directly from the tumor, their levels will depend (e.g., linearly, non-linearly, etc.) on the size of the tumor. This can make the markers less sensitive for the detection of early stage cancers. Autoantibodies are a function of the patient's immune response to the abnormal cancerous cells. Because the immune system amplifies its response even to a small amount of antigen, autoantibodies may be detected more easily in the early stage patient than proteins released by the cancer itself. Unfortunately due to the heterogeneity of the cancers that are classified as lung cancer and the individual differences in patient immune responses, a large panel of autoantibodies is required to sensitively detect all lung cancers. Our panel combines both tumor markers and autoantibodies to achieve the greatest sensitivity for early stage lung cancer.

In certain embodiments, the tumor markers incorporated into the present methods for lung cancer comprise CEA, CA-125 and Cyfra 21-1. All three of these markers have been extensively studied by others and are currently in clinical use for monitoring of other cancers. While none of these markers have fared well as a stand-alone marker for the early detection of lung cancer, two important points must be iterated: 1) these markers are not measured by the present method in the same way that they have been measured in the past for other indications, and 2) these markers are not deployed as stand-alone markers but rather are incorporated as part of an integrated panel of markers for re-stratification of patient risk. Specifically, results in the present methods for lung cancer are not based on an absolute serum level, but on an increase in level as compared to the median levels in matched control patients. As such, individual marker values as a total serum concentration are not measured; instead these three markers are incorporated in an aggregate biomarker composite score that has value only in re-categorizing patient risk for the presence of lung cancer. The tumor antigens used in the study reported by Molina, et al., *Am J Respir Crit Care Med*. published online 14 Oct. 2015 "Assessment of a Combined Panel of Six Serum Tumor Markers for Lung Cancer", namely, CEA, CA15.3, SCC, CYFRA 21-1, NSE and ProGRP, are representative of those that may be used with the present invention.

In certain embodiments, three autoantibodies are utilized in the present lung cancer test, wherein the autoantibodies comprise anti-p53, anti-NY-ESO-1 and anti-MAPKAPK3. As noted above, most autoantibodies are only found in a limited number of patients. These three autoantibodies are among those most commonly found in lung cancer, although each on its own has a rather limited value because they do contribute to the overall sensitivity of the test. p53 is a well-known tumor suppressor protein that is often mutated in cancer. Such mutations may be enough to break natural immune tolerance to the protein and thus the source of anti-p53 antibodies. NY-ESO-1 has been characterized as a tumor specific marker and thus auto-antibodies against this protein may represent a way to measure the levels of a tumor marker in early stage disease via immune amplification. MAPKAPK3 is a kinase protein that can be activated by several oncogenic pathways and thus may be more commonly up-regulated in lung cancer leading to the development of autoantibodies targeted against it.

In certain embodiments, the method for determining a quantified increased risk for the presence of a lung cancer in an asymptomatic human subject, comprises: 1) measuring a panel of markers in sample from a human subject (e.g., that is at least 50 years of age or older and has a history of smoking tobacco); 2) determining a normalized score for each marker; 3) summing the normalized score to obtain a composite score for the human subject, 4) quantifying the increased risk for the presence of the lung cancer for the human subject as a risk score, wherein the composite score is matched to a risk category of a grouping of stratified human subject populations wherein each risk category comprises a multiplier indicating increased likelihood of having the lung cancer correlated to a range of composite scores; and, 5) providing a risk score for the human subject, whereby the quantified increased risk for the presence of the lung cancer in an asymptomatic human subject has been determined.

In certain embodiments, the method of determining a quantified increased risk for the presence of a disease such as cancer in an asymptomatic human subject, may comprise: 1) measuring a concentration or an amount of each marker of a panel of markers in a sample from the human subject; 2) determining a normalized value of each marker in a sample from a human subject; 3) aggregating (e.g., summing, weighting, etc.) the normalized value using a machine learning system to obtain a biomarker composite score for the human subject; 4) determining a biomarker velocity for one or more biomarkers; 5) obtaining data pertaining to a patient's medical records; 6) obtaining publically available information (e.g., environmental data, occupational data, genetic data, etc.) pertaining to an increased risk of cancer; 7) generating a master composite score for the human subject based on data from items 1-6; 8) quantifying the increased risk for the presence of cancer for the human subject as a risk score, by matching the master composite score to a risk category of a stratified cohort population or population, wherein each risk category comprises a numeric value indicating an increased likelihood of having the disease, e.g., cancer, correlated to a range of master composite scores, wherein the risk categories, cohort population, and weighting of risk factors are determined by a machine learning system; and 9) providing a risk score for the human subject, whereby the quantified increased risk for the presence of a cancer in an asymptomatic human subject relative to a population or a cohort population has been determined.

It is understood that the disease cohort (e.g., a human subject that is at least 50 years of age or older and has a history of smoking tobacco) is independently determined and in this instance is well understood to be the "at risk" group for developing lung cancer. This present method and machine learning system re-categorizes those at-risk patients into risk categories by quantifying their true increased risk for the presence of lung cancer relative to their disease cohort.

In other embodiments, provided herein are methods of assessing the likelihood that a patient has lung cancer relative to a population or a cohort population comprising the steps of: obtaining a sample from the patient; measuring the levels of multiple biomarkers in the sample; calculating a biomarker composite score from the biomarker measurements; comparing the patient biomarker composite score to the biomarker composite scores of persons known to be at a high and a low risk for lung cancer; and determining the level of risk of the patient for having lung cancer relative to the population.

In this instance, an asymptomatic patient's cancer risk level, relative to a population or a cohort population is determined. In certain embodiments, the determination may comprise quantifying the risk level relative to the population or cohort population. In other aspects, the multiple biomarkers comprise two or more, three or more, four or more, five or more or six or more biomarkers. In one embodiment, the multiple biomarkers comprise six markers selected from CEA, CA125, Cyfra 21-1, Pro-GRP, anti-NY-ESO-1, anti-p53, anti-Cyclin E2 and anti-MAPKAPK3.

In other embodiments, obtaining a biomarker composite score may further comprise normalizing the measured biomarker values and aggregating the normalized values to form a biomarker composite score.

b) Pan-Cancer Biomarkers

In certain regions of the world, most notably in the Far East, many hospitals and "Health Check Centers" offer panels of tumor markers to patients as part of their annual physicals or check-ups. These panels are offered to patients without noticeable signs or symptoms of, or predisposition to, any particular cancer and are not specific to any one tumor type (i.e. "pan-cancer"). Exemplary of such testing approaches is the one reported by Y. H. Wen et al., *Clinica Chimica Acta* 450 (2015) 273-276, "Cancer Screening Through a Multi-Analyte Serum Biomarker Panel During Health Check-Up Examinations: Results from a 12-year Experience." The authors report on the results from over 40,000 patients tested at their hospital in Taiwan between 2001 and 2012. The patients were tested with the following biomarkers: AFP, CA 15-3, CA125, PSA, SCC, CEA, CA 19-9, and CYFRA, 21-1 using kits available from Roche Diagnostics, Abbott Diagnostics, and Siemens Healthcare Diagnostics. The sensitivity of the panel for identifying the four most commonly diagnosed malignancies in that region (i.e. liver cancer, lung cancer, prostate cancer, and colorectal cancer) was 90.9%, 75.0%, 100% and 76%, respectively. Subjects with at least one of the markers showing values above the cut-off point were considered positive for the assay. No algorithm was reported. Moreover, neither clinical parameters nor biomarker velocity were factored in with this test.

It is believed that the methods and machine learning systems according to the present invention can improve and enhance the pan-cancer biomarker panel reported by the Taiwanese group and readily permit its use in other parts of the world. For example, an algorithm that combines biomarker values with clinical parameters could be employed that automatically improves using the machine learning software.

iii) Normalization of Data

In certain embodiments, the value obtained from measuring the marker in the sample is normalized. There is no intended limitation on the methodology used to normalize the values of the measured biomarkers provided that the same methodology is used for testing a human subject sample as was used to generate the Risk Categorization Table. In alternative embodiments, the concertation of the measured biomarkers are used as input values for either training the machine learning algorithm or for classifying a patient into a category for the likelihood of having cancer.

Many methods for data normalization exist and are familiar to those skilled in the art. These include methods such as background subtraction, scaling, multiple of the median (MoM) analysis, linear transformation, least squares fitting, etc. The goal of normalization is to equate the varying measurement scales for the separate markers such that the resulting values may be combined according to a weighting scale as determined and designed by the user or by the machine learning system and are not influenced by the absolute or relative values of the marker found within nature.

US Publ. No. 2008/0133141 (herein incorporated by reference) teaches statistical methodology for handling and interpreting data from a multiplex assay. The amount of any one marker thus can be compared to a predetermined cutoff distinguishing positive from negative for that marker as determined from a control population study of patients with cancer and suitably matched normal controls to yield a biomarker composite score for each marker based on said comparison; and then combining the biomarker composite scores for each marker to obtain a biomarker composite score for the marker(s) in the sample. In some embodiments, biomarker velocity may also be included for one or more biomarkers.

The predetermined cutoffs can be based on ROC curves and the biomarker composite score for each marker can be calculated based on the specificity of the marker. Then, the biomarker composite score can be compared to a predetermined biomarker composite score to transform that biomarker composite score to a quantitative determination of the likelihood or risk of having lung cancer.

In certain embodiments, the quantitative determination of the likelihood or risk of having lung cancer is based upon the biomarker composite score, analysis of medical data pertaining to the patient, biomarker velocity data, as well as other public sources of information related to risk factors for cancer.

Another method for score transformation or normalization is, for example, applying the multiple of median (MoM) method of data integration. In the MoM method, the median value of each biomarker is used to normalize all measurements of that specific biomarker, for example, as provided in Kutteh et al. (Obstet. Gynecol. 84:811-815, 1994) and Palomaki et al. (Clin. Chem. Lab. Med.) 39:1137-1145, 2001). Thus, any measured biomarker level is divided by the median value of the cancer group, resulting in a MoM value. The MoM values can be aggregated or combined (e.g., summed, weighted and added, etc.) for each biomarker in the panel resulting in a panel MoM value or aggregate MoM score for each sample.

In other embodiments, as additional samples are tested and presence of cancer validated, the sample size of the cancer population and the normals for determining the median can be increased to yield more accurate population data. In other embodiments, as additional samples are tested and the presence of cancer is validated, this data is fed back into the machine learning system to generate more accurate predictions of a patient's risk for having cancer.

In the next step of the present methods, the normalized value for each biomarker is aggregated to generate a biomarker composite score for each subject. In certain embodiments, this method comprises summing the MoM score for each marker to obtain the biomarker composite score.

In other words, the biomarker composite score is derived by measuring the levels of each of the markers used in a panel for a particular cancer in arbitrary units and comparing these levels to the median levels found in previous validation studies. In one embodiment, the cancer is lung cancer and the panel comprises the six markers disclosed above wherein this method generates six initial scores representing the multiple of the median (MoM) for each marker for a given patient. These initial scores are aggregated (e.g., summed, etc.) to yield the biomarker composite score.

In certain embodiments, the markers are measured and those resulting values normalized and then aggregated to obtain a biomarker composite score. In certain aspects, normalizing the measured biomarker values comprises determining the multiple of median (MoM) score. In other aspects, the present method further comprises weighting the normalized values before aggregating to obtain a biomarker composite score. In still other embodiments, a machine learning system may be utilized to determine weighting of the normalized values as well as how to aggregate the values (e.g., determine which markers are most predictive, and assign a greater weight to these markers), based on the embodiments presented herein.

D. Risk Categorization Table

Present embodiments further comprise quantifying the increased risk for the presence of the cancer for the human subject as a risk score, wherein the composite score is matched to a risk category of a grouping of stratified human subject populations wherein each risk category comprises a multiplier (or percentage) indicating an increased likelihood of having the cancer correlated to a range of biomarker composite scores. This quantification is based on the predetermined grouping of a stratified cohort of human subjects. In one embodiment, the grouping of a stratified population of human subjects, or stratification of a disease cohort, is in the form of a risk categorization table. The selection of the disease cohort, the cohort of human subjects that share cancer risk factors, are well understood by those skilled in the art of cancer research. In certain embodiments, the cohort may share an age category and smoking history. However, it is understood that the cohort, and the resulting stratification, may be more multidimensional and take into account further environmental, occupational, genetic, or biological factors (e.g. epidemiological factors).

In certain embodiments, the grouping of a stratified human subject population used to determine a quantified increased risk for the presence of a cancer in an asymptomatic human subject, comprises: at least three risk categories, wherein each risk category comprises: 1) a multiplier (or percentage) indicating an increased likelihood of having the cancer, 2) a risk category and 3) a range of composite scores. In certain aspects, wherein an individual risk score is generated by aggregating the normalized values determined from a panel of markers for the cancer to obtain a biomarker composite score that is correlated to a risk category of the risk categorization table. In a further aspect, the normalized values are determined as multiple of median (MoM) scores.

The risk identifier for a risk category is a label given to a specific group to provide context for the range of biomarker composite scores (and including other data, such as medical history) and the risk score, a multiplier (or percentage) indicating an increased likelihood of having the cancer in each group. In certain embodiments, the risk identifier is selected from low risk, intermediate-low risk, intermediate risk, intermediate-high risk and highest risk. These risk identifiers are not intended to be limiting, but may include other labels as dictated by the data used to generate the table and/or further refine the context of the data.

The risk score indicating an increased likelihood of having the cancer is a numerical value, such as 13.4; 5.0; 2.1; 0.7; and 0.4. This value is empirically derived and will change depending on the data, cohort of the subject population, type of cancer, medical records data, occupational and environmental factors, biomarkers, biomarker velocity, etc. and so on. Thus, the multiplier indicating an increased likelihood of having the cancer may be a numerical value selected from 2, 3, 4, 5, 6, 7, 8, 9, 10, 11, 12, 13, 14, 15, 16, 17, 18, 19 20, 21, 22, 23, 24, 25, 26, 27, 28, 29, and 30, and so on, or some fraction thereof. The risk score may be represented as a numerical multiplier, e.g., 2×, 5×, etc., wherein the numerical multiplier indicates the increased likelihood over the normal prevalence of cancer in the cohort population that formed the basis for the stratification, for the human subject at the time of testing or as a percentage, indicating a percent increase in risk relative to the normal prevalence of cancer. In other words, the human subject is from the same disease cohort as the one used to generate the risk categorization table. In the example of lung cancer, a disease cohort may be a human subject aged 50 years or older with a history of smoking tobacco. Thus, for example, if a patient receives a risk score of 13.4×, then that human subject has a 13.4 times increased risk for the presence of the cancer relative to the population.

As disclosed above, this multiplier value is empirically determined and in the present instance is determined from retrospective clinical samples. As such the stratification of human subjects into cohort populations is based on analysis of retrospective clinical samples from subjects having a cancer wherein the actual incidence of cancer, or the positive predictive score, is determined for each stratified grouping. The specifics of these techniques are detailed throughout the application and in the example section.

In general, once a population of human subjects has been stratified a positive predictive score can be determined, when retrospective samples with a known medical history are used, for each stratified grouping. This actual incidence of cancer in each of these groups is then divided by the reported incidence of cancer across the population of human subjects. For example, if the positive predictive score for one of the groupings from the stratified population of human subjects was 27%, this value would then be divided by the actual incidence of cancer across the cohort of the population that was stratified (e.g. 2%) to yield a multiplier of 13.5. In this scenario, the multiplier indicating increased likelihood of having the cancer is 13.5 and a subject tested that had a biomarker composite score matched to this category would have a risk factor of 13.5×. In other words, at the time of testing, that human subject would be 13.5 times more likely to have the presence of cancer than the general population in that particular cohort.

By stratifying data based on these techniques, a data transformation into a more quantitative risk categorization is provided that offers improved guidance for selecting patients for follow-up tests in light of the costs of lung cancer confirmation, for example a CAT scan or a PET scan, as well as patient compliance. Hence, because lung cancer incidence in the at risk population of heavy smokers is about 2%, that percentage was used as the cutoff point between a likelihood of having cancer and not, meaning, at that level the individual was equally likely to have cancer or not have cancer, that is, 1. Positive predictive values were determined using the disease prevalence of 2% and then that positive predictive value was divided by two to yield another risk value interpreted as the likelihood of having lung cancer as a multiple of that of the normal population risk, which can be considered as 1 or equally likely, or as a 2% risk based on population studies.

An example of a risk categorization table is provided in FIG. 10. The first column of the risk categorization table is a range of master composite scores. In the example provided herein, biomarker composite scores were generated from normalizing the data from the panel of measured biomarkers. A machine learning system may be utilized to aggregate the normalized biomarker scores along with other information (e.g., medical information, publically available information, etc.) to generate a master composite score. These master composite scores may be grouped to provide a range and to drive stratification of the cohort population. The specifics of this methodology are detailed throughout the specification, including the Example section.

By transforming the biomarker composite score and other information (e.g., medical information, publically available information, etc.) into a risk category that is based on cohort population data, the physician and patient then can assess whether follow-up is required, necessary or recommended based on whether there is a greater risk that is just slightly above that of any smoker, i.e., 2%, or is higher because of a greater master composite score, which indicates greater consideration by the patient and physician.

By further data transformation of the PPV, the physician and patient will be the beneficiary of a quantitative value indicating the prevalence of cancer amongst smokers which provides improved resolution of the risk of cancer in light of the biomarker assay. Hence, a patient with a master composite score of 20 or greater has a 13.4-fold greater likelihood of having lung cancer than any other heavy smoker, See FIG. 10. That 13.4× multiplier translates to an overall risk of about 27% of having lung cancer. That is, while all heavy smokers have a 1 in 50 chance of having lung cancer prior to testing, with a master composite score of 20 or more after testing, that individual has a 1 in 4 chance of having lung cancer. Therefore, that person should consider follow-up testing to visualize whether any cancer (e.g., lung cancer) is present, and to make any behavioral changes to reduce the risk of cancer.

Thus, in certain embodiments, the method for determining a quantified increased risk for the presence of lung cancer in an asymptomatic human subject, comprises: 1) measuring a level of CEA, CA125, Cyfra 21-1, anti-NY-ESO-1, anti-p53 and anti-MAPKAPK3 in a serum sample from the human subject, wherein the human subject is at least 50 years of age or older and has a history of smoking tobacco; 2) determining a normalized score for each marker; 3) summing or aggregating the normalized score to obtain a biomarker composite score for the human subject, 4) quantifying the increased risk for the presence of the lung cancer for the human subject as a risk score, wherein the biomarker composite score is matched to one of at least three risk categories of a grouping of a stratified cohort human subject population wherein each risk category comprises a multiplier or other numeric value indicating an increased likelihood of having the lung cancer correlated to a range of biomarker composite scores; and, 5) providing a risk score for the human subject, whereby the quantified increased risk for the presence of the lung cancer in an asymptomatic human subject has been determined.

In certain embodiments, the step of normalizing comprises determining the multiple of median (MoM) score for each marker. In this instance, the MoM score is then subsequently summed or aggregated to obtain a biomarker composite score.

After quantifying the increased risk for presence of the cancer in the form of a risk score, this score may be provided in a form amendable to understanding by a physician. In certain embodiments the risk score is provided in a report. In certain aspects, the report may comprise one or more of the following: patient information, a risk categorization table, a risk score relative to a cohort population, one or more biomarker test scores, a biomarker composite score, a master composite score, identification of the risk category for the patient, an explanation of the risk categorization table, and the resulting test score, a list of biomarkers tested, a description of the disease cohort, environmental and/or occupational factors, cohort size, biomarker velocity, genetic mutations, family history, margin of error, and so on.

E. Use of Methods to Aid in the Early Detection of Lung Cancer

The use in a clinical setting of the embodiments presented herein are now described in the context of lung cancer screening. It should be appreciated, however, that lung cancer is only one of many cancer types that can benefit from the embodiments of the present invention.

Primary care healthcare practitioners, who may include physicians specializing in internal medicine or family practice as well as physician assistants and nurse practitioners, are among the users of the techniques disclosed herein. These primary care providers typically see a large volume of patients each day and many of these patients are at risk for lung cancer due to smoking history, age, and other lifestyle factors. In 2012 about 18% of the U.S. population was current smokers and many more were former smokers with a lung cancer risk profile above that of a population that has never smoked.

The aforementioned NLST study (See, background section) concluded that heavy smokers over a certain age who undergo yearly screening with CT scans have a substantial reduction in lung cancer mortality as compared to those who are not similarly screened. Nevertheless, for the reasons discussed above, very few at risk patients are undergoing annual CT screening. For these patients the testing paradigm presented herein offers an alternative.

A blood sample from patients with a heavy smoking history (e.g. having smoked at least a pack of cigarettes per day for 20 years or more) is sent to a laboratory qualified to test the sample using a panel of biomarkers with adequate sensitivity and specificity for early stage lung cancer. Non limiting lists of such biomarkers are herein included throughout the specification including the examples. In lieu of blood, other suitable bodily fluids such a sputum or saliva might also be utilized.

A master composite score for that patient is then generated using the techniques described herein. Using the master composite score the patient's risk of having lung cancer, as compared to others having a comparable smoking history and age range, can then be calculated using e.g., a risk categorization table, software application, etc., such as the one shown in FIG. 10. If the risk calculation is to be made at the point of care, rather than at the laboratory, a software application compatible with mobile devices (e.g. a tablet or smart phone) may be employed.

Once the physician or healthcare practitioner has a risk score for the patient (i.e. the likelihood that the patient has lung cancer relative to a population of others with comparable epidemiological factors) follow-up testing can be recommended for those at higher risk, such as CT scanning. It should be appreciated that the precise numerical cut off above which further testing is recommended may vary depending on many factors including, without limitation, (i) the desires of the patients and their overall health and family history, (ii) practice guidelines established by medical boards or recommended by scientific organizations, (iii) the physician's own practice preferences, and (iv) the nature of the biomarker test including its overall accuracy and strength of validation data.

It is believed that use of the embodiments presented herein will have the twin benefits of ensuring that the most at risk patients undergo CT scanning so as to detect early tumors that can be cured with surgery while reducing the expense and burden of false positives associated with stand-alone CT screening.

F. Kits

One or more biomarkers, one or more reagents for testing the biomarkers, cancer risk factor parameters, a risk categorization table and/or system or software application capable of communicating with a machine learning system for determining a risk score, and any combinations thereof are amenable to the formation of kits (such as panels) for use in performing the present methods.

In certain embodiments, the kit can comprise (a) reagents containing at least one antibody for quantifying one or more antigens in a test sample, wherein said antigens comprise one or more of: (i) cytokeratin 8, cytokeratin 19, cytokeratin 18, CEA, CA125, CA15-3, SCC, CA19-9, proGRP, Cyfra 21-1, serum amyloid A, alpha-1-anti-trypsin and apolipoprotein CIII; or (ii) CEA, CA125, Cyfra 21-1, NSE, SCC, ProGRP, AFP, CA-19-9. CA 15-3 and PSA; (b) reagents containing one or more antigens for quantifying at least one antibody in a test sample; wherein said antibodies comprise one or more of: anti-p53, anti-TMP21, anti-NPC1L1C-domain, anti-TMOD1, anti-CAMK1, anti-RGS1, anti-PACSIN1, anti-RCV1, anti-MAPKAPK3, anti-NY-ESO-1 and anti-Cyclin E2; and (c) a system, an apparatus, or one or more computer programs/software applications for performing the steps of normalizing the amount of each antigen and/or antibody measured in the test sample, summing or aggregating those normalized values to obtain a biomarker composite score, combining the biomarker composite score with other factors associated with an increased risk of cancer in a cohort population to generate a master composite score, and determining and assigning a risk score to each patient by correlating the master composite score to a risk categorization table using a software application and using the quantified increased risk for the presence of the cancer as an aid for further definitive cancer screening.

In the case of tumor antigens as biomarkers, the source of these kits is preferably from a supplier who has developed, optimized, and manufactured them to be compatible with one of the aforementioned automated immunoassay analyzers. Examples of such suppliers include Roche Diagnostics (Basel, Switzerland) and Abbott Diagnostics (Abbott Park, Illinois). The advantage of using kits so manufactured is that they are standardized to yield consistent results from laboratory to laboratory if the manufacturer's protocol for sample collection, storage, preparation, etc. are meticulously followed. That way data generated from a medical institution or region of the world where cancer screening is commonplace can be used to build or improve the algorithms according to the present invention that can be used in medical institutions or regions where there is less history of this type of testing.

The reagents included in the kit for quantifying one or more regions of interest may include an adsorbent which binds and retains at least one region of interest contained in a panel, solid supports (such as beads) to be used in connection with said absorbents, one or more detectable labels, etc. The adsorbent can be any of numerous adsorbents used in analytical chemistry and immunochemistry, including metal chelates, cationic groups, anionic groups, hydrophobic groups, antigens and antibodies.

In certain embodiments, the kit comprises the necessary reagents to quantify at least one of the following antigens, cytokeratin 19, cytokeratin 18, CA 19-9, CEA, CA-15-3, CA125, SCC, Cyfra 21-1, serum amyloid A, and ProGRP. In another embodiment, the kit comprises the necessary reagents to quantify at least one of the following antibodies anti-p53, anti-TMP21, anti-NPC1L1C-domain, anti-TMOD1, anti-CAMK1, anti-RGS1, anti-PACSIN1, anti-RCV1, anti-MAPKAPK3, anti-NY-ESO-1 and anti-Cyclin E2.

In some embodiments, the kit further comprises computer readable media for performing some or all of the operations described herein. The kit may further comprise an apparatus or system comprising one or more processors operable to receive the concentration values from the measurement of markers in a sample and configured to execute computer readable media instructions to determine a biomarker composite score, combine the biomarker composite score with other risk factors to generate a master composite score and compare the master composite score to a stratified cohort population comprising multiple risk categories (e.g. a master risk categorization table) to provide a risk score.

G. Apparatus

Embodiments of the present invention further provide for an apparatus for assessing a subject's risk level for the presence of cancer and correlating the risk level with an increase or decrease of the presence of cancer after testing relative to a population or a cohort population. The apparatus may comprise a processor configured to execute computer readable media instructions (e.g., a computer program or software application, e.g., a machine learning system, to receive the concentration values from the evaluation of biomarkers in a sample and, in combination with other risk factors (e.g., medical history of the patient, publically available sources of information pertaining to a risk of developing cancer, etc.) may determine a master composite score and compare it to a grouping of stratified cohort population comprising multiple risk categories (e.g. a risk categorization table) and provide a risk score. The methods and techniques for determining a master composite score and a risk score are described herein.

The apparatus can take any of a variety of forms, for example, a handheld device, a tablet, or any other type of computer or electronic device. The apparatus may also comprise a processor configured to execute instructions (e.g., a computer software product, an application for a handheld device, a handheld device configured to perform the method, a world-wide-web (WWW) page or other cloud or network accessible location, or any computing device. In other embodiments, the apparatus may include a handheld device, a tablet, or any other type of computer or electronic device for accessing a machine learning system provided as a software as a service (SaaS) deployment. Accordingly, the correlation may be displayed as a graphical representation, which, in some embodiments, is stored in a database or memory, such as a random access memory, read-only memory, disk, virtual memory, etc. Other suitable representations, or exemplifications known in the art may also be used.

The apparatus may further comprise a storage means for storing the correlation, an input means, and a display means for displaying the status of the subject in terms of the particular medical condition. The storage means can be, for example, random access memory, read-only memory, a cache, a buffer, a disk, virtual memory, or a database. The input means can be, for example, a keypad, a keyboard, stored data, a touch screen, a voice-activated system, a downloadable program, downloadable data, a digital interface, a hand-held device, or an infrared signal device. The display means can be, for example, a computer monitor, a cathode ray tube (CRT), a digital screen, a light-emitting diode (LED), a liquid crystal display (LCD), an X-ray, a compressed digitized image, a video image, or a hand-held device. The apparatus can further comprise or communicate with a database, wherein the database stores the correlation of factors and is accessible to the user.

In another embodiment of the present invention, the apparatus is a computing device, for example, in the form of a computer or hand-held device that includes a processing unit, memory, and storage. The computing device can include, or have access to a computing environment that comprises a variety of computer-readable media, such as volatile memory and non-volatile memory, removable storage and/or non-removable storage. Computer storage includes, for example, RAM, ROM, EPROM & EEPROM, flash memory or other memory technologies, CD ROM, Digital Versatile Disks (DVD) or other optical disk storage, magnetic cassettes, magnetic tape, magnetic disk storage or other magnetic storage devices, or other medium known in the art to be capable of storing computer-readable instructions. The computing device can also include or have access to a computing environment that comprises input, output, and/or a communication connection. The input can be one or several devices, such as a keyboard, mouse, touch screen, or stylus. The output can also be one or several devices, such as a video display, a printer, an audio output device, a touch stimulation output device, or a screen reading output device. If desired, the computing device can be configured to operate in a networked environment using a communication connection to connect to one or more remote computers. The communication connection can be, for example, a Local Area Network (LAN), a Wide Area Network (WAN) or other networks and can operate over the cloud, a wired network, wireless radio frequency network, and/or an infrared network.

H. Biomarker Velocity

Present invention embodiments may also utilize biomarker velocity to assess a risk of having cancer, e.g., lung cancer. As opposed to evaluating a single concentration of a biomarker, e.g., with regard to whether that biomarker is above a given threshold at a single point in time, biomarker velocities reflect biomarker concentrations as functions of time. By evaluating a series of a biomarker levels over time (e.g., time t=0, t=3 months, t=6 months, t=1 year, etc.) for an individual patient, a velocity (or rate of increase) of the biomarker can be determined. Based on this type of methodology, a patient's risk of developing cancer can be stratified into high risk versus low risk (or any number of categories in between) based on the velocity.

Independent reports in the medical literature demonstrating that measuring change in tumor antigen levels over time in ovarian, pancreatic, and prostate cancer is superior to a single reading include Menon et al. J Clin Oncol May 11, 2015; Lockshin et al. PLOS One, April 2014; and Mikropoulos et. al., J Clin Oncol 33, 2015 (suppl7; abstr16). In at least one study, serial screening doubled the cancer detection rate as compared to single, one-time threshold based screening.

Menon also disclosed an algorithm that identifies a spike in the levels of one or more biomarkers, as compared to that patient's previous test score, and automatically advises the patient and the provider to be tested more frequently (e.g., quarterly) or to take other actions.

I. Artificial Intelligence Systems for Predictive Analytics for Early Detection of Lung Cancer Artificial intelligence systems include computer systems configured to perform tasks usually accomplished by humans, e.g., speech recognition, decision making, language translation, image processing and recognition, etc. In general, artificial intelligence systems have the capacity to learn, to maintain and access a large repository of information, to perform reasoning and analysis in order to make decisions, as well as the ability to self-correct.

Artificial intelligence systems may include knowledge representation systems and machine learning systems. Knowledge representation systems generally provide structure to capture and encode information used to support decision making. Machine learning systems are capable of analyzing data to identify new trends and patterns in the data. For example, machine learning systems may include neural networks, induction algorithms, genetic algorithms, etc. and may derive solutions by analyzing patterns in data. As generally understood in the art, linear statistical models such as logistic regression are not considered machine learning algorithms.

Figure 13:
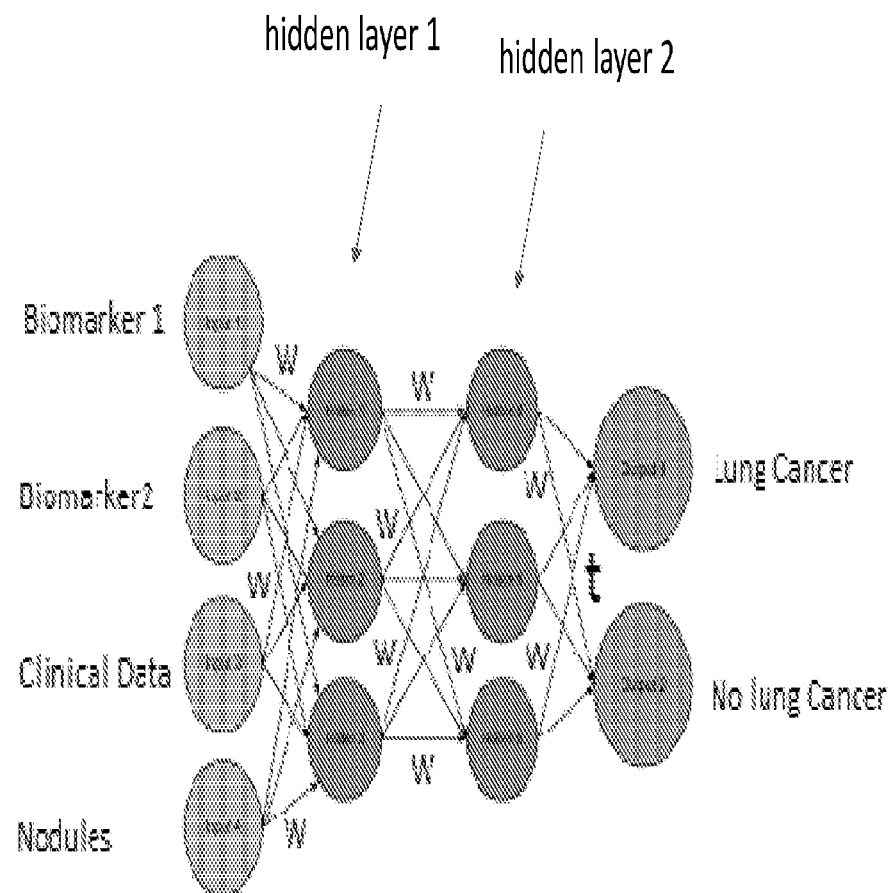
FIG. 13 is an example illustration of a neural net with at least two biomarker inputs and at least one clinical data input, with two levels of hidden layers and two outputs, in accordance with example embodiments.

In some embodiments, one or more neural nets may be used to classify an individual patient into one of a plurality of categories, e.g., a category indicative of a likelihood of cancer or a category indicating that lung cancer is not likely. Inputs to the neural net may include a panel of biomarkers associated with the presence of cancer as well as clinical parameters (see, e.g., FIG. 13). In embodiments, clinical parameters include one or more of the following: (1) age; (2) gender; (3) smoking history in years; (4) number of packs per year; (5) symptoms; (6) family history of cancer; (7) concomitant illnesses; (8) number of nodules; (9) size of nodules; and (10) imaging data and so forth. In other embodiments, the clinical parameters include smoking history in years, number of packs per year, and age. In still other embodiments, the panel of biomarkers comprises any two, any three, any four, any five, any six, any seven, any eight, any nine, or any ten biomarkers. In preferred embodiments, the panel of biomarkers comprises two or more biomarkers selected from the group consisting of: AFP, CA125, CA 15-3, CA 19-19, CEA, CYFRA 21-1, HE-4, NSE, Pro-GRP, PSA, SCC, anti-Cyclin E2, anti-MAPKAPK3, anti-NY-ESO-1, and anti-p53. In other embodiments, the panel of biomarkers comprises CA 19-9. CEA, CYFRA 21-1, NSE, Pro-GRP, and SCC. In still other embodiments, the panel of biomarkers comprises AFP, CA125, CA 15-3, CA-19-9, CEA, HE-4, and PSA. In yet other embodiments, the panel of biomarkers comprises AFP, CA125, CA 15-3, CA-19-9, Calcitonin, CEA, PAP, and PSA. In other embodiments, the panel of biomarkers comprises AFP, BR 27.29, CA12511, CA 15-3, CA-19-9, Calcitonin, CEA, Her-2, and PSA.

A variety of machine learning models are available, including support vector machines, decision trees, random forests, neural networks or deep learning neural networks. Generally, support vector machines (SVMs) are supervised learning models that analyze data for classification and regression analysis. SVMs may plot a collection of data points in n-dimensional space (e.g., where n is the number of biomarkers and clinical parameters), and classification is performed by finding a hyperplane that can separate the collection of data points into classes. In some embodiments, hyperplanes are linear, while in other embodiments, hyperplanes are non-linear. SVMs are effective in high dimensional spaces, are effective in cases in which the number of dimensions is higher than the number of data points, and generally work well on data sets with clear margins of separation. Decision trees are a type of supervised learning algorithm also used in classification problems. Decision trees may be used to identify the most significant variable that provides the best homogenous sets of data. Decision trees split groups of data points into one or more subsets, and then may split each subset into one or more additional categories, and so forth until forming terminal nodes (e.g., nodes that do not split). Various algorithms may be used to decide where a split occurs, including a Gini Index (a type of binary split), Chi-Square, Information Gain, or Reduction in Variance. Decision trees have the capability to rapidly identify the most significant variables among a large number of variables, as well as identify relationships between two or more variables. Additionally, decision trees can handle both numerical and non-numerical data. This technique is generally considered to be a non-parametric approach, e.g., the data does not have to fit a normal distribution.

Random forest (or random decision forest) is a suitable approach for both classification and regression. In some embodiments, the random forest method constructs a collection of decision trees with controlled variance. Generally, for M input variables, a number of variables (nvar) less than M is used to split groups of data points. The best split is selected and the process is repeated until reaching a terminal node. Random forest is particularly suited to process a large number of input variables (e.g., thousands) to identify the most significant variables. Random forest is also effective for estimating missing data.

Neural nets (also referred to as artificial neural nets (ANNs)) are described throughout this application. A neural net, which is a non-deterministic machine learning technique, utilizes one or more layers of hidden nodes to compute outputs. Inputs are selected and weights are assigned to each input. Training data is used to train the neural networks, and the inputs and weights are adjusted until reaching specified metrics, e.g., a suitable specificity and sensitivity. An example process of training a neural net is provided in FIG. 14.

ANNs may be used to classify data in cases in which correlation between dependent and independent variables is not linear or in which classification cannot be easily performed using an equation. More than 25 different types of ANNs exist, with each ANN yielding different results based on different training algorithms, activation/transfer functions, number of hidden layers, etc. In some embodiments, more than 15 types of transfer functions are available for use with the neural network. Prediction of the likelihood of having cancer is based upon one or more of the type of ANN, the activation/transfer function, the number of hidden layers, the number of neurons/nodes, and other customizable parameters.

Deep learning neural networks, another machine learning technique, are similar to regular neural nets, but are more complex (e.g., typically have multiple hidden layers) and are capable of automatically performing operations (e.g., feature extraction) in an automated manner, generally requiring less interaction with a user than a traditional neural net.

According to present invention embodiments, machine learning methods are able to classify individuals having a likelihood of cancer with at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% sensitivity when the specificity is set at 80%. This result is significantly better than linear statistical models such as threshold classification with a single variable or multivariate logistic regression with multiple variables. In some embodiments, at least a 5% improvement, at least a 10% improvement, at least a 15% improvement, at least a 20% improvement, at least a 25% improvement, or at least a 30% improvement is achieved using artificial neural nets as compared to traditional statistical methods such as traditional logistic regression or multivariate linear regression. See FIG. 15A-D and Example 4.

In other embodiments, the present machine learning methods are able to classify individuals having a likelihood of cancer with at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% sensitivity when the specificity is set at 85%. In certain embodiments, the present machine learning methods are able to classify individuals having a likelihood of cancer with at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% sensitivity when the specificity is set at 90%.

In some embodiments, the neural net comprises one hidden layer, two hidden layers, three hidden layers, four hidden layers, or five hidden layers. Neural nets may contain any number of nodes, e.g., between 1 and 1000 nodes, between 1 and 500 nodes, between 1 and 400 nodes, between 1 and 300 nodes, between 1 and 200 nodes, between 1 and 100 nodes, between 1 and 50 nodes, between 5 to 50, between 10 and 40 nodes, between 20 and 30 nodes, between, 5 to 50 nodes, between 5 to 45 nodes, between 10 to 40 nodes, between 15 to 35 nodes, between 20 to 30 nodes, or any combination thereof. In some embodiments, nodes may be evenly distributed, with each hidden layer receiving the same or about the same number of nodes. In other embodiments, nodes may be unevenly distributed, e.g., with the first hidden layer receiving fewer nodes than the second hidden layer or with the first hidden layer receiving more nodes than the second hidden layer.

In illustrative embodiments, the neural net comprises two hidden layers. See FIG. 13. The first hidden layer may comprise 2 to 20 nodes and the second layer may comprise 15 to 35 nodes. The first hidden layer may comprise 2 to 10 nodes and the second layer may comprise 15 to 25 nodes. In illustrative embodiments, the first hidden layer has 5 nodes and the second hidden layer has 20 nodes. See FIG. 15D and Example 4. In other embodiments, the first hidden layer may comprise 15 to 35 nodes and the second layer may comprise 2 to 20 nodes. In other embodiments, the first hidden layer may comprise 15 to 25 nodes and the second layer may comprise 2 to 10 nodes. In other embodiments, the neural net has a total of 20 to 30 nodes.

Neural networks have the capability of detecting complex nonlinear relationships between variables, to determine which variables are the most predictive among a set of variables, and can discover relationships between variables that were not previously known. For example, one of skill in the art may determine which groups of biomarkers in combination with specific clinical features are the most predictive of a likelihood of having lung cancer. For example, an ANN may be used to determine that a subset of 6 biomarkers and a subset of 5 clinical features are highly predictive, e.g., 90% or greater sensitivity at 80% specificity, to identify individuals with an increased likelihood of having cancer.

In illustrative embodiments, the following biomarkers CEA, NSE, CYFRA 21-1, CA19-9, Pro-GRP and SCC are evaluated using a neural net with the following clinical features: smoking status, package year, patient age, family history of lung cancer, and symptoms.

In some embodiments, neural nets may be used to determine which inputs of a plurality of inputs are the most important for accurately identifying patients that are likely to have lung cancer. For instance, starting with a large number of inputs, the neural net can identify which subset, e.g., which 5 to 15 inputs of a larger group of inputs are the most predictive. This approach can help reduce costs in screening as well as simplify computation, as not every biomarker or clinical factor linked to lung cancer needs to be tested, but rather, only the most predictive inputs. See Example 6 and Table B, for a ranking of biomarkers and clinical factors for lung cancer.

Thus, present invention embodiments encompass neural net approaches to determining which subset of biomarkers combined with which subset of clinical factors and optionally other factors are the most predictive. In some embodiments, the neural net may be used to determine a total of three factors (e.g., at least two biomarkers and at least one clinical factor) that is highly predictive of the likelihood of lung cancer. In other embodiments, the neural net may be used to determine a total of four factors (e.g., at least two biomarkers and at least one clinical factor) that is highly predictive of the likelihood of lung cancer. In other embodiments, the neural net may be used to determine a total of five factors (e.g., at least two biomarkers and at least one clinical factor) that is highly predictive of the likelihood of lung cancer. In other embodiments, the neural net may be used to determine a total of six factors (e.g., at least two biomarkers and at least one clinical factor) that is highly predictive of the likelihood of lung cancer. In other embodiments, the neural net may be used to determine a total of seven factors (e.g., at least two biomarkers and at least one clinical factor) that is highly predictive of the likelihood of lung cancer. In other embodiments, the neural net may be used to determine a total of eight factors (e.g., at least two biomarkers and at least one clinical factor) that is highly predictive of the likelihood of lung cancer. In other embodiments, the neural net may be used to determine a total of nine factors (e.g., at least two biomarkers and at least one clinical factor) that is highly predictive of the likelihood of lung cancer. In other embodiments, the neural net may be used to determine a total of ten factors (e.g., at least two biomarkers and at least one clinical factor) that is highly predictive of the likelihood of lung cancer. In other embodiments, the neural net may be used to determine a total of eleven factors (e.g., at least two biomarkers and at least one clinical factor) that is highly predictive of the likelihood of lung cancer. In other embodiments, the neural net may be used to determine a total of twelve factors (e.g., at least two biomarkers and at least one clinical factor) that is highly predictive of the likelihood of lung cancer. In general, highly predictive indicates that the neural net is able to identify patients likely to have lung cancer, with at least an 75% sensitivity, at least an 85% sensitivity, and at least a 90% sensitivity (at 80% specificity) or greater. Thus, the neural net may be used to optimize the subset of inputs from the total number of possible inputs, in order to determine which subset—which of the biomarkers, clinical factors, or any other inputs to the neural network as disclosed herein—are the most predictive of the likelihood of having lung cancer.

In some embodiments, the neural net can be used to identify novel predictors of a disease. For example, a novel biomarker or clinical factor or other type of input as disclosed in this application (e.g., from the literature, from the environment, etc.) may be selected as an input into a neural net, and it can be determined whether this input is predictive of lung cancer. In some cases, the input may have no known previous association with lung cancer. See Example 7.

In some embodiments, the neural net can be used to rank inputs for a disease, to identify which inputs are the most predictive of a disease among a larger population/group of inputs.

In some embodiments, inputs may be selected in order to improve the performance of the neural net. For example, rather than picking the set of inputs that achieves the highest possible sensitivity with a clinically relevant specificity such as 80% or greater, the inputs are selected to reach a sensitivity threshold (e.g., 80% or greater), and once reaching this threshold, the inputs are selected to optimize performance of the neural net, thereby improving the performance of the neural net.

Accordingly, systems, methods and computer readable media are presented herein regarding using a machine learning system, e.g., a neural net, to identify a patient's risk of having cancer. A set of data comprising a plurality of patient records, each patient record including a plurality of parameters and corresponding values for a patient, and wherein the set of data also includes a diagnostic indicator indicating whether or not the patient has been diagnosed with cancer is stored in a memory, accessible by the neural net or machine learning system. The plurality of parameters includes various biomarkers, clinical factors and other factors which may be selected as inputs into the neural net system. The diagnostic indicator is an affirmative indicator that the patient has cancer, e.g., a lung X-ray and/or biopsy confirming a diagnosis of cancer. A subset of the plurality of parameters is selected for inputs into the machine learning system, wherein the subset includes a panel of at least two different biomarkers and at least one clinical parameter.

In order to train the machine learning system, the set of data (e.g. retrospective) is randomly partitioned into training data and validation data. A classifier is generated using the machine learning system based on the training data, the subset of inputs and other parameters associated with the machine learning system as described herein. It is determined whether the classifier meets a predetermined Receiver Operator Characteristic (ROC) statistic, specifying a sensitivity and a specificity, for correct classification of patients. In embodiments, the specificity is at least 80% and the sensitivity is at least 75%.

When the classifier does not meet the predetermined ROC statistic, the classifier may be iteratively regenerated based on the training data and a different subset of inputs until the classifier meets the pre-determined ROC statistic. When the machine learning system meets the predetermined ROC statistic, a static configuration of the classifier may be generated. This static configuration may be deployed to a physician's office for use in identifying patients at risk of having lung cancer or stored on a remote server that can be accesses by the physician's office.

Once the neural net has been trained on the training data, the neural net may be validated using the validation data. The validation data also includes a plurality of parameters and corresponding values for a patient, and includes a diagnostic indicator indicating whether or not the patient has been diagnosed with cancer. The validation data may be classified using the classifier, and it may be determined whether the classifier meets the predetermined ROC statistic based on this data. When the classifier does not meet the predetermined ROC statistic, the classifier may be iteratively regenerated based on the training data and a different subset of the plurality of parameters, until the regenerated classifier meets the predetermined ROC statistic. The validation process may then be repeated.

A user, with access to a computing device with the static classifier, may enter values corresponding to a patient into the computing device. The patient may then be classified, using the static classifier, into a category indicative of a likelihood of having cancer or into another category indicative of a likelihood of not having cancer. The system may then send a notification to the user (e.g., a physician) recommending additional diagnostic testing (e.g., a CT scan, a chest x-ray or biopsy) when the patient is classified into the category indicative of a likelihood of having cancer.

In some embodiments, the machine learning system, e.g., the neural net, may be continuously trained over time. Test results obtained from the diagnostic testing, which confirm or deny the presence of cancer, may be incorporated into the training data set for further training of the machine learning system, and to generate an improved classifier by the machine learning system.

In general, a classifier may include but is not limited to a support vector machine, a decision tree, a random forest, a neural network, or a deep learning neural network.

Thus, in some embodiments, the values of a panel of biomarkers in a sample from a patient are measured. A classifier is generated by a machine learning system to classify the patient into a category indicative of a likelihood of having cancer or into another category indicative of a likelihood of not having cancer, wherein the classifier comprises a sensitivity of at least 70% and a specificity of at least 80%, and wherein the classifier is generated using the panel of biomarkers comprising at least two different biomarkers, and at least one clinical parameter. When a patient is classified into a category indicating a likelihood of having cancer, a notification to a user for diagnostic testing is provided. In embodiments, the category indicative of a likelihood of having cancer may be further categorized into qualitative groups (e.g. high, low, medium, etc.) for the likelihood of having cancer, or into quantitative groups (e.g. a percentage, multiplier, risk score, composite score) of the likelihood of having cancer.

In other embodiments, a computer implemented method for predicting a likelihood of cancer in a subject, using a computer system having one or more processors coupled to a memory storing one or more computer readable instructions for execution by the one or more processors, the one or more computer readable instructions comprising instructions for: storing a set of data comprising a plurality of patient records, each patient record including a plurality of parameters for a patient, and wherein the set of data also includes a diagnostic indicator indicating whether or not the patient has been diagnosed with cancer; selecting a plurality of parameters for inputs into a machine learning system, wherein the parameters include a panel of at least two different biomarker values and at least one type of clinical data; and generating a classifier using the machine learning system, wherein the classifier comprises a sensitivity of at least 70% and a specificity of at least 80%, and wherein the classifier is based on a subset of the inputs.

Given the myriad of factors associated with the development of cancer, present invention embodiments utilize artificial intelligence/machine learning systems, e.g., neural networks, for providing an improved, more accurate determination of an individual's likelihood (risk) of having cancer. By providing the neural network system with a myriad of risk factors associated with the presence of cancer, some of which have a greater impact than others, as well as a sufficiently large training data set, the neural network may more accurately predict an individual's likelihood (risk) of having cancer, offering patients and clinicians a strong, evidenced-based individualized risk assessment, with specific follow-up recommendations for patients identified as high-risk. Machine learning systems offer the ability to determine which of the myriad of risk factors are most important, as well as how to weight such factors. In addition, machine learning systems can evolve over time, as more data becomes available, to make even more accurate predictions.

In some embodiments, although the machine learning system can evolve over time to make more accurate predictions, the machine learning system may have the capability to deploy improved predictions on a scheduled basis. In other words, the techniques used by the machine learning system to determine risk may remain static for a period of time, allowing consistency with regard to determination of a risk score. At a specified time, the machine learning system may deploy updated techniques that incorporate analysis of new data to produce an improved risk score. Thus, the machine learning systems described herein may operate: (1) in a static manner; (2) in a semi-static manner, in which the classifier is updated according to a prescribed schedule (e.g., at a specific time); or (3) in a continuous manner, being updated as new data is available.

While example embodiments presented herein refer to neural networks, present invention embodiments are not intended to be limited to neural networks and may apply to any type of machine learning system. Thus, it is expressly understood that the embodiments presented herein are not intended to be limited strictly to neural networks, but may include any form of artificial intelligence system of any type or of any combination having the functionality described herein.

Figure 1B:
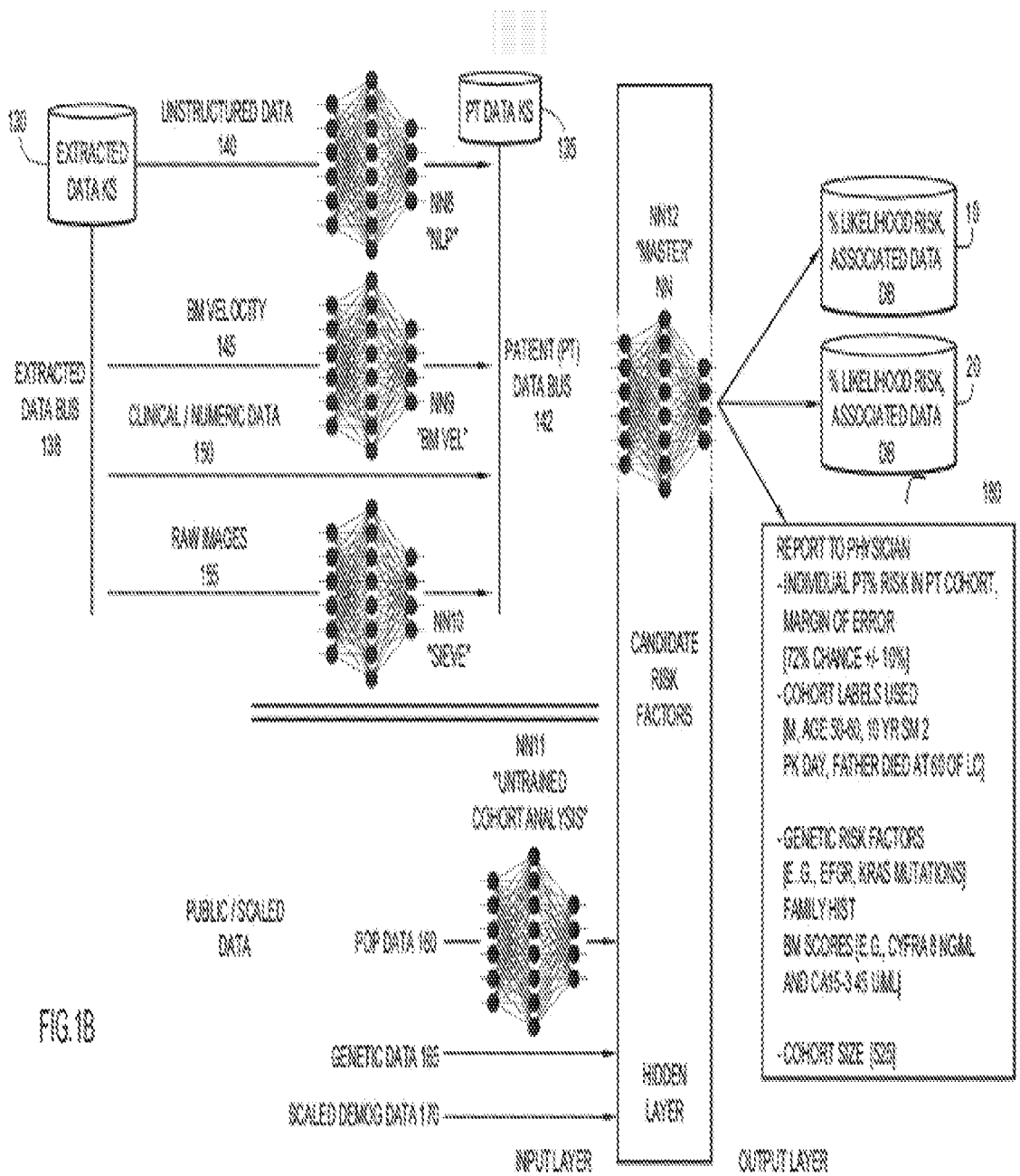

FIGS. 1A-1B are schematic diagrams of an example computing environment in accordance with present invention embodiments. An example artificial intelligence computing system, also referred to as Neural Analysis of Cancer System (NACS) 100, for determining a risk of having cancer is shown. In summary, data from a patient's medical records and other publically available data is provided to a master neural net, wherein the master neural net analyzes the data to predict a patient's individual risk of having cancer, relative to a cohort population.

In some embodiments, a plurality of other neural nets are utilized to provide data to the master neural net in a form conducive for analysis. However, it is expressly understood that while NACS 100 may comprise a plurality of other neural nets (e.g., for data cleaning, for data extraction, etc.) for providing the data in a suitable form, present invention embodiments also include providing data to the master neural net in a predefined form suitable for analysis without additional processing by other neural nets. Thus, present invention embodiments include the master neural net, as well as the master neural net in combination with any one or more other neural nets for data handling.

FIG. 1A comprises one or more neural nets NN 1-7, one or more databases db 10-60, public bus 65 and scaled bus 70, HIPPA Redaction and Anonymizer 75 as well as one or more knowledge stores (KS) 80, 110 and 120. In general, each database 10-60 includes one or more types of information associated with a risk of having cancer. In some embodiments, this information may be distributed across a plurality of databases, while in other embodiments, the information may be included in a single database. Each database may be local to or remote from each of the other databases, and each neural net may be local to or remote from each of the databases. Each component of FIG. 1A is described in additional detail as follows.

Primary EMR db 10 may be an electronic medical record (EMR) database, e.g., at a hospital, physician's office, etc., comprising one or more medical records for one or more patients. Importantly EMR db 10 will supply the biomarker levels or values of at least the patient's most resent blood test. In other embodiments EMR may also provide the historical biomarker data from the patient, if serial testing was conducted and the information is available, to permit biomarker velocity to be factored into the algorithm. In some embodiments, this database is a primary source of medical information (e.g., a patient's primary care physician, hospital, specialist, or any other source of primary care, etc.) for a particular patient. Secondary EMR db 20 may be an EMR database (e.g., at another hospital, at another physician's office) comprising medical records for a family member related to the patient or comprising additional medical records for the patient not found in primary EMR db 10). In some aspects, secondary EMR database 20 may comprise more than one database. In general, EMR databases may comprise patient medical records, including one or more of the following types of information (e.g., age, gender, address, medical history, physician notes, symptoms, prescribed medications, known allergies, imaging data and corresponding annotations, treatment and treatment outcomes, blood work, genetic testing, expression profiles, family histories, etc.).

In some embodiments, a first neural net (also referred to as NN1 "Adder") may be used for determining whether additional family member information or patient information is available in secondary EMR db 20. In the event that additional information is available, secondary EMR db 20 may be queried for this information.

A second neural net (also referred to as NN2a "Cleaner" or NN2b "Cleaner") is used to identify missing, ambiguous or incorrect medical data (collectively referred to as "problematic data") pertaining to the patient. For example, neural net NN2a may be used to identify problematic data from primary EMR database db 10, and neural net NN2b may be used to identify problematic data from secondary EMR database db 20. In some embodiments, problematic data is remedied by obtaining the information as part of an outreach process through which other sources of information are utilized to remedy the problematic data. For example, a medical provider, the patient, or a family member may be contacted via telephone, electronic mail or any other suitable means of communication to resolve issues with problematic data. Alternatively, other EMR databases, other sources of electronic information, etc., may be accessed to remedy the problematic data.

In some embodiments, the identified problematic data may be ranked according to potential impact to the determination of the risk score, such that the identified problematic data having a larger impact on the risk score is ranked as more important, in order to effectively allocate resources. For example, a missing zip code may have less of a potential impact on the risk score, and may therefore be tolerated, than errors in smoking history or lab tests, which would have a larger potential impact.

Clean data is sent to HIPPA Redaction and Anonymizer module 75, which anonymizes data to comply with regulatory and other legal requirements. Unless otherwise authorized by the individual, individual health care records are usually anonymized in order to comply with privacy and other regulations. In some embodiments, the individual records are anonymized by replacing patient specific identification information (e.g., a name, social security number, etc.) with a unique identifier, providing a way to identify the individual after the risk score has been determined.

Once the data has been cleaned, and has been anonymized by HIPPA Redaction and Anonymizer 75, it may be stored in clean data knowledge store (KS) 80, a repository generated by NACS 100. In some embodiments, once the problematic data has been remedied, the corrected data may be stored in the primary EMR db 10 or the secondary EMR db 20 itself, and therefore, a separate knowledge base repository may not be needed.

A third neural net (also referred to as neural net NN3 "EMR Extractor" may be used for extracting specific relevant information from clean data KS 80, which includes clean data from a patient's medical records. Neural net NN3 is trained to identify electronic medical records data that are relevant for determining a risk score. For example, by providing a sufficiently large number of training data sets in which known medical data of specified types are presented to the neural net, and by progressing through an iterative process in which potential medical data identified by the neural net is marked as correct or incorrect with regard to the known type, the neural net can be trained to learn to identify specific medical data (e.g., images, unstructured, structured, etc.). Neural net NN3 may classify the data into different data types, e.g., raw images, numeric/structured data, BM velocity, unstructured data, etc., and the data may be stored in an extracted data knowledge store (KS) 130 (see FIG. 1B).

NN3 may separate the identified patient data into different categories of information, e.g., raw images, unstructured data (e.g., physician notes, diagnosis, treatments, radiological notes, etc.), numerical data (e.g., blood test results, biomarkers), demographic data (age, weight, etc.) and biomarker velocity. Some types of data are subject to further processing, e.g., by another neural net, while others are sent to NN12 (referred to as the "master" NN) for processing.

In other embodiments, a fourth neural net (also referred to as NN4 "Puller" may be used for identifying relevant or requested data in databases db 30-60, which is relevant to the patient's medical history. Examples of publically available databases include environmental databases 30, employment databases 40, population databases 50, and genetic databases 60. In general, this neural net may be used to identify publically available data (e.g., data stored in databases, data in journal articles, publications, etc.) having information regarding risk factors for having cancer, and pertinent to a patient's medical history.

Examples of the types of information that may be extracted from the EMR dbs 10 and 20, to be provided to neural net NN4 for further analysis are provided herein. For the environmental database db 30, the following fields may be identified: patient location, work zip code, years at the address. For the occupational/employment database db 40, the number of years in a particular employment may be identified. For the population database db 50, patient demographics such as gender, age, number of years as a smoker, and family history may be identified. For the genetic database db 60, mutations such as BRAF V600E mutation, EGFP Pos may be identified. This information may be provided to neural net NN4, and corresponding questions may be generated to determined relevant risk factors.

For example, NACS 100 may identify an occupation of an individual, and generate a question to be asked to database db 40 regarding whether that individual's occupation has a known association with cancer. A patient may have lived in a particular zip code for a determined number (e.g., 10) of years. Accordingly, a corresponding question of "What is the cancer risk for a patient living in that particular zip code for the past 10 years?" could be generated and stored in public knowledge store (KS) 110, to be asked at a subsequent point in time. As another example, NACS 100 may generate a question to be asked to environment db 30 regarding whether an individual's occupation is associated with an increased risk of cancer. A patient may have spent a number of years (e.g., 20) employed in a certain profession (e.g., coal miner). Accordingly, the corresponding question of "What is the cancer risk for working as a coal miner for 20 years?" could be generated and stored in public KS 110, to be asked at a subsequent point in time. Similarly, NACS 100 may also generate genetic questions, e.g., whether a mutation or other genetic abnormality from a patient's medical history has been implicated in the occurrence of cancer. In general, various types of environmental, employment, population and genetic based questions may be generated and stored in public KS 110 as questions to be asked, e.g., with the assistance of a question-answer generation module, which are known in the art.

Public bus 65, also shown in FIG. 1A, provides a communication network with which to provide questions related to a patient's medical history to publically available databases, wherein the answers to the questions may be incorporated into the determination of the risk score. For example, information may be transmitted between public knowledge store (KS) 110, which may comprise questions generated by NACS 100 that are to be asked to the databases, and the databases db 30-60 themselves.

As previously indicated, publically available databases db 30-60 may comprise various types of information associated with a risk of having cancer. Accordingly, present invention embodiments may utilize one or more of these databases, in addition to the information from electronic medical records db 10 and 20 an other information, to determine a likelihood for the presence of cancer for an individual.

For example, environment database db 30 may comprise environmental or geographical factors associated with the presence of cancer. For example, certain geographical zip codes may indicate environmental factors, e.g., presence of a carcinogen within a given area, radioactive elements, toxins, chemical spills or contamination, etc., associated with an increased risk of having cancer. Database db 30 may also comprise information regarding environmental factors associated with the development of a disease such as cancer, e.g., smog levels, pollution levels, exposure to secondhand smoke, etc.

Employment database db 40 may comprise information linking some types of employment to an increased risk of having cancer. For example, certain industries and job types, e.g., coal miner, construction workers, painters, industrial manufacturers, etc., may have an increased likelihood of exposure to radiation or cancer-causing chemicals, including asbestos, lead, etc., which increases the risk for having cancer.

Population database db 50 comprises information, usually anonymized, for a population of individuals having a diagnosis of cancer. In some embodiments, database db 50 may include profiles for individual patients, each patient profile including various types of information, e.g., age, gender, smoking history in years and number of packs per day, imaging data, employment, residence, biomarker scores, biomarker composite scores, or biomarker velocities, etc., that may influence an individual's risk of having cancer. By collecting and analyzing this type of data, cohort populations may be determined by a neural net.

Genetic db 60 may include genes identified as being associated with an increased risk of having cancer. For example, genetic db 60 may include any publically available database or repository, as well as journal articles, research studies, or any other source of information that links a particular genetic sequence, mutation, or expression level to an increased risk of having cancer.

Any of databases 30-60 may comprise a plurality of databases. For example, environment db 30 may comprise a plurality of databases, each database including a different type of environmental information, employment db 40 may comprise a plurality of databases, each database including a different type of employment information, population db 50 may comprise a plurality of databases, each database comprising population information, and genetic db 60 may comprise a plurality of databases, each database comprising a different type of genetic information.

Information may be transmitted between databases db 30-60 and stored in scaled knowledge store (KS) 120 via scaled bus 70. For example, scaled KS 120 may comprise answers to the questions generated by NACS 100 that were asked to databases dbs 30-60. Both public KS 110 and scaled KS 120 are repositories that are created by NACS.

To facilitate asking questions to dbs 30-60, a fifth set of neural nets (also referred to as NN5a, NN5b, NN5c, or NN5*d*) are used for identifying specific data in a specific subject matter knowledge source or database (e.g., dbs 30-60). For example, neural net NN5*a* may be utilized to identify specific environmental data in environment db 30, neural net NN5*b* may be utilized to identify specific employment data in employment db 40, neural net NN5*c* may be utilized to identify specific population data in population db 50, and neural net NN5*d* may be utilized to identify specific genetic data in genetic db 60. Knowledge sources or databases considered to be leading sources of information in a specific field may be selected for inclusion with dbs 30-60. Examples of knowledge sources include journal articles, databases, presentations, gene sequence or gene expression repositories, etc. In some aspects, each category of information or each source of information itself may have a corresponding neural net for identifying relevant data, and in some embodiments, the neural net may be trained to recognize information in a vendor-specific manner. Each database also may comprise both structured and unstructured data.

In some embodiments, if a new study reports a new genetic link to cancer, or a new geographical "hotspot" for the occurrence of cancer, the NACS system 100 could search information in databases 30-60 to reevaluate its determined risk and provide an updated risk to a patient or physician. For example, a question could be generated and stored in public KS 110, which would be asked to dbs 30-60 at predefined intervals (e.g., monthly, quarterly, annually, etc.), and the risk determination could be updated periodically.

In the medical domain, new clinical literature and guidelines are continuously being published, describing new screening procedures, therapies, and treatment complications. As new information becomes available, queries may be automatically run by a question-answer generation module without active involvement (in an automated manner). The results may be proactively sent to the physician or patient or stored in scaled KS 120 for subsequent use.

In some embodiments, NACS 100 can automatically generate queries from the semantic concepts, relations, and data extracted from dbs 10 and 20, using, e.g., a question-answer module. Using semantic concepts and relations, queries for the question-answering system can be automatically formulated. Alternatively, it is also possible for a physician or patient to enter queries in natural language or other ways, through a suitable user interface.

In still other embodiments, a sixth set of neural nets (also referred to as NN6*a*, NN6*b*, NN6*c*, or NN6*d*) is used to scale each database output, or answer to a question from dbs 30-60 from, e.g., a 0 to 9 range for weighting. For example, the output zip code of 14304 for the Love Canal, NY might be scaled as '9' to indicate high risk, whereas the output zip code of 86336 for Sedona, AZ may be a 'O' to indicate low risk. Many different types of scaling are covered by embodiments of the invention. In some embodiments, database outputs are scaled according to a common reference, regardless of the database, while in other embodiments, database outputs are scaled on a relative basis, e.g., such that a weighting of '9' for a given database may not have the same impact as a weighing of '9' for another database. Depending upon the disparity of the data, each database may have its own corresponding neural net to scale relevant information.

In some embodiments, each answer is generated along with confidences and sources of information. The confidence of each answer can, for example, be a number between 0 and 1. 0 and 10, or any desired range.

In still other embodiments, a seventh neural net (also referred to as NN7 "Gene Snip" is used to identify similar and/or related genes with reference to the genes associated with the patient's medical history. Similar or related genes may be identified on the basis of literature, public databases of genetic information, etc. The neural net NN7 may also output the types of genes that are relevant for further analysis, in addition to the risks associated with the identified gene.

According to the example computing environment shown in FIG. 1A, extracted data from neural net NN3 is sent to other neural nets for analysis via extracted data bus 138. Output data from the external databases db 30-60, which may be stored in scaled KS 120, is loaded onto scaled bus 70 and provided to another neural net for analysis as scaled demographic data 170. Data from neural net NN7 is provided to another neural net for analysis as genetic data 165, and population data 160 is provided as input to other neural nets. Each of these outputs are shown with reference to FIG. 1B.

As shown in FIG. 1B, data from extracted data bus 138 may be classified into different types of data. Data may be classified as raw images 155 (e.g., X-rays, CT scans, MRI, ultrasounds, EEG, EKG, etc.), and the raw images may be provided to NN10 for further analysis as described herein. Data may also be classified into biomarker (BM) velocity data 145, and this data may be provided to neural net NN9 for further analysis as described herein. Data may be further classified into numeric data 150, e.g., age, ICD, blood/biomarker tests, smoking history (years and packs per day), diagnosis (Dx), gender, etc. or unstructured data 140. Unstructured data 140 may include text or numeric based information, e.g., physician notes, annotations, etc. NN8 may analyze unstructured data 140 as described herein using Natural Language Processing and other well established techniques.

An eighth neural net (also referred to as neural net NN8 Natural Language Processing ("NLP") is utilized to analyze unstructured data 140, e.g., physician notes, other EMT text (e.g., radiology, history of present illness (HPI)). After processing by neural net NN8, the data may be separated into multiple categories including a text-based category, including lab reports, progress notes, impressions, patient histories, etc., as well as derived data, which includes data derived from the text-based data, e.g., years of smoking and frequency of smoking (e.g., how many packs a day).

In other embodiments, a ninth neural net (also referred to as NN9) is utilized to analyze biomarker (BM) velocity. This neural net, which may be trained in a supervised or unsupervised manner, analyzes the velocity of biomarkers of a biomarker panel and determines whether the velocity is indicative of the presence of cancer. Markers may include CYFRA, CEA, ProGrp, etc., and the neural net may analyze both the absolute value and relative value as a function of time. In some aspects, having a velocity above a threshold value may be indicative of the presence of cancer. Individual as well as group velocity scores for a combination of biomarkers may be generated. In some embodiments, this neural net may be untrained, and may identify previously unknown associations. Individual as well as group velocities may be determined for panels.

In other embodiments, a tenth neural net (also referred to as NN10 "Sieve") is utilized to analyze raw images, e.g., XRAYs, CT scans, MRIs, etc., and extract clinical imaging data. In some embodiments, this neural net NN10 may extract portions of images relevant to determining an increased risk of cancer.

In other embodiments, an eleventh neural net (also referred to as neural net NN11 "Untrained Cohort Analysis") is utilized to identify patterns in cohort groupings. A particular cohort grouping may change as a function of time based upon the decisions made by the neural net NN11. For example, age correlates with risk of developing cancer, but the optimal grouping (e.g., ages 42-47, 53-60, etc.) is not known. The neural net NN11 may initially determine that a cohort population of ages 53-60 with a smoking history of ten years carries an increased risk of 50%. The optimal grouping (cohort) may change as additional data becomes available. By utilizing an untrained neural net, such as neural net NN11, to discover naturally occurring grouping patterns (e.g., a cluster of individuals developing cancer at a given age and based on a similar smoking history), the grouping patterns may be identified and analyzed to determine an optimal cohort for a given patient. In some embodiments, NN11 is untrained and will be self taught. For example, age is an important factor. The best age range or grouping may not be known, e.g., whether the age range should be 42-47, 53-60, and so forth. Moreover, the grouping may change as other risk factors are integrated into the analysis. By analyzing the data using an untrained NN, the NN may utilize clustering to find relevant groupings. The algorithm may iteratively try different grouping and different risk factors until finding an optimal cohort for the given patient. In many cases, untrained NN will find associations that would be discovered by traditional techniques.

A twelfth neural net (also referred to as neural net NN12 "Master NN") receives a plurality of inputs, each associated with occurrence of a disease, e.g., such as cancer. In this example, NN12 receives inputs of the patient EMR data bus 142, some of which are further processed using neural nets NN8-10 as well as scaled demographic data 170, genetic data 165 and population data 160 after being processed by NN11 to generate cohort data.

Input data to neural net NN12 may be normalized according to the techniques presented herein. Neural net NN12 assigns weights to each input, and performs an analysis to make a prediction (a % likelihood) of having cancer based on these risk factors. Initially, the assigned weights may be determined from training the neural net using a data set that includes patients with a cancer diagnosis, their medical history, and other associated risk factors. As additional data becomes available about risk factors for cancer (e.g., new risk factors, etc.), this data may be integrated into neural net NN12 and the corresponding weighting may evolve as a function of time. The output data of neural net NN12 may be stored in db 10 and/or db 20 as part of a feedback loop.

NN12 is trained to produce the following outputs, as shown at block 180, including patient risk scores (e.g., an individual patient's % risk in a given cohort, margin of error, size of cohort, labels of cohort, etc.), major risk factors identified (may be different from the cohort population), recommended diagnosis (DX) and treatment success factors. Neural net NN 12 may also generate other types of data as described herein.

Neural net NN12 may utilize feedback to write output back to databases db 10 and db 20 for continuous improvement of the machine learning system, allowing the machine learning system to make more accurate predictions by continually incorporating new data into the training set. As new patient data becomes available, e.g., confirming or denying that the patient has cancer, NACS system 100 may utilize this information for additional intrinsic training, allowing the determined % risk score to improve in accuracy. For example, if the patient is diagnosed with cancer, then types of treatments, outcomes (longevity) and success rates may be complied, and fed back into the system, allowing the system to be trained on successful treatments and best (positive) clinical indicators with the best sensitivity, selectivity, and lowest ambiguity. If the patient is not diagnosed with cancer, then this information is fed back into the system to train for best negative clinical indicators. The physician's diagnosis can be compared with the NACS risk score as well.

Present invention embodiments may include at least one EMR, e.g., db 10, a master neural net NN12 for performing a risk determination, and any one or more of the aforementioned public databases db 30-60, as well as any one or more of the aforementioned knowledge stores 80, 110, 120, 130, and 135, and any one or more of the neural nets NN1-11.

In some embodiments, the neural net may be trained to identify information provided in a vendor-specific format.

In other embodiments, neural net NN12 may determine that insufficient information is present to make a determination regarding a patient's risk score.

Figure 2A:
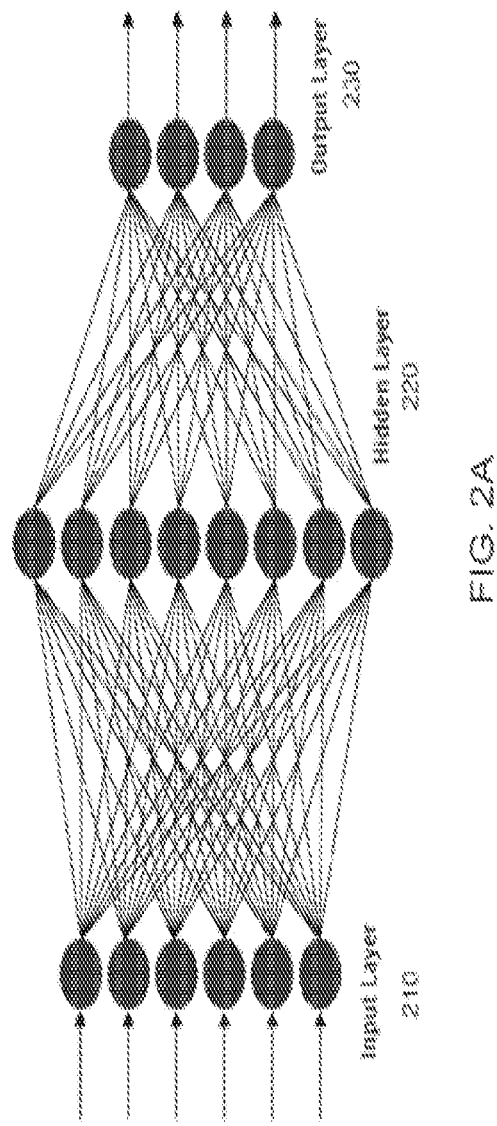
FIGS. 2A-2B are illustrations of example neural net systems, in accordance with example embodiments.

FIG. 2A shows an example of a neural net. As previously indicated, neural net systems generally refer to artificial neural network systems, comprising a plurality of artificial neurons or nodes, such that the system architectures and concepts behind the design of neural net systems are based on biological systems and/or models of neurons.

For example, components of a neural network may include an input layer comprising a plurality of input processing elements or nodes 210, one or more "hidden" layers 220 comprising processing elements or nodes, and an output layer 230 to the hidden layer comprising a plurality of output processing elements or nodes. Each node may be connected to one or more of the other nodes as part of the hidden computational layer. The hidden layer 220 may comprise a single layer or multiple layers, with each layer comprising a plurality of interconnected computational nodes, wherein the nodes of one layer are connected to another layer.

Neural nets may also comprise weighting and aggregations operations as part of the hidden layer. For example, each input may be assigned a respective weight, e.g., a number in a range of 0 to 1, 0 to 10, etc. The weighted inputs may be provided to the hidden layer, and aggregated (e.g., by summing the weighted input signals). In some embodiments, a limiting function is applied to the aggregated signals. Aggregated signals (which may be limited) from the hidden layer may be received by the output layer, and may undergo a second aggregation operation to produce one or more output signals. An output limiting function may also be applied to the aggregated output signals, resulting in a predicted quantity by the neural net. Many different configurations are possible, and these examples are intended to be non-limiting.

Neural net systems may be configured for a specific application, e.g., pattern recognition or data classification, through a learning process referred to as training, as described herein. Thus, neural networks can be trained to extract patterns, detect trends, and perform classifications on complex or imprecise data, often too complex for humans, and in many cases too complex for other computer techniques to analyze.

Figure 2B:
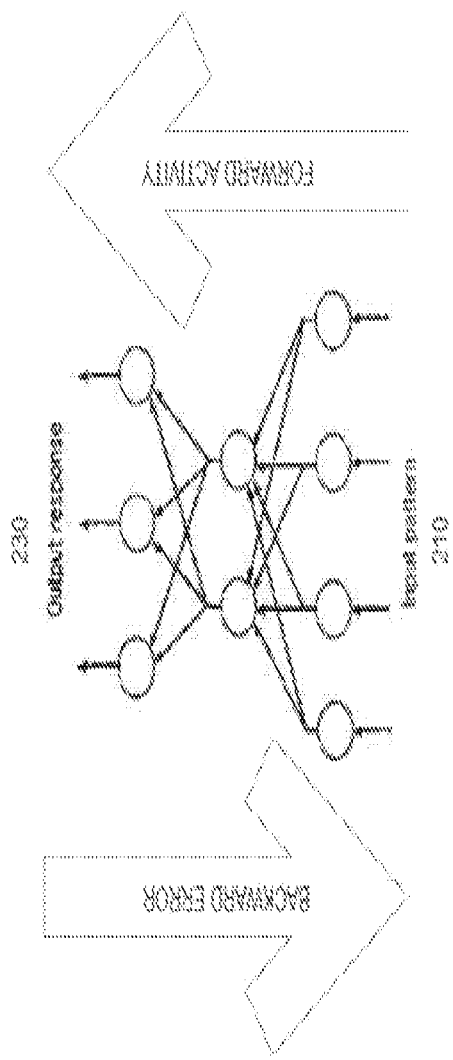

Information within a neural net, as shown in FIG. 2B may also flow bidirectionally. For example, data flowing from the input layer to the output layer is shown as forward activity and the error signal flowing from the output layer to the input layer is represented as feedback or "backpropagation". The error signal may feed back into the system, and as a result, the neural net may adjust the weights of one or more inputs.

Training Neural Nets

Many different techniques for the operation of neural networks are known in the art. Neural nets typically undergo an iterative learning or training process, in which examples are presented to the neural net one at a time, before the neural net is placed in production mode to operate on (non-training) data. In some cases, the same training dataset may be presented to the neural net multiple times, until the neural net converges on a correct solution, reaching specified criteria, e.g., a given confidence interval, a given error, etc. Typically, a set of validation data (e.g., the dataset) is sufficiently large to allow convergence of the neural network, allowing the neural network to be able to predict within a specified margin of error, the correct classification (e.g., increased risk of cancer or no increased risk of cancer) of non-training data. See Example 3.

Training may occur in a supervised or unsupervised manner. In a supervised learning process, a neural net may be provided with a large training data set in which the answers are unambiguously known. For example, the neural net may be presented with test cases from the dataset in a serial manner, along with the answer for the dataset. By providing the neural net with a large dataset comprising both positive and negative answers (e.g., relevant data and non-relevant data) and telling the neural net which data corresponds to positive answers and which to negative answers, the neural net may learn to recognize positive answers (e.g., relevant data) provided that a sufficiently large dataset is provided. In a supervised learning process, an individual or administrator may interact with the machine learning system to provide information regarding whether the result determined by the machine learning system is accurate.

In an unsupervised learning process, a neural net may also be provided with a large training data set. However, in this case, the answers as to which data are positive and which data are negative are not provided to the neural net and may not be known. Rather, the neural net may use statistical means, e.g., K-means clustering, etc., to determine positive data. By providing the neural net with a large dataset comprising both positive and negative answers (e.g., relevant data and non-relevant data), the neural net may learn to recognize patterns in data.

Each input to a neural net is typically weighted. In some embodiments, the initial weighting (e.g., random weighting, etc.) is determined by the machine learning system, while in other cases, the initial weighting may be user-defined. The machine learning system processes the input information with the initial weighting to determine an output. The output may then be compared to the training data set, e.g., experimentally obtained and validated data. The machine learning system may determine an error signal between the computationally obtained prediction and the training data set, and feed or propagate this signal back through the system into the input layer, resulting in adjustment of the input weighting. In other embodiments, the error signal may be used to adjust weights in the hidden layer in order to improve the accuracy of the neural net. Accordingly, during the training process, the neural net may adjust the weighting of the inputs and/or hidden layer during each iteration through the training data set. As the same set of training data may be processed multiple times, the neural net may refine the weights of the inputs until reaching convergence. Typically, the final weights are determined by the machine learning system.

As an example of a training process for neural net NN1, neural net NN1 may be trained to look for indications that secondary EMR db 20 has relevant data. For example, neural net NN1 may be presented with a dataset from EMR system db 20 having the same name and social security number as the patient, along with a confirmation that the patient from the secondary EMR matches the primary EMR. Similarly, the adder may be presented with a data set from another EMR system having the same name and a different social security number as the patient, along with a confirmation that the data from the secondary EMR does not match the patient from the primary EMR. Based on this type of training, the neural net can learn to distinguish which records from which databases match specific patients.

As another example, and with reference to neural nets NN2a and NN2b, these neural nets may be trained to recognize missing data. For example, these neural nets may be presented with a complete dataset for a patient with an indication that the data set is complete. These neural nets may then be presented with another dataset with specified missing data. After a sufficiently large training session, the neural net will learn the concept of missing data, and will be able to identify missing data in a non-training dataset (production mode). Similarly, neural nets NN2a and NN2b may be trained on what constitutes problematic data. For example, if a zip code does not closely match with a populated location field, it is likely wrong, as it is more likely that the patient can correctly identify their city and state.

As yet another example, each neural net NNSa-NN5d is trained, a priori, to find specific data (e.g., from environmental dbs, employment dbs, population dbs, genetic dbs, etc.). Upon meeting specified criteria (e.g., correctly predicting within a specified error rate, which individuals among a population of individuals have cancer), the neural net may be placed in production mode.

Accordingly, for the purposes of the embodiments provided herein, it will be generally assumed that the various neural nets are trained with a data set of sufficient size to reach convergence.

After the neural net is trained, the neural net may be exposed to new data, and its performance may be tested, e.g., with another dataset in which the prediction from the neural net may be validated with clinical data. Once the neural net has been established to behave within established guidelines, the neural net may be exposed to true unknown data.

As neural nets are highly adaptive, the specific criteria used to make decisions to determine a risk score may evolve as a function of time and as new data becomes available. While it may be possible to characterize the neural net as a function of a particular moment in time, the neural net and its corresponding decision making process evolves as a function of time. Accordingly, data flow within the nodes of the network may evolve over time as new data is obtained, and as new conclusions are validated.

Figure 3:
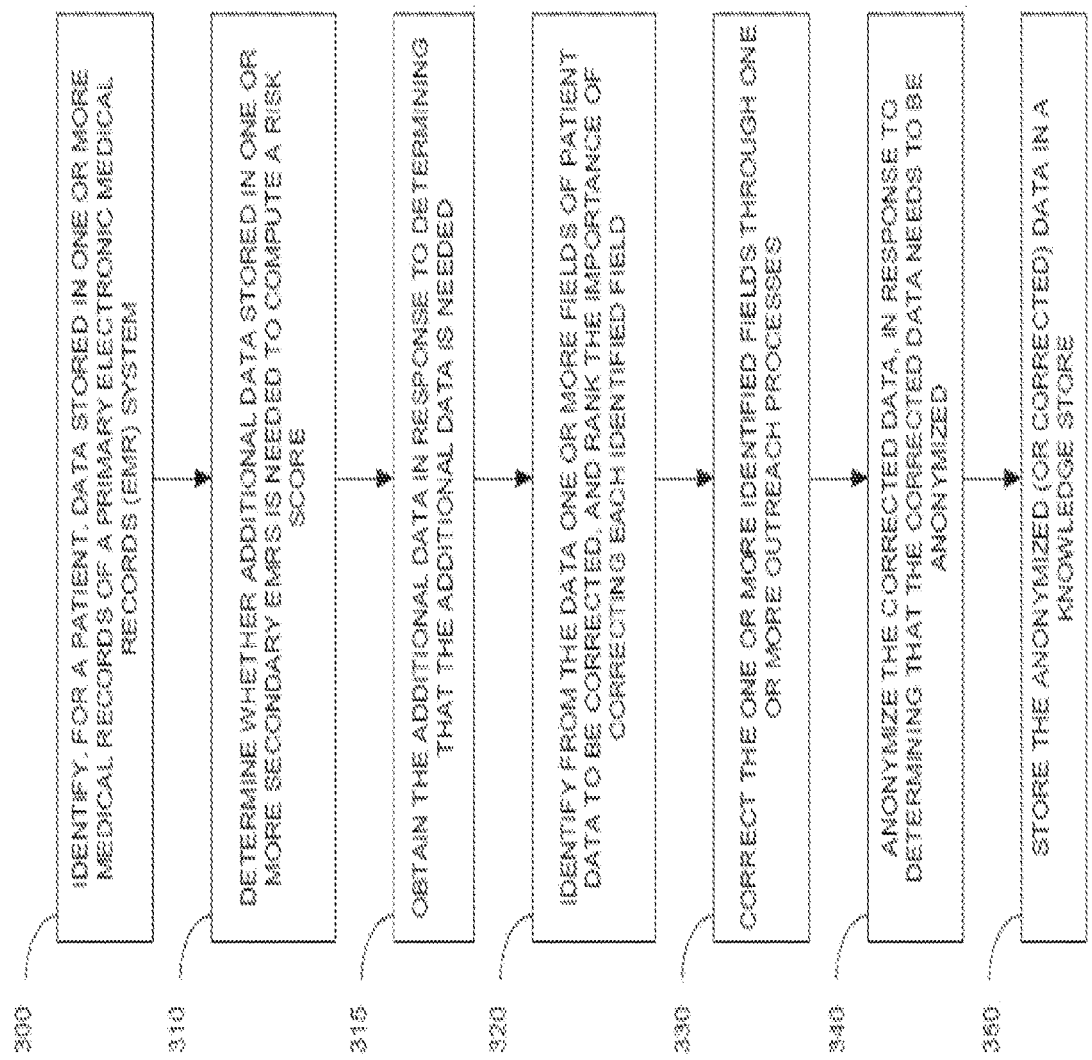
FIG. 3 is a flow diagram illustrating operations for identification and correction of problematic data, in accordance with example embodiments.

FIG. 3 is a flow diagram showing example operations for cleaning information in accordance with an embodiment of the invention. This approach may be utilized to identify patient information in EMR db 10 and EMR db 20, as well as correct problematic information, and store the corrected information in a knowledge store, e.g., clean data KS 80 (see, FIG. 1A). At operation 300, information for a patient that is stored in one or more medical records of a primary Electronic Medical Records (EMR) system is identified. At operation 310, it is determined (e.g., using Adder neural net NN1), whether additional data (e.g., additional medical information from the patient or from family members related to the patient) stored in one or more secondary EMRs is needed to compute a risk score. If the machine learning system can compute the risk score without additional data, the process may continue operation to operation 320. If additional information is needed, at operation 315, the additional data is obtained. At operation 320, the machine learning system identifies (e.g., using neural net NN2a and NN2b), one or more fields of patient data from EMR db 10 and EMR db 20 that is problematic (e.g., missing data, wrong data, ambiguous data, etc.) and is to be corrected. In some embodiments, the problematic data to be corrected is ranked based upon the potential impact of each identified field to the determined risk score. In some embodiments, the highest ranked (highest potential impact) fields are corrected, and the system may determine that the calculation may be performed without correcting fields that have a lower potential impact. At operation 330, the one or more identified fields are corrected through one or more outreach processes (e.g., manually, automatically, or both). An outreach process may include contacting another source of information, such as a physician, a patient, another computing system, etc., in order to correct the problematic data. At operation 340, the machine learning system determines whether the information needs to be anonymized, and if so, the information is anonymized. Otherwise, the process may continue to operation 350. At operation 350, the anonymized (or corrected) information is stored in clean data knowledge store (KS) 80, where it is ready for extraction, e.g., by NN3 "EMR Extractor".

Figure 4A:
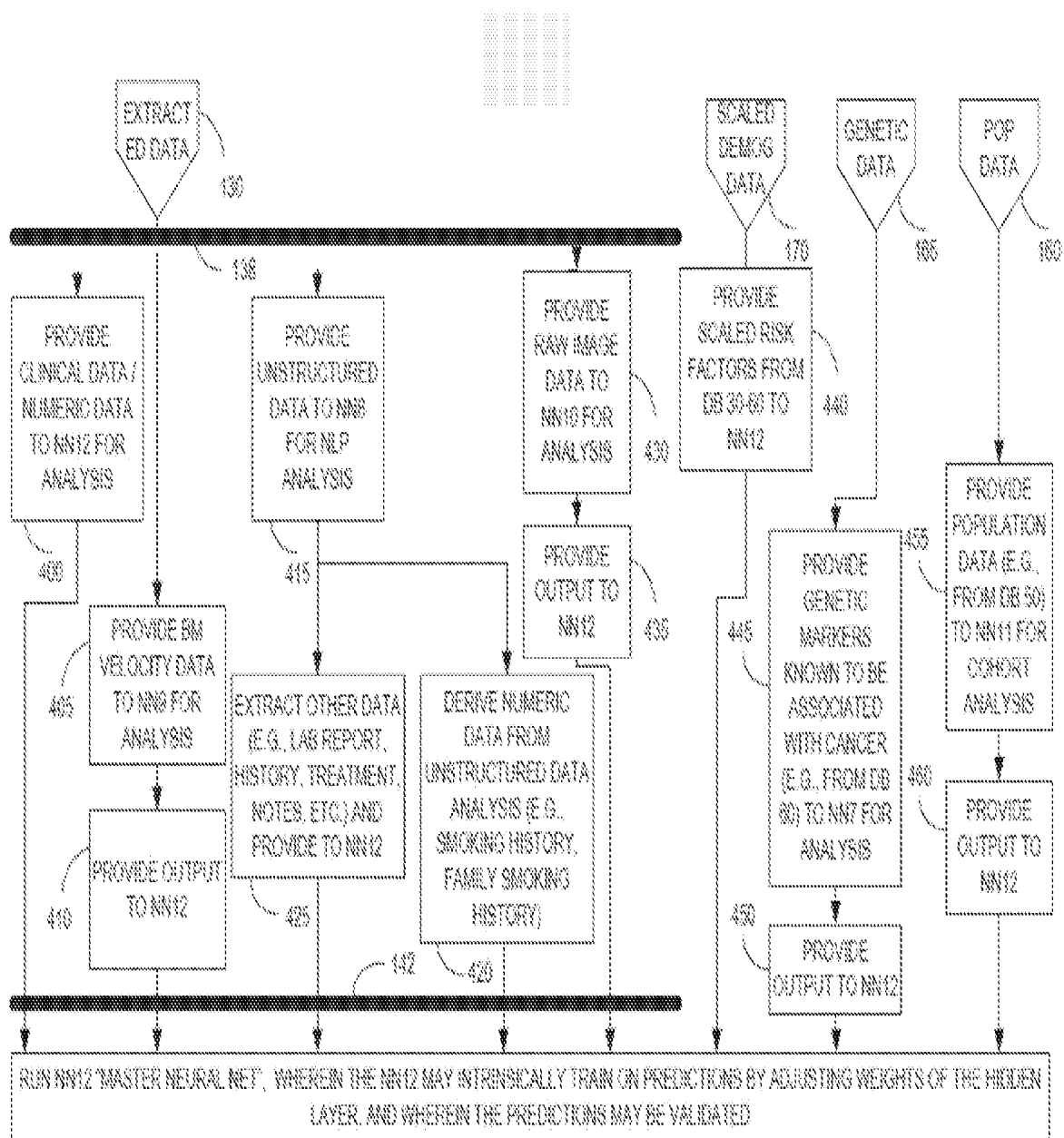
FIGS. 4A-4B are flow diagrams illustrating operations for determining a risk of having cancer, in accordance with example embodiments.
Figure 4B:
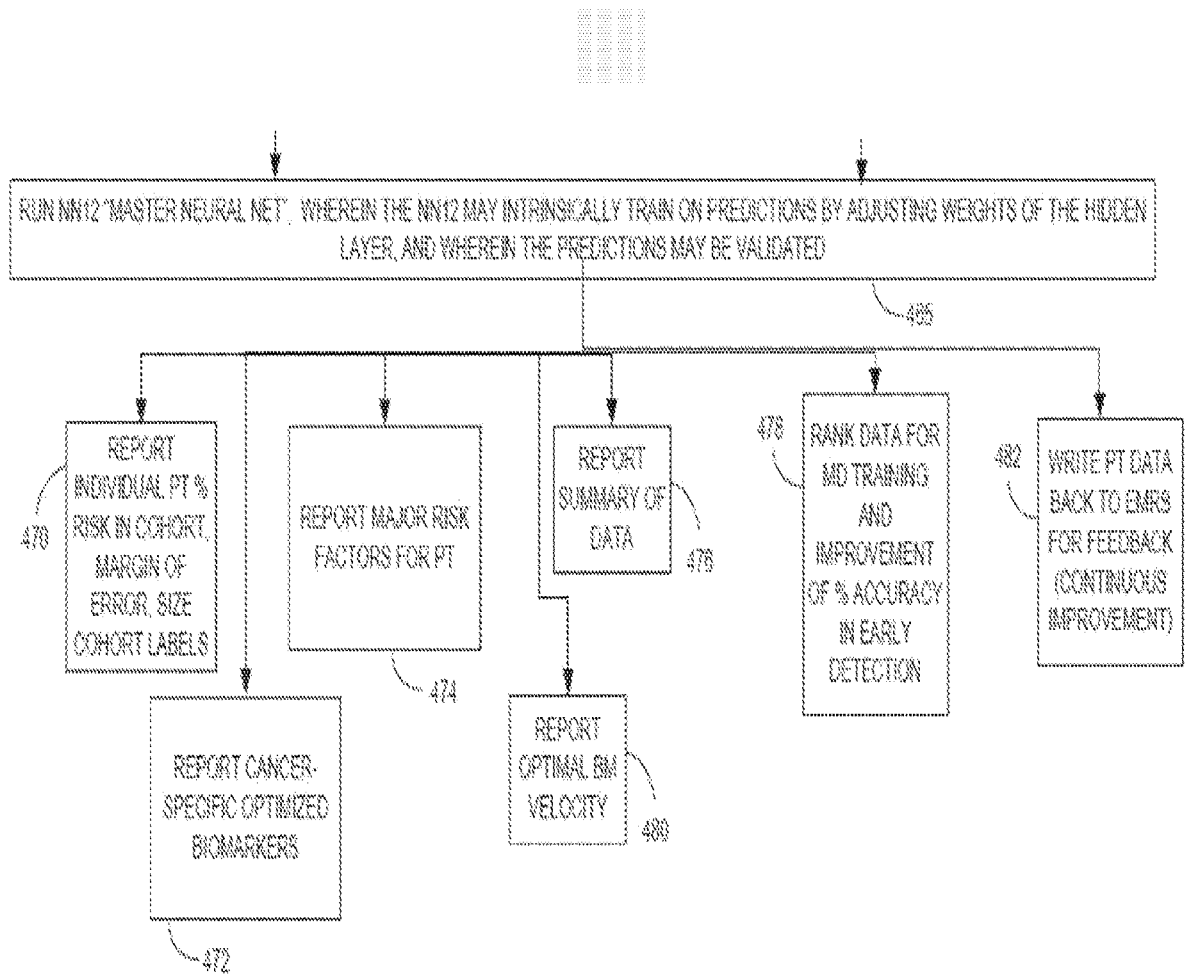

FIG. 4 shows a flow diagram showing example operations involving master neural net NN12, according to embodiments of the invention. In this example, a plurality of inputs are provided to the master neural net NN 12. These inputs include data from the EMR Pt Data Bus 142, as well as from dbs 30-60. The master neural net NN12 analyzes the received inputs to determine an individual's risk for having cancer in a population, e.g., a cohort population.

In this example, data from extracted data KS 130 may be provided to master neural net NN12, either directly or through one or more other neural nets. In particular, at operation 400, numeric data may be provided to NN12 for analysis. In some embodiments, this data may be provided directly to NN12, wherein each type of data may be weighted as a separate input. Other types of data that undergo processing by other neural nets may also be provided to neural net NN12. Biomarker (BM) velocity data that has been processed by neural net NN9 at operation 405 may be provided to neural net NN12 at operation 410 for analysis. NN9 may determine, based on a velocity of biomarker concentration (e.g., a rate of increase of one or more biomarkers as a function of time) that a patient is at increased risk for having cancer. At operation 415, unstructured data is provided to NN8 for analysis. At operations 420 and 425, numeric data derived from unstructured data as well as the unstructured data itself (both outputs of neural net NN8) may be provided to neural net NN12 for processing. At operation 430, raw image data is provided to NN10 for analysis. At operation 435, the output of neural net NN10, analyzed image data may be provided to neural net NN12 for analysis.

In addition to the data from bus 138, master neural net NN12 may also receive inputs from the publically available databases, as shown in operations 440-460. At operation 440, scaled risk factors, from databases dbs 30-60, which may be stored in scaled KS 120 are provided as inputs to master neural net NN12. At operation 445, genetic markers are provided to NN7 for analysis and the output is provided to NN12 for analysis at operation 450. At operation 455, population data in the form of a cohort from neural net NN11 may be generated and provided to neural net NN12 for analysis at operation 460.

The above examples are not intended to be limiting with regard to the types of inputs that may be provided to NN12. Present invention embodiments may include any input derived from a patient's medical information or any source of publically available information related to a patient's medical condition.

Once the inputs are received, master neural net NN12 may be utilized to analyze the information in order to determine whether an individual has an increased risk for having cancer, as shown at operation 465.

In some embodiments, master neural net NN12 may receive a cohort population from neural net NN11. Upon analyzing the different types of data, master NN12 may modify the cohort population to include additional factors. For instance, if a cohort population was originally provided by neural net NN11 as male, 50 years of age, and 10-15 pack years, upon consideration of other risk factors, neural net NN12 may modify the cohort to include additional information, e.g., male, 50 years of age, 10-15 pack years, a composite biomarker score greater than a threshold value (or a category indicative of a likelihood of having, or not having, cancer), and a specified biomarker having a certain velocity. Thus, the cohort population may evolve as a function of time.

Master neural net NN12 may also generate various types of information as a result of analyzing the various types of input data that have been provided. At operation 470, neural net NN12 determines for an individual patient, an increased risk (e.g., a percentage, a multiplier, or any other numeric value, etc.) for having cancer relative to a population, e.g., such as a cohort population. A report including the determined risk, and information used to determine the risk, e.g., the cohort population, the size of the cohort, etc., as well as relevant statistics (e.g., margin of error) may be provided in the report. The report may also include a recommendation that high risk patients undergo more frequent screening. In some aspects, the recommended time between follow-ups is a function of clinical indicators and the cohort population. Recommendations as to behavioral changes may also be provided.

Other types of information may be provided to a patient or physician as well. For example, at operation 474, major risk factors for having cancer based upon the analysis by neural net NN12 may be reported. At operation 472, cancer-specific biomarkers that have been optimized (e.g., most heavily weighted in the risk determination) may be reported. At operation 476, a summary of data used to generate the predicted risk of cancer may be reported. At operation 478, physicians may be ranked according to their ability to diagnose early stage cancer. The techniques used by these physicians may be evaluated to develop best practices for training other physicians in the early diagnosis of cancer. At operation 480, an optimal BM velocity, which is a cutoff between velocities that are not associated with an increased risk of having cancer and velocities that are associated with an increased risk of having cancer (e.g., a threshold, etc.) may be reported.

At operation 482, patient information, regarding whether cancer was diagnosed during a follow-up visit, may be written back to the EMRs, in order to provide continuous feedback to the system.

As neural net NN12 receives data validating or invalidating whether an individual identified as high risk (as predicted by the neural net) has cancer, neural net NN12 may continue to intrinsically train as a function of time, in production mode, adjusting input and/or hidden layer weights as additional patient data becomes available. Accordingly, by utilizing a feedback loop, in which the difference between predicted results and the actual results, e.g., confirmed by invasive testing, is fed back into the system as a function of time, the accuracy of prediction may be improved as additional data is fed into the system.

The embodiments herein may automatically and continuously update the risk scores, the corresponding confidence values/margin of error, based on evolving data (e.g., medical patient data) in order to provide the highest confidence answers and recommendations. Rather than providing static calculations that always provide the same answers when given the same input, the embodiments herein continually update as new data is received, thereby, providing the physician and patient with the best most up-to-date information.

Thus, the embodiments herein provide substantial advantages over systems that generate static results based on preset, fixed criteria that is rarely revised (or only revised at periodic updates (e.g., software updates)). By acting dynamically, risk scores and recommendations can change based on evolving demographic changes, evolving medical discoveries, etc., as well as new data within the EMR and publically available databases. Therefore, the embodiments herein can continuously improve early detection of cancer, and new data becomes available, providing physicians and their patients with an automated system for accessing the best medical practices and treatments for their patients as medical advances and demographics change over time.

Figure 5:
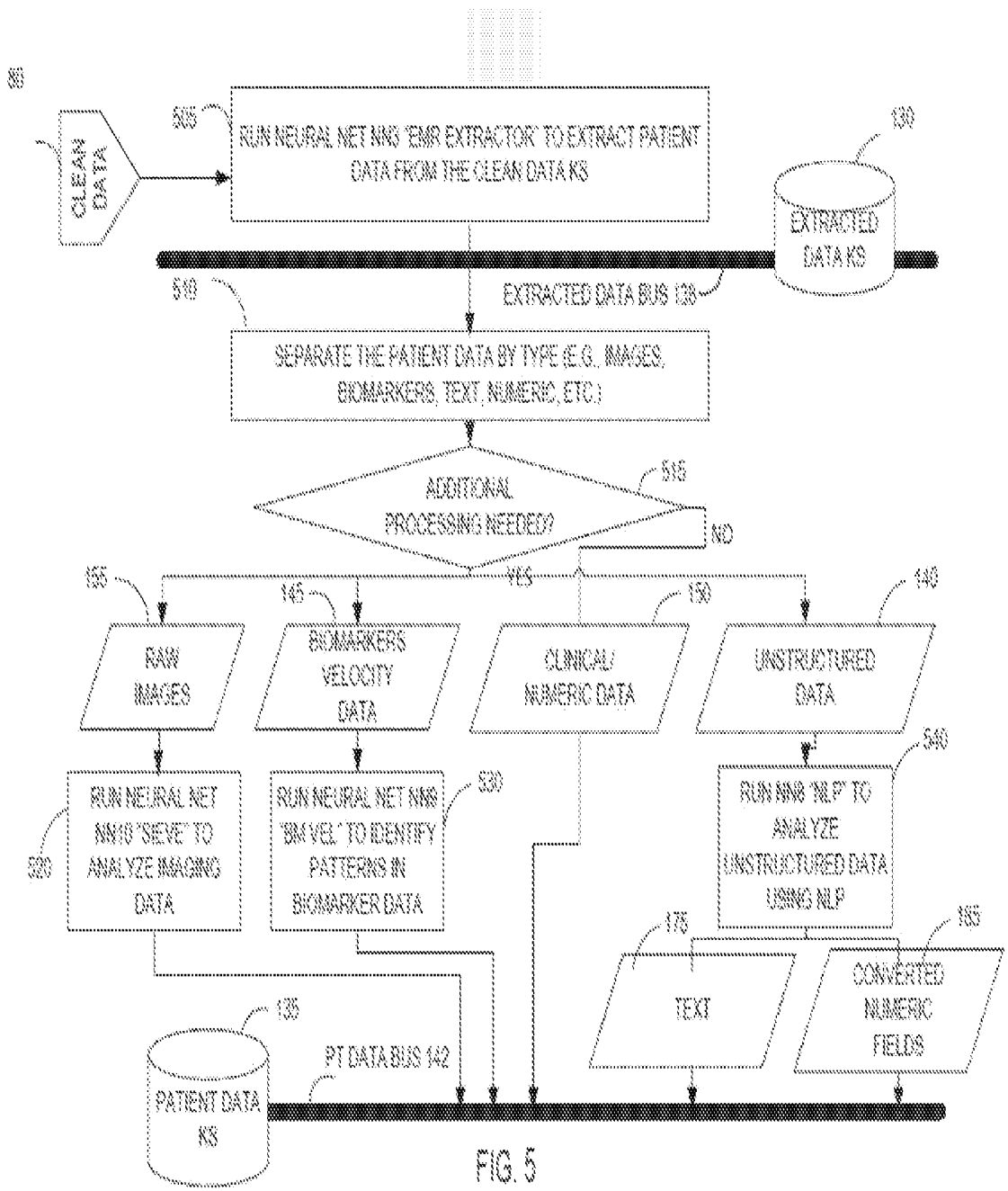
FIG. 5 is a flow diagram illustrating operations for extraction of data, in accordance with example embodiments.

FIG. 5 shows a flow diagram of example operations for EMR Extractor neural net NN3, according to embodiments of the invention. Clean data KS 80 comprises a repository of clean information from EMR db 10 and, as applicable, EMR db 20. At operation 505, neural net NN3 is utilized to extract data from clean data KS 80. This extracted data may be stored in extracted data KS 130. At operation 510, the extracted data is separated by type, e.g., raw images 155, biomarker (BM) velocity data 145, text-based unstructured data 140, and numeric/structured data 150. At operation 515, it is determined whether additional processing (by other neural nets) is needed before providing the information to the master neural net NN12 for analysis. Numeric data 150 may be stored in patient data KS 135 without additional processing. In this example, the remaining types of data are processed with other neural nets. Raw image data 155 is provided to neural net NN10, which analyzes imaging data, at operation 520. Biomarkers velocity data 145 is provided to the biomarker velocity neural net NN9, which identifies patterns in biomarker data, at operation 530. In some embodiments. NN9 may be untrained.

Unstructured data 140 is provided to natural language processing neural net NN8, at operation 540, which uses natural language processing and semantics to analyze unstructured data. The NLP may be applied to analyze the context of various types of text (e.g., physician notes, lab reports, medical history, prescribed treatment, and any other type of annotation) to determine relevant risk factors, and this information may be provided as inputs into master NN12. NN8 may also derive numeric inputs from the unstructured language, e.g., years of smoking, years of family members smoking, and any other numeric data at operation 540. For example, neural net NN8 may be employed for natural language processing of a written radiology report that accompanies a raw image. With a sufficiently large number of training examples, a NLP/deep learning program will learn how to interpret a written report relevant to a finding of cancer. In this example, neural net NN8 generates at least two outputs, e.g., text-based data 175 which comprises patient histories, image reports impressions, etc., as well as converted numeric fields 185, e.g., years of smoking, frequency of smoking, etc. Pt data KS 135 may store data sent to the bus 142 for subsequent input into the master neural net NN12.

Figure 6:
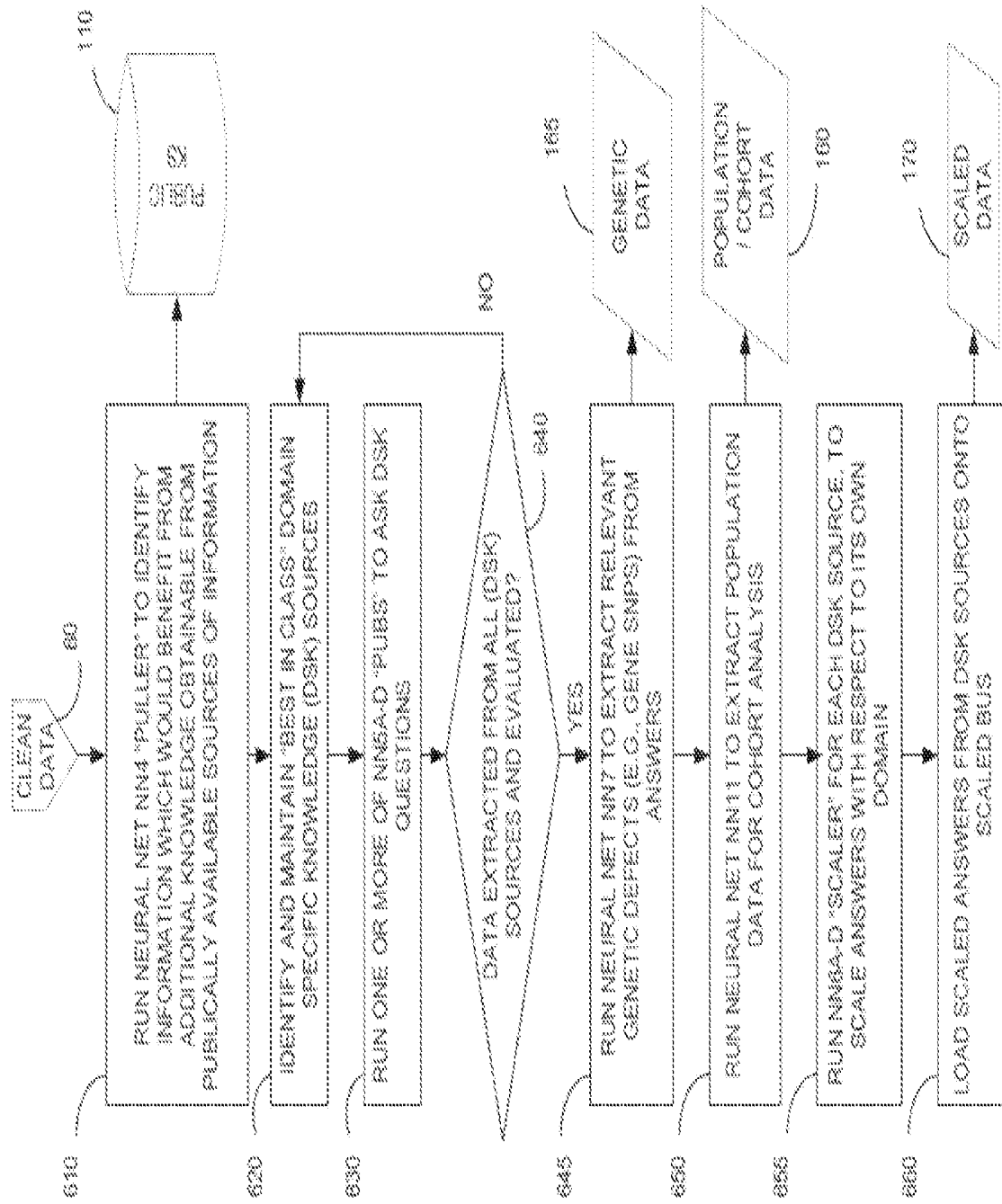
FIG. 6 is a flow diagram illustrating operations for interfacing with publicly accessible sources of data, in accordance with example embodiments.

FIG. 6 shows a flow diagram of example operations for neural nets associated with publically available data, according to embodiments of the invention. At operation 610, neural net NN4 is utilized to identify information in the EMR which would benefit from the additional knowledge obtainable from publically available sources of information. Corresponding questions may be generated, e.g., by a question-answer module, which are known in the art, and stored in public KS 110 for future retrieval. At operation 620, the best in class domain specific knowledge sources are identified and maintained. In this example, domain refers to a type of publically available information, e.g., geographic/environmental, employment, population, or genetic database. At operation 630, neural nets NN5$a$-$d$ are utilized to query each respective domain source, provided that neural net NN4 has identified a need for that specific domain information. At operation 640, it is determined whether data has been extracted from all domain sources and fully evaluated. If not, the process returns to operation 620, and identification of best in class domain specific knowledge sources is repeated. In some embodiments, provided that questions have been asked regarding the genetic domain, at operation 645, neural net NN7 is utilized to extract details of relevant genetic defects. The genetic data may be provided to master neural net NN12 via genetic data 165. At operation 650, neural net NN11 is utilized to extract population data for cohort analysis, and the extracted data, population/cohort data is provided to neural net NN 12 for analysis. At operation 655, neural net NN6$a$-$d$ is utilized to scale (or weight) the answers provided in each respective domain. It is understood that weights in one domain may not be equivalent in terms of weights in another domain, e.g., a '9' in the environmental domain may not be equivalent to a '9' in the genetic domain. At operation 660, scaled data is loaded from the dbs 30-60 onto the scaled bus 70. The scaled data may be stored in scaled KS 120 for future use.

In some embodiments, as new data becomes available for a patient, the system recomputes the risk score and provides the result to the physician.

In many domains, the answer with the highest confidence need not be the appropriate answer because there can be several possible explanations for a problem.

As will be appreciated by one skilled in the art, aspects of the embodiments herein may be embodied as a system, method or computer program product. Accordingly, aspects of the embodiments herein may take the form of an entirely hardware embodiment, an entirely software embodiment (including firmware, resident software, micro-code, etc.) or an embodiment combining software and hardware aspects that may all generally be referred to herein as a "circuit." "module" or "system." Furthermore, aspects of the embodiments herein may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Figure 11:
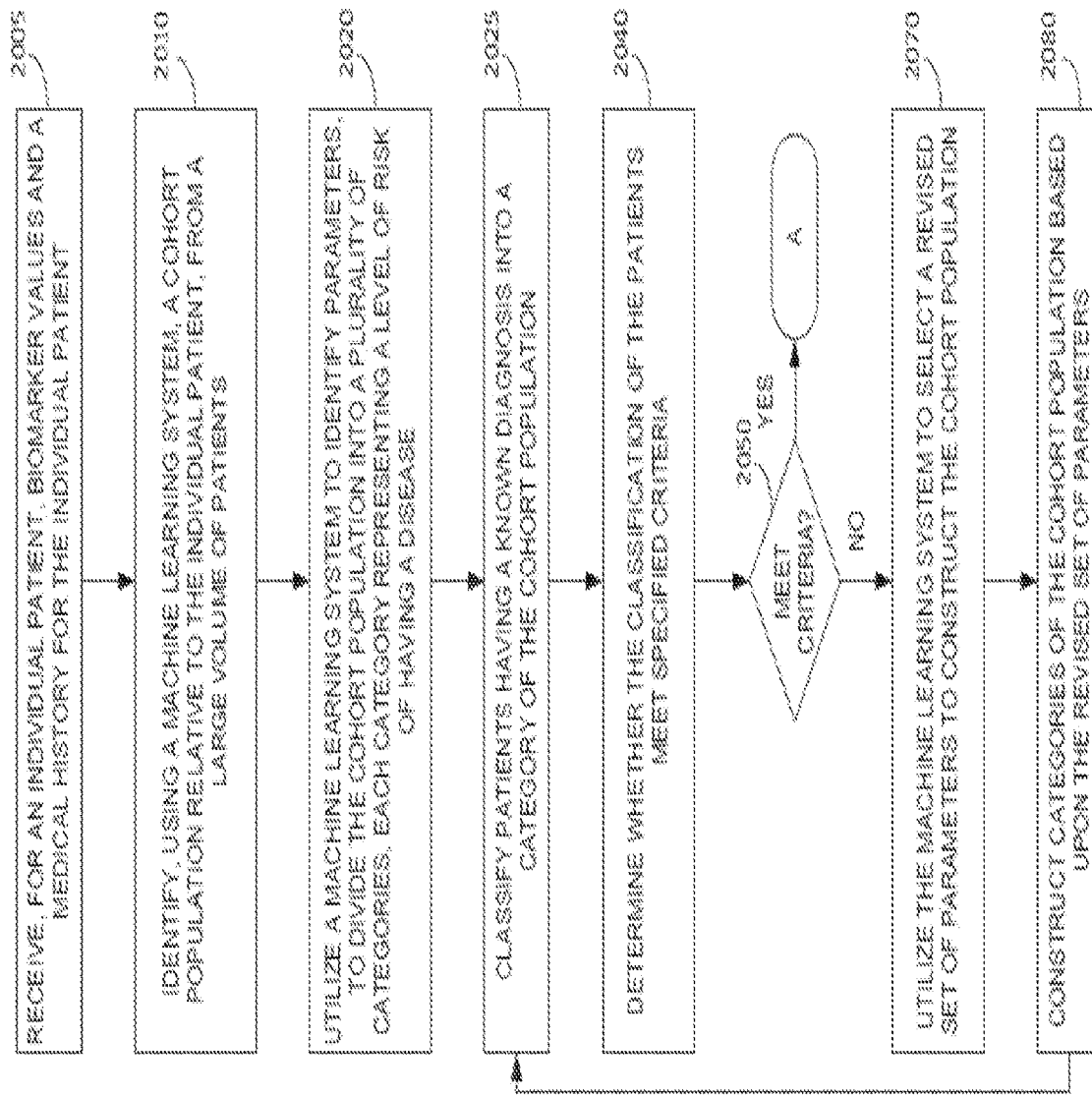
FIG. 11 is a flow diagram of example operations for utilizing a machine learning system to construct a cohort population, in accordance with example embodiments.
Figure 12:
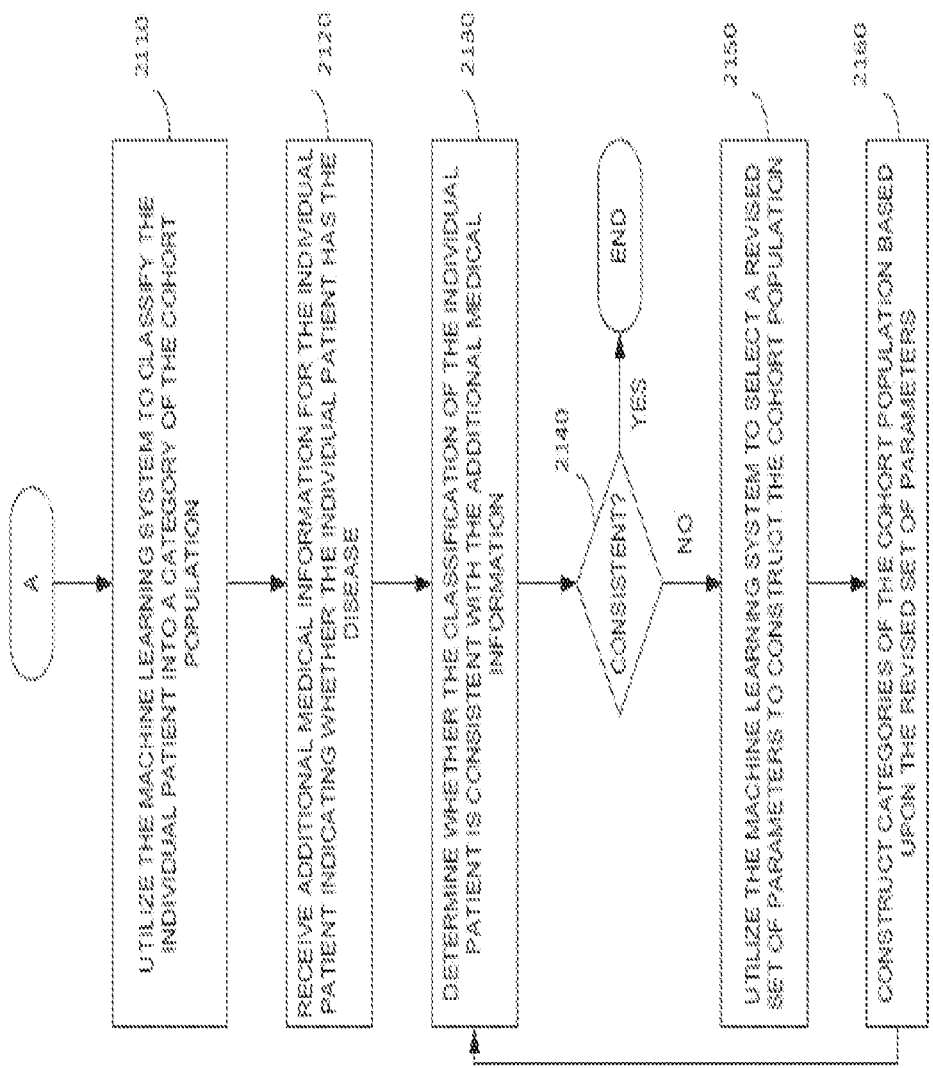
FIG. 12 is a flow diagram of example operations for utilizing a machine learning system to classify an individual patient, in accordance with example embodiments.

FIGS. 11 and 12 are flow diagrams of example processes for utilizing a machine learning system to classify an individual patient into a risk category, e.g., based upon a risk score. FIG. 11 involves constructing a cohort population, while FIG. 12 involves classification of an individual patient.

Referring to FIG. 11, at operation 2005, biomarker values and a medical history are received for an individual patient (e.g., at neural net NN12). At operation 2010, a machine learning system (e.g., neural net NN11) is used to identify a cohort population relative to the individual patient, based upon information (e.g., biomarker values, medical history, positive or negative diagnosis, etc.) from a large volume of patients (e.g., from population db 50). By providing biomarker values and the medical history of the individual patient to neural net NN11, the neural net can determine a cohort population.

At operation 2020, a machine learning system may be used to identify parameters (e.g., risk factors, corresponding weightings, etc.) to divide the cohort population into a plurality of categories, each category representing a level of risk of having a disease.

The machine learning system may not know, a priori, which parameters (e.g., risk factors) are most predictive of having lung cancer. Accordingly, the neural net may determine these parameters using an iterative process, until specified criteria are met (e.g., having a specified percentage of a population of individuals that have been diagnosed as having cancer, classified within the highest risk category). The neural net may refine the parameters (e.g., risk factors, weightings, etc.) until meeting specified criteria.

In some aspects, neural net NN11 may perform clustering (e.g., using statistical clustering techniques, etc.) on the cohort population to identify risk factors, e.g., based on medical information from the large volume of patients. For example, by performing clustering on age, the neural net NN11 may determine that individuals between 45-50 are most likely to have cancer, (e.g., first diagnosis). Other parameters may be selected in a similar manner. Accordingly, the machine learning system may select an initial set of parameters, e.g., an age/age range, a smoking history (in terms of years and/or packs per year) for analysis, and assign an initial weighting for each parameter. Accordingly, by using clustering or other grouping/analytical techniques, predictive parameters may be identified.

At operation 2025, patients (e.g., in some aspects, each patient of the large volume of patients) are classified into a category of the cohort population based on the risk score. At operation 2040, it is determined whether the classification of the patients meet specified criteria by comparing with known classifications of the patients. As the information from the large volume of patients includes a diagnosis of having or not having cancer, the classifications/risk scoring by the neural net may be evaluated for accuracy. For example, a majority of patients that do not have cancer should have a high risk score and be classified as high risk, while a majority of patients that do have cancer should have a low risk score and be categorized as low risk.

At operation 2050, if the classification (by risk score) meet specified criteria (e.g., within a specified error rate, margin of error, confidence interval, etc.) then the process may proceed to block "A" in FIG. 12. Otherwise, at operation 2070, the machine learning system will select a revised set of parameters (e.g., the revised parameters may include new fields of medical information, altered weighting for each field, etc.) to construct a risk score for classification. For example, if age and smoking history were originally used, a revised set of parameters may be constructed using age, smoking history, and biomarker values. As another example, if age and smoking history were originally used to determine a risk score, a revised set of parameters may be constructed using a decreased weighting for age, and an increased weighting for smoking history.

At operation 2080, categories of the cohort population are constructed using the revised set of parameters, and the process continues to operation 2025. Operations 2025-2080 may repeated until reaching specified criteria.

Referring to FIG. 12, at operation 2110, the machine learning system is utilized to classify (via a risk score) the individual patient into a category of the cohort population (high risk, medium risk, low risk). At operation 2120, additional medical information is received for the individual patient, indicating whether the individual patient has the disease (e.g., cancer). At operation 2130, a determination is made as to whether the classification of the individual patient is consistent with the additional medical information (e.g., the diagnosis of whether or not the patient has cancer). If the classification is consistent, at operation 2140, with the additional medical information, then the process may end. Otherwise, if the results are not consistent, the machine learning system selects a revised set of parameters (e.g., the parameters may include new fields of medical information, altered weighting for each field, etc.) for the cohort population at operation 2150. For example, a new field could be added to select a new cohort (e.g., a new biomarker) or the weights of the inputs into the neural net NN11 may be adjusted. At operation 2160, categories of the cohort population are constructed based upon the revised set of parameters (by assigning a corresponding risk score), the individual patient may be classified into a category of the cohort population, and the process iterates through operations 2130-2160 until reaching agreement.

Thus, neural networks are adaptive systems. Through a process of learning by example, rather than conventional programming by different cases, neural networks are able to evolve in response to new data. It is also noted that algorithms for training artificial neural networks (e.g., gradient descent, cost functions, etc.) are known in the art and will not be covered in detail herein.

Computer program code for carrying out operations for aspects of the embodiments herein may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the embodiments herein are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments herein. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It is understood in advance that although this disclosure includes a detailed description on cloud computing, implementation of the teachings recited herein are not limited to a cloud computing environment. Rather, embodiments herein are capable of being implemented in conjunction with any other type of computing environment now known or later developed. Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service. Service Models are as follows: Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
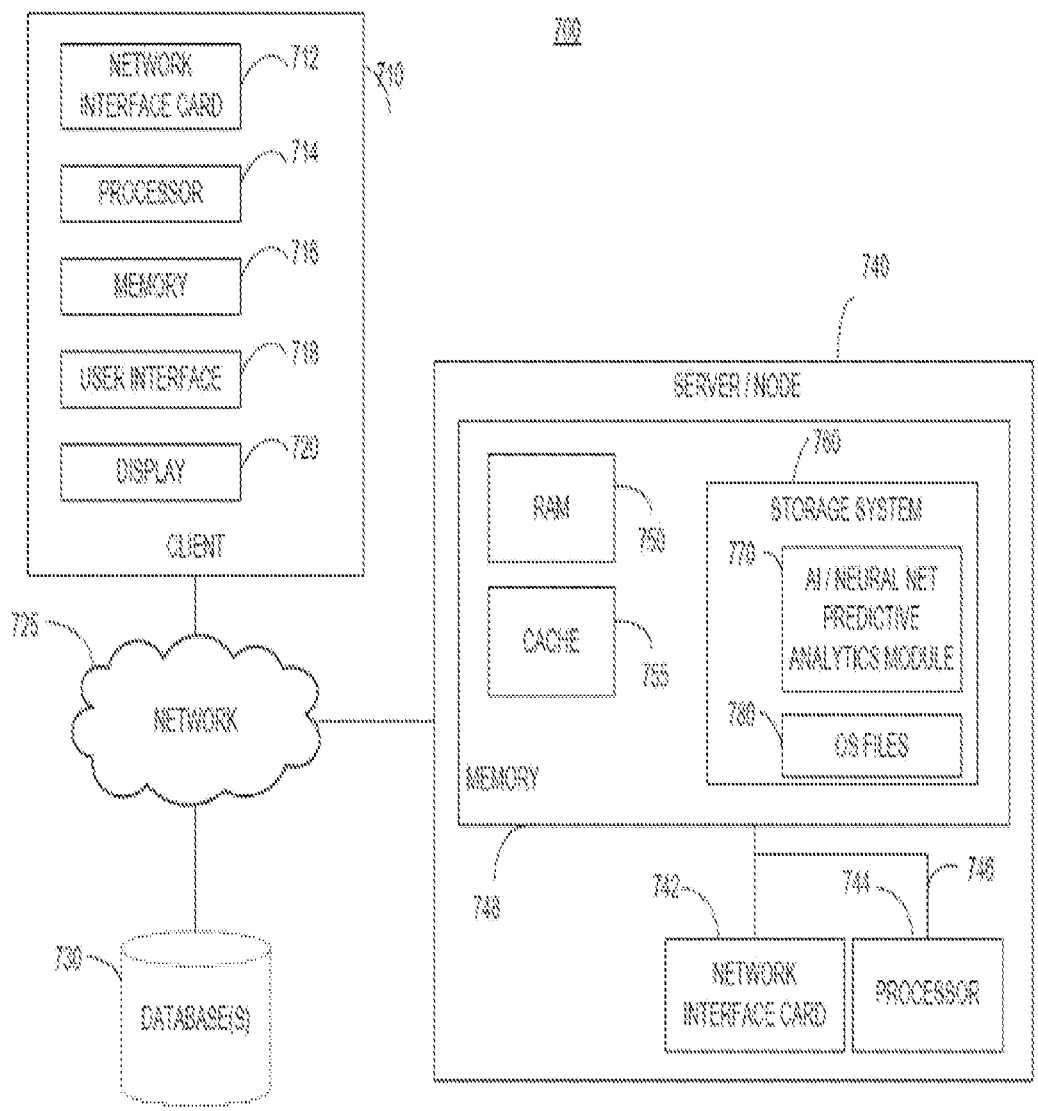
FIG. 7 is a schematic diagram illustrating a client and a computing node of an artificial intelligence system in accordance with example embodiments.

Referring now to FIG. 7, an example of computing environment that includes a computing node for an artificial intelligence system is shown. In some embodiments, the node may be a stand-alone (single) computing node. In some embodiments, the node may be implemented in a cloud-based computing environment. In other embodiments, the node may be one of a plurality of nodes in a distributed computing environment. Accordingly, computing node 740 is only one example of a suitable artificial intelligence computing node and is not intended to suggest any limitation as to the scope of use or functionality of embodiments of the invention described herein.

Regardless, computing node 740 is capable of being implemented and/or performing any of the functionality set forth hereinabove. In cloud computing node 740 there is a computer server/node 740, which is operational with numerous other computing system environments or configurations. Examples of well-known computing systems, environments, and/or configurations that may be suitable for use with server/node 740 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer server/node 740 may be described in the general context of computer system executable instructions, such as program modules, being executed by a computer system. Generally, program modules may include routines, programs, objects, components, logic, data structures, and so on that perform particular tasks or implement particular abstract data types. Server/node 740 may be practiced in distributed cloud computing environments where tasks are performed by remote processing devices that are linked through a communications network. In a distributed cloud computing environment, program modules may be located in both local and remote computer system storage media including memory storage devices.

FIG. 7 shows an example computing environment according to embodiments of the invention. The components of server/node 740 may include, but are not limited to, one or more processors or processing units 744, a system memory 748, a network interface card 742, and a bus 746 that couples various system components including system memory 748 to processor 744. Bus 746 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Computer server/node 740 typically includes a variety of computer system readable media. Such media may be any available media that is accessible by computer server/node 740, and it includes both volatile and non-volatile media, removable and non-removable media.

System memory 748 can include computer system readable media in the form of volatile memory, such as random access memory (RAM) 750 and/or cache memory 755. Computer system/server 740 may further include other removable/non-removable, volatile/non-volatile computer system storage media. By way of example only, storage system 760 can be provided for reading from and writing to a non-removable, non-volatile magnetic media (not shown and typically called a "hard drive" or solid state drive). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 746 by one or more data media interfaces. As will be further depicted and described below, memory 748 may include at least one program product having a set (e.g., at least one) of program modules that are configured to carry out the functions of embodiments of the invention. Program/utility 770, having a set (at least one) of program modules corresponding to one or more elements of NACS 100, may be stored in memory 748 by way of example, and not limitation, as well as an operating system 780, one or more application programs, other program modules, and program data. Each of the operating system, one or more application programs, other program modules, and program data or some combination thereof, may include an implementation of a networking environment. Program modules for NACS 100 generally carry out the functions and/or methodologies of embodiments of the invention as described herein.

Computer server node 740 may also communicate with a client device 710. Client device 710 may have one or more user interfaces 718 such as a keyboard, a pointing device, a display, etc., one or more processors 714, and/or any devices (e.g., network card 712, modem, etc.) that enable the client device 710 to communicate with computer server/node 740 to communicate with client device 710. Still yet, computer server/node 740 can communicate with client 710 over one or more networks 725 such as a local area network (LAN), a wide area network (WAN), and/or a public network (e.g., the Internet) via network interface card 742. As depicted, network interface card 742 communicates with the other components of computer server/node 740 via bus 746. It should be understood that although not shown, other hardware and/or software components can be used in conjunction with computer server/node 740. Examples, include, but are not limited to: microcode, device drivers, redundant processing units, external disk drive arrays, RAID systems, tape drives, and data archival storage systems, etc. One or more databases 730 may store data accessible by NACS 100.

In some embodiments, NACS 100 may run on a single server node 740. In other embodiments, NACS 100 may be distributed across a plurality of multiple nodes, wherein a master computing node provides workloads to a plurality of slave nodes (not shown).

Figure 8:
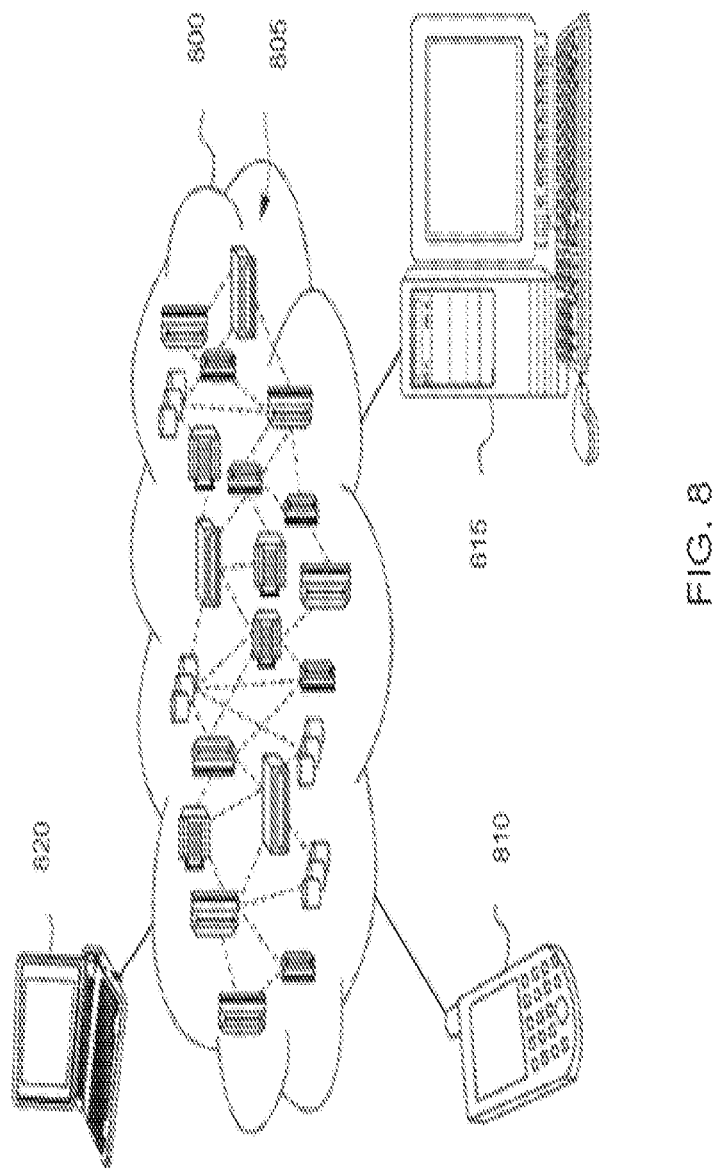
FIG. 8 is a schematic diagram illustrating a cloud computing environment for an artificial intelligence system in accordance with example embodiments.

Referring now to FIG. 8, illustrative cloud computing environment 800 is depicted. As shown, cloud computing environment 800 comprises one or more cloud computing nodes 805 with which local computing devices used by cloud consumers, such as, for example, personal digital assistant (PDA) or cellular telephone 810, desktop computer 815, laptop computer 820 may communicate. Nodes 805 may communicate with one another. They may be grouped (not shown) physically or virtually, in one or more networks, such as Private, Community, Public, or Hybrid clouds as described hereinabove, or a combination thereof. This allows cloud computing environment 800 to offer infrastructure, platforms and/or software as services for which a cloud consumer does not need to maintain resources on a local computing device. It is understood that the types of computing devices 810-820 shown in FIG. 8 are intended to be illustrative only and that computing nodes 805 and cloud computing environment 800 can communicate with any type of computerized device over any type of network and/or network addressable connection (e.g., using a web browser).

Figure 9:
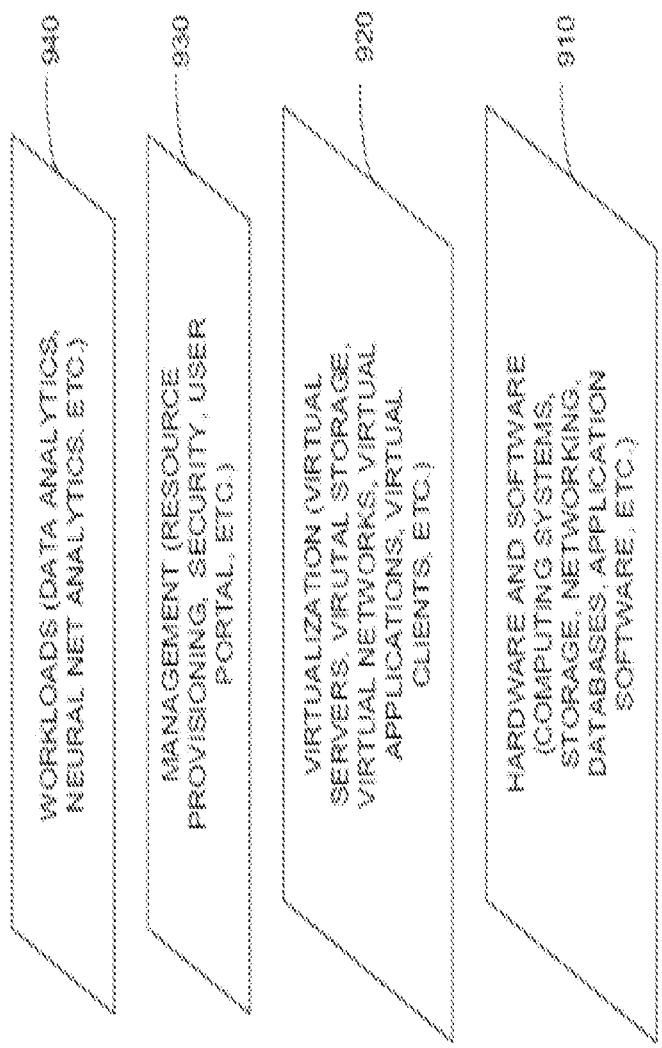
FIG. 9 is a schematic diagram illustrating an abstraction of computing model layers in accordance with example embodiments.

Referring now to FIG. 9, a set of functional abstraction layers provided by cloud computing environment 800 (FIG. 8) is shown. It should be understood in advance that the components, layers, and functions shown in FIG. 9 are intended to be illustrative only and embodiments of the invention are not limited thereto. As depicted, the following layers and corresponding functions are provided: Hardware and software layer 910 includes hardware and software components. Examples of hardware components include mainframes, RISC (Reduced Instruction Set Computer) architecture based servers: storage devices; networks and networking components. Examples of software components include network application server software, application server software; and database software. Virtualization layer 920 provides an abstraction layer from which the following examples of virtual entities may be provided: virtual servers; virtual storage; virtual networks, including virtual private networks; virtual applications and operating systems; and virtual clients. In one example, management layer 930 may provide the functions described below. Resource provisioning provides dynamic procurement of computing resources and other resources that are utilized to perform tasks within the cloud computing environment. Other functions provide cost tracking as resources are utilized within the cloud computing environment. In one example, these resources may comprise application software licenses. Security provides identity verification for cloud consumers and tasks, as well as protection for data and other resources. User portal provides access to the cloud computing environment for consumers and system administrators.

Workloads layer 940 provides examples of functionality for which the cloud computing environment may be utilized. Examples of workloads and functions which may be provided from this layer include: data analytics processing; neural net analytics, etc.

Figure 14:
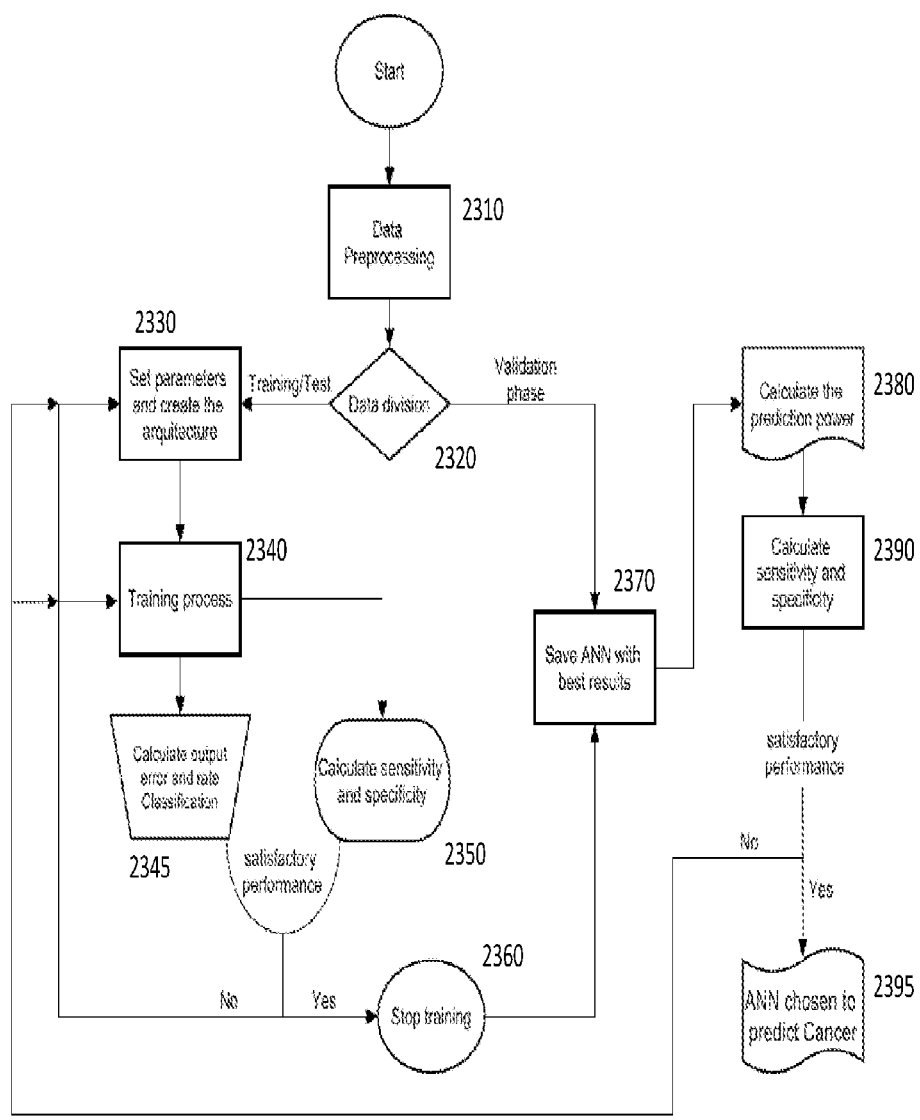
FIG. 14 is a flow diagram of example operations of generating an artificial neural net to predict a likelihood of having cancer, in accordance with example embodiments.

Referring to FIG. 14, a flowchart is provided that describes generating an artificial neural net (ANN) to predict a likelihood of having cancer. At operation 2310, data preprocessing may occur (e.g., normalization of data). In some embodiments, the concentration values of each biomarker and clinical data may be pre-processed numerically before being provided as input into the ANN. For example, the values may be normalized to have a mean equal to 0 and a standard deviation of 1. The normalized data may be randomized before being provided as inputs into the ANN. At operation 2320, the test data set is divided into test/training data and validation data, e.g., 70% for the training phase, and 30% for the validation phase. At operation 2330, parameters are selected (e.g., number of hidden layers, number of nodes, inputs, outputs, transfer/activation functions, etc.) and the corresponding architecture is created for the system.

At operation 2340, the training/test data is used to train the system and generate a classifier. The initial weights between each connection and the bias of the ANN is set at the beginning, e.g., in a randomized manner, and during training the weights are adjusted by a learning function. Criteria are selected to stop the training phase in an ANN, e.g., when the root-mean-square error is less than a threshold or when the correct classification rate meets a threshold. The values of the biomarkers and clinical data are directly involved in the modification of the connection weights in the ANN model during training. Methods for avoiding crossfitting are also applied.

Once the training process is complete, two operations are performed: (1) at operation 2345, the output error and rate classification are determined; and (2) at operation 2350, the sensitivity and specificity are determined. If the sensitivity and specificity meet desired performance criteria (e.g., a threshold such as at least 70% sensitivity with an 80% specificity), the training ceases, at operation 2360. On the other hand, if performance criteria is not met, then the parameters are adjusted at operation 2330, and the classifier is retrained using the adjusted parameters at operation 2340.

Provided that the sensitivity and specificity performance criteria are met (e.g., threshold(s)), the neural net is saved at operation 2370. In some embodiments, multiple neural nets may meet specified criteria and may be saved, with the best performing neural net and its associated parameters subsequently selected, e.g., for use in a clinical setting.

In some embodiments, the optimal ANN architecture is chosen based on the mean squared error training and the best classification percentage. To determine which ANN architecture is most appropriate for the dataset of concentration of biomarkers and clinical parameters, various ANNs with distinct configurations may be tested, including with one hidden layer (with 1, 2, 3 nodes, etc.), two hidden layers (with different combinations i.e. 3-2, 5-3, 2-6, etc. nodes) or three hidden layers. Only the ANNs that present the best ability to correctly classify the largest possible number of data are chosen and are saved. The neural net is then used to classify the data from the validation phase, and the prediction power and sensitivity and specificity are determined (see, operations 2380-2390).

Once the sensitivity and specificity meet desired performance at operation 2390, then the neural net is selected for prediction of cancer at operation 2395. This version may be static, semi-static or continuously updated.

In some embodiments, this configuration may be made static, meaning that the neural net is not refined based on collection of additional data, and is deployed, e.g., to a doctor's office, for use in determining a likelihood of cancer in a patient. In still other embodiments, the neural net is continually refined based on collection of additional data, and when deployed, e.g., to a doctor's office or a remote server for use in estimating a likelihood of cancer in a patient, the model is continuously updated as more data becomes available. In still other embodiments, this configuration may be periodically updated, e.g., according to a prescribed schedule.

The terminology used herein is for the purpose of describing particular embodiments only and is not intended to be limiting with respect to a particular embodiment of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the embodiments herein has been presented for purposes of illustration and description, but is not intended to be exhaustive or limited to the embodiments disclosed herein. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

In a further exemplary embodiment, the decision-support application described herein is applied to the early detection of cancer. In one aspect, the decision-support application utilizes data from blood biomarkers, patent medical records, epidemiological factors associated with increased or decreased lung cancer risk gathered from the medical literature, clinical factors associated with increased or decreased lung cancer risk gathered from the medical literature, and analyses of patient x-rays and other images generated by various scanning techniques well known in the art in concert with information gathered from the question-answering system in order to determine a patient's cancer risk relative to an appropriate matched cohort. In a further aspect, this determination is improved over time utilizing machine learning to improve the algorithm based upon prior results.

In a further aspect, the medical images include, but are not limited to x-ray based techniques (conventional x-rays, computed tomography (CT), mammography, and use of contrast agents), molecular imaging using a variety of radio-pharmaceuticals to visuals biological processes, magnetic imaging (MRI) and ultrasound.

In a further aspect, the NACS 100 described herein provides a patient's lung cancer risk as well as an assessment of the likelihood of other non-cancer lung diseases. For example, the application may assess the likelihood of COPD, asthma, or other disorders. In a further aspect, the application described herein may provide an assessment of a patient's risk of multiple cancers simultaneously. In a further aspect, the application may also provide a list of potential tests that may increase the confidence value for each potential assessed risk as well as to increase or decrease the assessed risk as a result of the new data.

In a further aspect, the clinical and epidemiological factors that may be analyzed to assess a patient's relative risk of lung cancer include, but are not limited to disease symptoms like persistent cough, bloody cough or unexpected weight loss, radiological results like suspicious findings from chest x-rays or CT scans, and environmental factors like amount of exposure to air pollution, radon, asbestos, or second hand smoke, history of smoking both in terms of time and intensity of use, and family history of lung cancer.

In a further exemplary embodiment, the machine learning application described herein provides results in a secured, cloud-based physician portal.

One of skill in the art recognizes that the embodiments disclosed herein may be practiced with any advanced application capable of machine learning and natural language processing.

All references cited herein are incorporated by reference in their entirety.

EXAMPLES

The Examples below are given so as to illustrate the practice of one or more embodiments of the invention, and are intended to be non-limiting with regard to the embodiments presented herein.

Example 1

Training Neural Analysis of Cancer System (NACS) With a Large Dataset

Biomarker data from tens of thousands of patients (about 41,000 participants) was collected in a study from Taiwan (Wen, Y. H., "Cancer screening through a multi-analyte serum biomarker panel during health check-up examinations: Results from a 12-year experience" *Clinica Chimica Acta* 450 (2015) 273-276). Tumor markers AFP, CA 15-3, CA125, PSA SC, CEA were assayed using kits from Abbott Diagnostics. Tumor markers CYFRA 21-1 and CA 19-9 were assayed using kits from Roche Diagnostics. Tumor marker CEA was assayed using kits from Siemens Healthcare. This data set may be used as a training data set for NACS 100. This patient data, coupled with comparable data from one or more other jurisdictions for geographic and genetic diversity, is stored in one or more electronic medical records databases (e.g., EMR db 10) along with the clinical outcomes i.e. whether cancer was detected within about one year of biomarker testing and, if so, the type of cancer. Training data from Wen et al. will be particularly useful for pan-cancer screening (i.e. testing of asymptomatic patients for an array of tumor types including pancreas, liver, and prostate).

Biomarker data from thousands of patients (about 3,000 patients) was also collected in a study from Barcelona Spain (Molina, R., "Assessment of a Combined Panel of Six Serum Tumor Markers for Lung Cancer" Am. J. Respir. Crit. Care Med. (2015)]. In this study, tumor markers CEA, CA 15.3, CYFRA 21.1 and NSE were assayed using kits from Roche, and SCC and ProGRP were assayed using kits from Abbott Diagnostics. This data set may also be used as training data set for NACS 100.

This patient data, coupled with comparable data from one or more other jurisdictions for geographic and genetic diversity, is stored in one or more electronic medical records databases (e.g., EMR db 10) along with the clinical outcomes i.e. whether lung cancer was detected within about one year of biomarker testing. Training data from the Molina et al. will be particularly useful for aiding in lung cancer diagnosis when patients have vague or ambiguous signs or symptoms of lung cancer (e.g. cough, chest pain, etc.).

Corresponding patient medical information/history may also be stored in EMR db 10, such that for each patient participating in the study, one or more of the following type of data or parameters are also present: age, smoking history, gender, family history (e.g., whether a first degree relative has been diagnosed with cancer before age 50, etc.) and symptoms (e.g., unexplained weight loss, fatigue, persistent cough, abdominal pain, chest pain, etc.). Typically, data from a large volume of patients is needed for sufficient training of NACS 100.

The Neural Analysis of Cancer System (NACS) 100 may access this data, using for example neural nets NN2*a* and NN2*b*, to determine whether the data is clean, e.g., whether there is any missing, problematic or conflicting data. Missing data may be ranked according to potential impact on the risk score, and data of high impact is corrected. NACS 100 makes a determination as to whether sufficient information is available to determine a risk score, and if so, the system proceeds with analysis of the data. Data is anonymized, as needed.

Once the data is sufficiently clean, neural net NN3 extracts the data and separates the data according to data type. In some embodiments, data may be separated into unstructured data 140 (e.g., text-based data including physician notes, etc.), clinical and numeric data 150 (e.g., symptoms, age, gender, smoking history, family history, etc.). In the event that imaging data 155 and biomarker velocity 145 information is present, these two types of data may be separated as well. Clinical and numeric data 150 is provided to master neural net NN12; biomarker velocity 145 is provided to neural net NN9 for analysis, unstructured data 140 is provided to neural net NN8 for analysis, and imaging data is provided to NN10 for imaging analysis. The output of the neural nets NN8, NN9 and NN10 are provided to NN12 for analysis.

Neural net NN11 analyzes the dataset to determine parameters for constructing a cohort population. Various statistical techniques, e.g., clustering, etc., may be used as part of this analysis. In some embodiments, NACS 100 may determine a cohort population based upon one or more inputs provided, e.g., an age or age range, smoking history, gender, etc. NACS 100, e.g., master neural net NN12, analyzes the various inputs, including the clinical and numeric data (including biomarker data), unstructured data, imaging and biomarker velocity data as available, and generates risk categories corresponding to a level of risk (based upon a risk score) for developing cancer. These risk categories can be used to determine a level of risk for individual patients, as set forth in the example below.

Example 2

Using NACS to Determine a Risk of the Presence of Lung Cancer

Data from an individual patient may be collected, e.g., via a web application form, such as the example form provided in Table A. Patient information including clinical/numeric demographic data, imaging diagnostics and corresponding text notes as well as biomarker data may be collected via the web application and stored in an electronic records db.

TABLE A

| | | NOTES | FIELD TYPE |
|---|---|---|---|
| Specimen | Clinical Collection Site | | Text field |
| | Patient ID | | Letters + numbers |
| | Sample ID | | Letters + numbers |
| | Serum Sample Collection Date | | Numbers |
| Patient Information | Patient Age | | Numbers |
| | Gender | Choose from Male/Female | Drop-down |
| | Ethnicity | Choose from Asian, African, Caucasian | Drop-down |
| | Smoking Status | Choose from Current smoker/Former smoker | Drop-down |
| | Cigarettes/Day | IF CURRENT: Number | Numbers |
| | Smoking Duration | IF CURRENT: Number | Numbers |
| | Age Quit | If former: Number | Numbers |
| | Years since quitting | If former: Number | Numbers |
| | Family History of lung cancer | YES/NO | Drop-down |
| | Symptoms | YES/NO | Drop-down |
| | List symptoms | If YES; free text field | Text field |
| | Concomitant illness at the time of blood draw: | YES/NO | Drop-down |
| | Lung diseases | If YES | Text field |
| | Other diseases | If YES | Text field |
| | Concomitant medication at the time of blood draw | YES/NO | Drop-down |
| | List | | Text field |
| Clinical Diagnosis | Imaging diagnostics performed | YES/NO | Drop-down |
| | Name of the test | If YES, chose from CT, LDCT, X-ray, Other | Drop-down |
| | Date | If YES | Numbers |
| | Nodules | YES/NO | Drop-down |
| | Size of nodules | | Numbers |
| | Number of nodules | | Numbers |
| | Nodules characteristics - Margins regular | YES/NO | Drop-down |
| | Nodules characteristics - Round glass appearance | YES/NO | Drop-down |
| | Nodules characteristics - Calcifications | YES/NO | Drop-down |
| | Other benign disease | YES/NO | Drop-down |
| | Name | If YES, text field | Text field |

TABLE A-continued

|  |  | NOTES | FIELD TYPE |
|---|---|---|---|
|  | Invasive procedure performed | YES/NO | Drop-down |
|  | Name of the procedure | If YES, chose from biopsy, VATS, open chest surgery, other | Drop-down |
|  | Date of surgery |  | Numbers |
|  | Lung Cancer | YES/NO | Drop-down |
|  | TNM |  | Letters + numbers |
|  | AJCC/UICC Stage Group |  | Letters + numbers |
|  | Histological Subtype |  | Text field |
|  | Metastasis present | YES/NO | Drop-down |
|  | List sites of metastasis |  | Text field |
|  | Other benign disease | YES/NO | Drop-down |
|  | Name | If YES | Text field |
| Clinical Test Results - BIOMARKER A | Instrument | Choose from ARCHITECT or Elecsys | Drop-down |
|  | Test Name |  | Text field |
|  | Sample receiving date |  | Numbers |
|  | Test Date |  | Numbers |
|  | Test Units |  | Letters and symbols |
|  | Value |  | Numbers |

Based upon the information collected from this form, NACS 100 can analyze this data, determine a cohort population (from the training data set), construct categories of risk, and generate a corresponding risk score for the patient. Based upon which category the patient is classified into, from the risk score, a likelihood of having cancer can be calculated.

Thus, as an output, a report may be generated by NACS 100 indicating an individual patient's risk with respect to a patient cohort. The risk may be reported as a percentage, a multiplier or any equivalent. The report may also list a margin of error, e.g., a 72% chance plus or minus 10%.

Generally, the report will list the parameters used to construct the cohort population. For example, if NACS 100 determines that the parameters for the cohort are gender, age range, family history, and smoking history, then the report lists cohort parameters as e.g., Male, Age 50-60, 10 year smoking history with 2 packs per day, relative (father) died at age 60 of lung cancer. It is understood that these cohort parameters are an example, and that many other sets of cohort parameters may be selected by NACS 100, e.g., based upon any combination of inputs into the system.

In some embodiments, a cohort size is provided, e.g., the cohort may be 525 individuals. Also, a list of genetic risk factors may be provided, e.g., mutations from genetic testing, e.g., [EGFR, KRAS], a family history, and biomarker scores [biomarker and corresponding concentration (if applicable), e.g., CYFRA 8 ng/ml, CA 15-3 45 U/ML].

Thus, biomarker data from an individual patient may be supplied to NACS 100, and NACS 100 may analyze the data (e.g., clinical and numeric data, symptoms, etc.) to output a report of a patient's predicted likelihood of having cancer.

Example 3

Training of the Artificial Neural Network (ANN)

There are many different types of ANNs that can be used to model or predict data where the correlation between dependent and independent variables is nonlinear or difficult to fit to an equation. For example, there are at least 25 different types of ANNs, wherein each type may provide different results based on different selected parameters, including but not limited to: training algorithms, activation/transfer functions, architectures (e.g., one-, two-, three- or more hidden layers; one, two, three or more inputs as part of the input layer; one, two, three or more outputs as part of the output layer).

In this example, the flowchart of FIG. 14 was employed to train the artificial neural network. A Feedforward Network, Pattern Recognition Network was selected as the specific type of neural network used to classify cancer patients and control subjects. The software used to design the ANN in this example was MATLAB™. However, any suitable software may be used.

To train the ANN, the biomarkers CA 19-9, CEA, Cyfra 21-1, NSE, Pro-GRP, SCC, and the clinical parameters: smoking status, packages years, patient age, family history of lung cancer, and recoded has symptoms from 344 patients with newly diagnosed lung cancer and 105 subjects at high risk for developing lung cancer but with no history of lung disease were used as inputs to the network. For symptoms, the variable (recoded has symptoms) frequently had a high rate of missing information, in some cases with more than 90% of patient data missing. In some embodiments, CEA, NSE, CYFRA 21-1. CA19-9 were tested by a Roche device and Pro-GRP and SCC were tested by an Abbott Architect i2000 device. Manufacturer's cutoffs for the 6 biomarkers were used, e.g., CEA>=5 ug/L.; CYFRA 21-1>=3.3 ug/L; NSE>=25 ug/L; SCC>=2 ug/L; CA19-9>=37 u/mL and Pro-GRP>=50 ng/L.

An example of input data to a neural network is provided in the following Table 1.

TABLE 1

| Smoking Status | Pack-yr | Patient Age At Exam | Family History Lung Cancer | Recoded has symptoms | CA 19-9 | CEA | CYFRA | NSE | Pro-GRP | SCC | NoduleSize |
|---|---|---|---|---|---|---|---|---|---|---|---|
| 1 | 50 | 74 | 0 | 0 | 41 | 6 | 12 | 14 | 37 | 2 | 45 |
| 1 | 50 | 77 | 0 | 0 | 13 | 5 | 8 | 15 | 46 | 2 | 50 |
| 1 | 50 | 69 | 0 | 1 | 9 | 3 | 4 | 14 | 45 | 2 | 23 |
| 1 | 20 | 64 | 0 | 1 | 30 | 9 | 2 | 11 | 47 | 2 | 20 |
| 1 | 50 | 62 | 0 | 1 | 5 | 4 | 3 | 21 | 52 | 2 | 55 |
| 1 | 40 | 61 | 0 | 0 | 11 | 2 | 39 | 17 | 20 | 8 | 63 |
| 1 | 20 | 74 | 0 | 0 | 1 | 2 | 2 | 14 | 27 | 1 | 25 |
| 1 | 20 | 66 | 0 | 0 | 9 | 2 | 1 | 24 | 934 | 1 | 35 |
| 1 | 20 | 62 | 0 | 1 | 10 | 2 | 4 | 12 | 56 | 1 | 42 |

TABLE 1-continued

| Smoking Status | Pack-yr | Patient Age At Exam | Family History Lung Cancer | Recoded has symptoms | CA 19-9 | CEA | CYFRA | NSE | Pro-GRP | SCC | NoduleSize |
|---|---|---|---|---|---|---|---|---|---|---|---|
| 1 | 20 | 62 | 0 | 0 | 10 | 3 | 4 | 15 | 27 | 1 | 68 |
| 0 | 20 | 65 | 0 | 0 | 191 | 2 | 3 | 9 | 52 | 1 | 25 |
| 1 | 20 | 71 | 1 | 0 | 28 | 2 | 2 | 10 | 24 | 0 | 27 |
| 0 | 20 | 58 | 0 | 1 | 4 | 1 | 1 | 11 | 20 | 1 | 35 |
| 1 | 50 | 65 | 0 | 1 | 20 | 3 | 5 | 175 | 416 | 1 | 80 |
| 0 | 20 | 67 | 0 | 0 | 50 | 4 | 8 | 12 | 42 | 1 | 59 |
| 1 | 20 | 60 | 0 | 0 | 41 | 95 | 5 | 10 | 29 | 1 | 32 |
| 1 | 20 | 73 | 0 | 1 | 13 | 4 | 9 | 72 | 36 | 6 | 90 |
| 1 | 20 | 58 | 0 | 1 | 8 | 1 | 4 | 15 | 38 | 1 | 9 |
| 1 | 20 | 69 | 0 | 1 | 44 | 80 | 3 | 10 | 40 | 0 | 22 |
| 1 | 20 | 61 | 0 | 1 | 17 | 130 | 12 | 14 | 46 | 1 | 28 |
| 1 | 20 | 64 | 1 | 1 | 15 | 85 | 23 | 20 | 36 | 1 | 37 |

Two outputs were selected: 1) those having a high probability of lung cancer and 2) those having a low probability of lung cancer (control subjects).

In some embodiments, the concentration value of each biomarker and the clinical data were pre-processed numerically before being used as inputs for the training of ANN. The values were normalized to have a mean equal to 0 and a standard deviation of 1, e.g., using the function "mapstd". Subsequently, the normalized data were randomized before being used as inputs for the ANN. The data set was divided using the "divideind" function as follows: 70% for the training phase, 30% for the validation phase.

For the input layer, the biomarkers and clinical data described above were used. For the hidden layers, a tangential activation function was used, e.g., a nonlinear tangential sigmoidal activation function. For the output layer, a linear activation function was used, ranging from 0 to 1, e.g., the linear "purelin" activation function. A Scaled Conjugate Gradient algorithm was used for training the ANN.

Other algorithms may be used, including but not limited to: Levenberg-Marquardt (LM), BFGS Quasi-Newton (BFG), Resilient Backpropagation (RP), Conjugate Gradient with Powell/Beale Restarts (CGB), Fletcher-Powell Conjugate Gradient (CGF), Polak-Ribiére Conjugate Gradient (CGP), One Step Secant (OSS) and Variable Learning Rate Backpropagation (GDX).

Optimal ANN architecture(s) were chosen based on the mean squared error training and the best classification percentage. It was determined which ANN architecture was the most appropriate for the dataset of biomarkers concentration and clinical parameters. In order to determine the best ANN, around 800 ANNs with distinct configurations were tested: with one hidden layer (e.g., 1, 2, 3 neurons, etc.), two hidden layers (e.g., different combinations i.e. 3-2, 5-3, 2-6, etc. nodes), and three hidden layers. The ANNs that presented the best ability to correctly classify the largest possible number of data were chosen and saved. Optimal architecture(s) were chosen as the one(s) having the lowest training error and the higher classification percentage. The following Table 2 shows examples of different configurations (number of hidden layers, and number of nodes per layer) that were tested for the neural net system.

TABLE 2

| 1-hidden layer | | 2-hidden layer | | 3-hidden layer | |
|---|---|---|---|---|---|
| 1 | 1 | 1 | 1 | 1 | 1 |
| 2 | 1 | 2 | 1 | 2 | 1 |
| 3 | 1 | 3 | 1 | 3 | 1 |
| 4 | 1 | 4 | 1 | 4 | 1 |
| 5 | 1 | 5 | 1 | 5 | 1 |
| 6 | 1 | 6 | 1 | 6 | 1 |
| 7 | 1 | 7 | 1 | 7 | 1 |
| 8 | 1 | 8 | 1 | 8 | 1 |
| 9 | 1 | 9 | 1 | 9 | 1 |
| 10 | 1 | 10 | 1 | 10 | 1 |
| 11 | 1 | 11 | 1 | 1 | 1 |
| 12 | 1 | 12 | 1 | 2 | 1 |
| 13 | 1 | 13 | 1 | 3 | 1 |
| 14 | 1 | 14 | 1 | 4 | 1 |
| 15 | 1 | 15 | 1 | 5 | 1 |
| 16 | 1 | 16 | 1 | 6 | 1 |
| 17 | 1 | 17 | 1 | 7 | 1 |
| 18 | 1 | 18 | 1 | 8 | 1 |
| 19 | 1 | 19 | 1 | 9 | 1 |
| 20 | 1 | 20 | 1 | 10 | 1 |
| 21 | 2 | 1 | 2 | 1 | 2 |
| 22 | 2 | 2 | 2 | 2 | 2 |
| 23 | 2 | 3 | 2 | 3 | 2 |
| 24 | 2 | 4 | 2 | 4 | 2 |
| 25 | 2 | 5 | 2 | 5 | 2 |
| 26 | 2 | 6 | 2 | 6 | 2 |
| 27 | 2 | 7 | 2 | 7 | 2 |
| 28 | 2 | 8 | 2 | 8 | 2 |
| 29 | 2 | 9 | 2 | 9 | 2 |
| 30 | 2 | 10 | 2 | 10 | 2 |
| 31 | 2 | 11 | 2 | 1 | 2 |
| 32 | 2 | 12 | 2 | 2 | 2 |
| 33 | 2 | 13 | 2 | 3 | 2 |
| 34 | 2 | 14 | 2 | 4 | 2 |
| 35 | 2 | 15 | 2 | 5 | 2 |
| 36 | 2 | 16 | 2 | 6 | 2 |
| 37 | 2 | 17 | 2 | 7 | 2 |
| 38 | 2 | 18 | 2 | 8 | 2 |
| 39 | 2 | 19 | 2 | 9 | 2 |
| 40 | 2 | 20 | 2 | 10 | 2 |
| 41 | 3 | 1 | 3 | 1 | 3 |
| 42 | 3 | 2 | 3 | 2 | 3 |
| 43 | 3 | 3 | 3 | 3 | 3 |
| 44 | 3 | 4 | 3 | 4 | 3 |
| 45 | 3 | 5 | 3 | 5 | 3 |
| 46 | 3 | 6 | 3 | 6 | 3 |
| 47 | 3 | 7 | 3 | 7 | 3 |
| 48 | 3 | 8 | 3 | 8 | 3 |
| 49 | 3 | 9 | 3 | 9 | 3 |
| 50 | 3 | 10 | 3 | 10 | 3 |
| 51 | 3 | 11 | 3 | 1 | 3 |
| 52 | 3 | 12 | 3 | 2 | 3 |
| 53 | 3 | 13 | 3 | 3 | 3 |
| 54 | 3 | 14 | 3 | 4 | 3 |
| 55 | 3 | 15 | 3 | 5 | 3 |

TABLE 2-continued

| 1-hidden layer | 2-hidden layer | | 3-hidden layer | |
|---|---|---|---|---|
| 56 | 3 | 16 | 3 | 6 | 3 |
| 57 | 3 | 17 | 3 | 7 | 3 |
| 58 | 3 | 18 | 3 | 8 | 3 |
| 59 | 3 | 19 | 3 | 9 | 3 |
| 60 | 3 | 20 | 3 | 10 | 3 |
| 61 | 4 | 1 | 4 | 1 | 4 |
| 62 | 4 | 2 | 4 | 2 | 4 |
| 63 | 4 | 3 | 4 | 3 | 4 |
| 64 | 4 | 4 | 4 | 4 | 4 |
| 65 | 4 | 5 | 4 | 5 | 4 |
| 66 | 4 | 6 | 4 | 6 | 4 |
| 67 | 4 | 7 | 4 | 7 | 4 |
| 68 | 4 | 8 | 4 | 8 | 4 |
| 69 | 4 | 9 | 4 | 9 | 4 |
| 70 | 4 | 10 | 4 | 10 | 4 |
| 71 | 4 | 11 | 4 | 1 | 4 |
| 72 | 4 | 12 | 4 | 2 | 4 |
| 73 | 4 | 13 | 4 | 3 | 4 |
| 74 | 4 | 14 | 4 | 4 | 4 |
| 75 | 4 | 15 | 4 | 5 | 4 |
| 76 | 4 | 16 | 4 | 6 | 4 |
| 77 | 4 | 17 | 4 | 7 | 4 |
| 78 | 4 | 18 | 4 | 8 | 4 |
| 79 | 4 | 19 | 4 | 9 | 4 |
| 80 | 4 | 20 | 4 | 10 | 4 |
| 81 | 5 | 1 | 5 | 1 | 5 |
| 82 | 5 | 2 | 5 | 2 | 5 |
| 83 | 5 | 3 | 5 | 3 | 5 |
| 84 | 5 | 4 | 5 | 4 | 5 |
| 85 | 5 | 5 | 5 | 5 | 5 |
| 86 | 5 | 6 | 5 | 6 | 5 |
| 87 | 5 | 7 | 5 | 7 | 5 |
| 88 | 5 | 8 | 5 | 8 | 5 |
| 89 | 5 | 9 | 5 | 9 | 5 |
| 90 | 5 | 10 | 5 | 10 | 5 |
| 91 | 5 | 11 | 5 | 1 | 5 |
| 92 | 5 | 12 | 5 | 2 | 5 |
| 93 | 5 | 13 | 5 | 3 | 5 |
| 94 | 5 | 14 | 5 | 4 | 5 |
| 95 | 5 | 15 | 5 | 5 | 5 |
| 96 | 5 | 16 | 5 | 6 | 5 |
| 97 | 5 | 17 | 5 | 7 | 5 |
| 98 | 5 | 18 | 5 | 8 | 5 |
| 99 | 5 | 19 | 5 | 9 | 5 |
| 100 | 5 | 20 | 5 | 10 | 5 |
| 101 | 6 | 1 | 6 | 1 | 6 |
| 102 | 6 | 2 | 6 | 2 | 6 |
| 103 | 6 | 3 | 6 | 3 | 6 |
| 104 | 6 | 4 | 6 | 4 | 6 |
| 105 | 6 | 5 | 6 | 5 | 6 |
| 106 | 6 | 6 | 6 | 6 | 6 |
| 107 | 6 | 7 | 6 | 7 | 6 |
| 108 | 6 | 8 | 6 | 8 | 6 |
| 109 | 6 | 9 | 6 | 9 | 6 |
| 110 | 6 | 10 | 6 | 10 | 6 |
| 111 | 6 | 11 | 6 | 1 | 6 |
| 112 | 6 | 12 | 6 | 2 | 6 |
| 113 | 6 | 13 | 6 | 3 | 6 |
| 114 | 6 | 14 | 6 | 4 | 6 |
| 115 | 6 | 15 | 6 | 5 | 6 |
| 116 | 6 | 16 | 6 | 6 | 6 |
| 117 | 6 | 17 | 6 | 7 | 6 |
| 118 | 6 | 18 | 6 | 8 | 6 |
| 119 | 6 | 19 | 6 | 9 | 6 |
| 120 | 6 | 20 | 6 | 10 | 6 |
| 121 | 7 | 1 | 7 | 1 | 7 |
| 122 | 7 | 2 | 7 | 2 | 7 |
| 123 | 7 | 3 | 7 | 3 | 7 |
| 124 | 7 | 4 | 7 | 4 | 7 |
| 125 | 7 | 5 | 7 | 5 | 7 |
| 126 | 7 | 6 | 7 | 6 | 7 |
| 127 | 7 | 7 | 7 | 7 | 7 |
| 128 | 7 | 8 | 7 | 8 | 7 |
| 129 | 7 | 9 | 7 | 9 | 7 |
| 130 | 7 | 10 | 7 | 10 | 7 |
| 131 | 7 | 11 | 7 | 1 | 7 |
| 132 | 7 | 12 | 7 | 2 | 7 |
| 133 | 7 | 13 | 7 | 3 | 7 |
| 134 | 7 | 14 | 7 | 4 | 7 |
| 135 | 7 | 15 | 7 | 5 | 7 |
| 136 | 7 | 16 | 7 | 6 | 7 |
| 137 | 7 | 17 | 7 | 7 | 7 |
| 138 | 7 | 18 | 7 | 8 | 7 |
| 139 | 7 | 19 | 7 | 9 | 7 |
| 140 | 7 | 20 | 7 | 10 | 7 |
| 141 | 8 | 1 | 8 | 1 | 8 |
| 142 | 8 | 2 | 8 | 2 | 8 |
| 143 | 8 | 3 | 8 | 3 | 8 |
| 144 | 8 | 4 | 8 | 4 | 8 |
| 145 | 8 | 5 | 8 | 5 | 8 |
| 146 | 8 | 6 | 8 | 6 | 8 |
| 147 | 8 | 7 | 8 | 7 | 8 |
| 148 | 8 | 8 | 8 | 8 | 8 |
| 149 | 8 | 9 | 8 | 9 | 8 |
| 150 | 8 | 10 | 8 | 10 | 8 |
| 151 | 8 | 11 | 8 | 1 | 8 |
| 152 | 8 | 12 | 8 | 2 | 8 |
| 153 | 8 | 13 | 8 | 3 | 8 |
| 154 | 8 | 14 | 8 | 4 | 8 |
| 155 | 8 | 15 | 8 | 5 | 8 |
| 156 | 8 | 16 | 8 | 6 | 8 |
| 157 | 8 | 17 | 8 | 7 | 8 |
| 158 | 8 | 18 | 8 | 8 | 8 |
| 159 | 8 | 19 | 8 | 9 | 8 |
| 160 | 8 | 20 | 8 | 10 | 8 |
| 161 | 9 | 1 | 9 | 1 | 9 |
| 162 | 9 | 2 | 9 | 2 | 9 |
| 163 | 9 | 3 | 9 | 3 | 9 |
| 164 | 9 | 4 | 9 | 4 | 9 |
| 165 | 9 | 5 | 9 | 5 | 9 |
| 166 | 9 | 6 | 9 | 6 | 9 |
| 167 | 9 | 7 | 9 | 7 | 9 |
| 168 | 9 | 8 | 9 | 8 | 9 |
| 169 | 9 | 9 | 9 | 9 | 9 |
| 170 | 9 | 10 | 9 | 10 | 9 |
| 171 | 9 | 11 | 9 | 1 | 9 |
| 172 | 9 | 12 | 9 | 2 | 9 |
| 173 | 9 | 13 | 9 | 3 | 9 |
| 174 | 9 | 14 | 9 | 4 | 9 |
| 175 | 9 | 15 | 9 | 5 | 9 |
| 176 | 9 | 16 | 9 | 6 | 9 |
| 177 | 9 | 17 | 9 | 7 | 9 |
| 178 | 9 | 18 | 9 | 8 | 9 |
| 179 | 9 | 19 | 9 | 9 | 9 |
| 180 | 9 | 20 | 9 | 10 | 9 |
| 181 | 10 | 1 | 10 | 1 | 10 |
| 182 | 10 | 2 | 10 | 2 | 10 |
| 183 | 10 | 3 | 10 | 3 | 10 |
| 184 | 10 | 4 | 10 | 4 | 10 |
| 185 | 10 | 5 | 10 | 5 | 10 |
| 186 | 10 | 6 | 10 | 6 | 10 |
| 187 | 10 | 7 | 10 | 7 | 10 |
| 188 | 10 | 8 | 10 | 8 | 10 |
| 189 | 10 | 9 | 10 | 9 | 10 |
| 190 | 10 | 10 | 10 | 10 | 10 |
| 191 | 10 | 11 | 10 | 1 | 10 |
| 192 | 10 | 12 | 10 | 2 | 10 |
| 193 | 10 | 13 | 10 | 3 | 10 |
| 194 | 10 | 14 | 10 | 4 | 10 |
| 195 | 10 | 15 | 10 | 5 | 10 |
| 196 | 10 | 16 | 10 | 6 | 10 |
| 197 | 10 | 17 | 10 | 7 | 10 |
| 198 | 10 | 18 | 10 | 8 | 10 |
| 199 | 10 | 19 | 10 | 9 | 10 |
| 200 | 10 | 20 | 10 | 10 | 10 |
| 201 | 11 | 1 | | | |
| 202 | 11 | 2 | | | |
| 203 | 11 | 3 | | | |
| 204 | 11 | 4 | | | |
| 205 | 11 | 5 | | | |
| 206 | 11 | 6 | | | |
| 207 | 11 | 7 | | | |
| 208 | 11 | 8 | | | |
| 209 | 11 | 9 | | | |

TABLE 2-continued

| 1-hidden layer | 2-hidden layer | 3-hidden layer |
|---|---|---|
| 210 | 11 | 10 |
| 211 | 11 | 11 |
| 212 | 11 | 12 |
| 213 | 11 | 13 |
| 214 | 11 | 14 |
| 215 | 11 | 15 |
| 216 | 11 | 16 |
| 217 | 11 | 17 |
| 218 | 11 | 18 |
| 219 | 11 | 19 |
| 220 | 11 | 20 |
| 221 | 12 | 1 |
| 222 | 12 | 2 |
| 223 | 12 | 3 |
| 224 | 12 | 4 |
| 225 | 12 | 5 |
| 226 | 12 | 6 |
| 227 | 12 | 7 |
| 228 | 12 | 8 |
| 229 | 12 | 9 |
| 230 | 12 | 10 |
| 231 | 12 | 11 |
| 232 | 12 | 12 |
| 233 | 12 | 13 |
| 234 | 12 | 14 |
| 235 | 12 | 15 |
| 236 | 12 | 16 |
| 237 | 12 | 17 |
| 238 | 12 | 18 |
| 239 | 12 | 19 |
| 240 | 12 | 20 |
| 241 | 13 | 1 |
| 242 | 13 | 2 |
| 243 | 13 | 3 |
| 244 | 13 | 4 |
| 245 | 13 | 5 |
| 246 | 13 | 6 |
| 247 | 13 | 7 |
| 248 | 13 | 8 |
| 249 | 13 | 9 |
| 250 | 13 | 10 |
| 251 | 13 | 11 |
| 252 | 13 | 12 |
| 253 | 13 | 13 |
| 254 | 13 | 14 |
| 255 | 13 | 15 |
| 256 | 13 | 16 |
| 257 | 13 | 17 |
| 258 | 13 | 18 |
| 259 | 13 | 19 |
| 260 | 13 | 20 |
| 261 | 14 | 1 |
| 262 | 14 | 2 |
| 263 | 14 | 3 |
| 264 | 14 | 4 |
| 265 | 14 | 5 |
| 266 | 14 | 6 |
| 267 | 14 | 7 |
| 268 | 14 | 8 |
| 269 | 14 | 9 |
| 270 | 14 | 10 |
| 271 | 14 | 11 |
| 272 | 14 | 12 |
| 273 | 14 | 13 |
| 274 | 14 | 14 |
| 275 | 14 | 15 |
| 276 | 14 | 16 |
| 277 | 14 | 17 |
| 278 | 14 | 18 |
| 279 | 14 | 19 |
| 280 | 14 | 20 |
| 281 | 15 | 1 |
| 282 | 15 | 2 |
| 283 | 15 | 3 |
| 284 | 15 | 4 |
| 285 | 15 | 5 |
| 286 | 15 | 6 |
| 287 | 15 | 7 |
| 288 | 15 | 8 |
| 289 | 15 | 9 |
| 290 | 15 | 10 |
| 291 | 15 | 11 |
| 292 | 15 | 12 |
| 293 | 15 | 13 |
| 294 | 15 | 14 |
| 295 | 15 | 15 |
| 296 | 15 | 16 |
| 297 | 15 | 17 |
| 298 | 15 | 18 |
| 299 | 15 | 19 |
| 300 | 15 | 20 |

The initial weights between each connection and bias of ANN were set at the beginning (randomized) and during the training the weights were adjusted by the learning function: Gradient descent with momentum weight/bias learning. The criterion used to stop the training phase in each ANN was when the root-mean-square error was less than 0.09 or when the correct classification rate was equal to or greater than 80%. The values of the biomarkers and clinical data were directly involved in the modification of the connection weights in the ANN model during training. To avoid overfitting, a 10-fold cross-validation was used.

The performance of the ANNs in the validation phase was evaluated using 600 subjects: 459 with a diagnosis of lung cancer and 141 without lung cancer. The ROC curve was plotted and the AUC, sensitivity and specificity were calculated. The sensitivity of the ANN with the best combination of biomarkers was compared with any biomarker high. In addition, multivariate logistic regression (MLR) using only the biomarkers and another MLR employing both a combination of biomarkers and clinical parameters was plotted. The comparison was carried out in basis to Receiver Operating Characteristic (ROC) curves at a specificity of relevant clinical value (80%).

Thirteen ANNs from 800 ANNs with different architectures showed the best results. From these thirteen ANNs, the ANNs named net, net4, net5, net6, net9 and net11 with different hidden layers and numbers of neurons/nodes were tested using the entire dataset of 600 subjects: 459 with diagnosis of lung cancer and 141 without lung cancer. A summary of the best performing neural nets are provided in the following Table 3:

TABLE 3

| Name of ANN | net | net2 | net3 | net4 | net5 | net6 | net7 |
|---|---|---|---|---|---|---|---|
| Architecture of the best ANNs | 5 | 5 | [5, 10, 5] | 5, 20 | 6, 20 | 10, 20 | 1 |
| AUC obtained to the best ANNs | 0.9204 | 0.9297 | 0.9211 | 0.9973 | 0.966 | 0.979 | 0.8559 |

| Name of ANN | net8 | net9 | net10 | net11 | net12 | net13 |
|---|---|---|---|---|---|---|
| Architecture of the best ANNs | 1 | 1, 5, 1 | 6 | 6 | 3, 2 | 2, 3 |

TABLE 3-continued

| | | | | | |
|---|---|---|---|---|---|
| AUC obtained to the best ANNs | 0.8527 | 0.8535 | 0.9014 | 0.9295 | 0.853 | 0.858 |

The best ANN trained with the best classification performance in the test phase was net4 and had a configuration of 2-hidden layers with 5 and 20 neurons, respectively. This ANN correctly classified 89.3% (536 of 600 subjects). The area under the curve value was 0.91. The sensitivity at a specificity of 80% in the ROC curve for the ANN was 90.2% (see, e.g., FIG. 15D). See Table 1 for the Clinical Factors used and six biomarkers tested.

When the specificity was increased to 92.0%, the sensitivity was not compromised, and remained at a value of 88.0% (data not shown). The following Table 4 shows the number of correct and incorrect classification, AUC, sensitivity and specificity of the ANNs chosen for a data set (600 subjects).

TABLE 4

| | net | net4 | net5 | net6 | net9 | net11 |
|---|---|---|---|---|---|---|
| AUC | 0.72 | 0.91 | 0.82 | 0.85 | 0.74 | 0.76 |
| Test negative | | | | | | |
| Incorrect | 69 | 11 | 32 | 26 | 51 | 44 |
| Correct | 72 | 130 | 109 | 115 | 90 | 97 |
| Total controls | 141 | 141 | 141 | 141 | 141 | 141 |
| Test positive | | | | | | |
| Correct | 424 | 406 | 395 | 403 | 391 | 403 |
| Incorrect | 35 | 53 | 64 | 56 | 68 | 56 |
| Total Cancer | 459 | 459 | 459 | 459 | 459 | 459 |
| Sensitivity | 0.92 | 0.88 | 0.86 | 0.88 | 0.85 | 0.88 |
| Specificity | 0.51 | 0.92 | 0.77 | 0.81 | 0.64 | 0.68 |

This model was compared to other models, see, e.g., FIGS. 15A-15C, and Example 4.

Example 4

Comparison of Statistical Models to ANN

According to embodiments of the present invention, a variety of statistical and machine learning approaches were utilized to classify individuals as having lung cancer or not having lung cancer (FIGS. 15A-15D). At 80% specificity, sensitivities were determined for assessing a patient's likelihood of having cancer based on a single biomarker, e.g., referred to as Any Biomarker High. For example, sensitivity was relatively low using this method, e.g., for a given biomarker, the sensitivity was found to be 51% (FIG. 15A). In this model any of the measured biomarkers, such as those of Table 6, when above a literature recognized threshold for being indicative of the presence of cancer are deemed "Any Marker High" and the patient is categorized as having cancer. For example, the cut off values for the biomarkers of Table 1 are: CEA>=5 ug/L; CYFRA 21-1>=3.3 ug/L; NSE>=25 ug/L; SCC>=2 ug/L; CA19-9>=37 u/mL and Pro-GRP>=50 ng/L.

In another embodiment, at 80% specificity, sensitivities were determined for assessing a patient's likelihood of having cancer based on six biomarkers and using multivariate logistic regression. See FIG. 15B. In this method, a line was used to divide a population of data points into two categories, based on the following equation $y=\beta_0+\beta_1 x_1+\beta_2 x_2 \ldots +\beta_n x_n$. Typically, sensitivity was relatively low using this method, e.g., for the six given biomarkers, the sensitivity was found to be 70.4%. In this case, the biomarkers were CA 19-9, CEA, Cyfra 21-1, NSE, Pro-GRP, SCC.

In another embodiment, at 80% specificity, sensitivities were determined for assessing a patient's likelihood of having cancer based on six biomarkers combined with clinical factors and using multivariate logistic regression. See FIG. 15C and Table 1 for the list of clinical factors and biomarkers. In this method, a line was used to divide a population of data points into two categories, based on the following equation $y=\beta_0+\beta_1 x_1+\beta_2 x_2 \ldots +\beta_n x_n$. Similar to the six biomarkers model, the sensitivity was relatively low (but better than only measuring the panel of six biomarkers) using this method, e.g., for the six given biomarkers and clinical factors, the sensitivity was found to be 75.6%. In this case, the biomarkers were CA 19-9, CEA, Cyfra 21-1, NSE, Pro-GRP, SCC, and the clinical factors were smoking status, packages years, patient age, family history of lung cancer, and recoded has symptoms.

In yet another embodiment, at 80% specificity, sensitivities were determined for assessing a patient's likelihood of having cancer based on six biomarkers combined with clinical factors and using an artificial neural network. See FIG. 15D. The neural net categorized patients as likely to have cancer or not likely to have cancer.

In this example, (see also, FIG. 15D and Example 5), a Feedforward, Pattern Recognition Neural Network was used to classify patients as likely or not likely to have lung cancer. Inputs to the ANN included the biomarkers: CA 19-9, CEA, Cyfra 21-1, NSE, Pro-GRP, SCC, and the clinical parameters: smoking status, package per year, patient age, family history of lung cancer, and when available recoded has symptoms. Outputs to the neural network were provided as (1) likely to have lung cancer and (2) not likely to have lung cancer. A marked improvement in sensitivity was achieved by this method, with the sensitivity being greater than 90%, and thus, better than any of the other methods of FIGS. 15A-15C. In embodiments, wherein a patient is deemed as likely to have lung cancer they are then recommended for diagnostic testing such as CT testing.

In summary, the ANN at a specificity of 80% increased the sensitivity by 39.2% as compared to Any Biomarker High (FIG. 15A) which had 51% sensitivity. The ANN at a specificity of 80% increased the sensitivity by 19.8% as compared to MLR combining only 6 biomarkers, which had 70.4% sensitivity. The ANN at a specificity of 80% increased the sensitivity by 14.6% as compared to MLR combining 6 biomarkers and clinical factors, which showed 75.6% sensitivity. The area under the curve values for ANN, Any Biomarker High, MLR (only biomarkers), MLR (biomarkers plus clinical factors) was 0.91, 0.76, 0.84, and 0.87, respectively.

Example 5

Identification of Novel Predictors of Disease

In some embodiments, the neural net can be used to identify novel predictors of a disease. For example, a novel biomarker or clinical factor or other type of input as disclosed in this application (e.g., from the literature, from the environment, etc.) may be selected as an input into a neural net, and it can be determined whether the novel input is predictive of lung cancer. In such cases, the novel input may have no known previous association with lung cancer.

For example, the novel input is selected as an input into a neural net system. The neural net is trained according to Example 3 and FIG. 14. It is determined whether the sensitivity increases, remains about the same, or decreases as compared to the neural net without the novel input. If the sensitivity increases, then the novel input may act as a predictor of the disease.

As a specific example, a secondary disease is selected as an input into a neural net system. See for example, Lung Cancer and peripheral vascular surgery (1983) Beachamp G. et al. Can J. Surg 26(5):472-4. The neural net is trained according to Example 3 and FIG. 14. It is determined whether the sensitivity increases, remains about the same, or decreases as compared to the neural net without the secondary disease. If the sensitivity increases, then the secondary disease may act as a predictor of the disease. Additionally, these techniques may be used to identify novel relationships between a disease such as lung cancer and diseases which correlate or co-exist with lung cancer.

For example, using the techniques presented herein may be used to determine that lung cancer and peripheral vascular disease are frequently correlated, e.g., a patient that has lung cancer is also likely to have peripheral vascular disease.

Example 6

Ranking Input Factors

In some embodiments, the neural net can be used to rank input factors for a disease, to identify which inputs are the most predictive of a disease. For example, any number of novel biomarkers, clinical factors, or other types of inputs as disclosed in this application (e.g., from the literature, from the environment, etc.) may be selected as input into a neural net (e.g., tens, hundreds, thousands), and the neural net can be used to determine which subset of inputs are the most predictive of lung cancer. In some cases, the most predictive inputs may have no known previous association or relationship to the disease, e.g., lung cancer.

TABLE B

Ranking of biomarkers and clinical factors for predicting lung cancer.

| | importance index |
|---|---|
| cyfra | 18.27887711 |
| cea | 17.70786983 |
| smoke_duration | 16.50408067 |
| nodule | 15.37358411 |
| nse | 10.77973493 |
| grp | 8.153103186 |
| age | 7.903903228 |
| scc | 6.183531192 |
| ca | 5.689815943 |
| smoke_status | 3.943065227 |
| cough | 3.199732643 |
| symptom | 2.623152619 |
| history | 1.613154169 |
| pack | 0.362940835 |
| Cigarette daily | 0.226657039 |

Example 7

Clinical Factors Plus Serum Biomarkers is Superior to Either Method Alone

Traditionally, physician judgment has formed the basis for lung cancer risk estimation, patient counseling, and decision making. However, clinicians' estimates are often biased due to both subjective and objective confounders. To mitigate this problem and to obtain more accurate lung cancer predictions, dozens of multi-biomarker panels have been developed over the last decade to better estimate the presence of lung cancer.

According to the embodiments presented herein, it has been found that cognitive computing/machine learning approaches models further improve discrimination accuracy in Lung Cancer Risk Estimation.

Statistical models can provide assistance in processing a large number of variables (biomarker values and clinical factors). Several different statistical methods have been applied to discriminate between patients with and without lung cancer, such as multivariate logistic regression (MLR), random forest (RF), classification and regression trees, support vector machine (SVM), etc. These methods have been used to develop algorithms that combine measurements of the most predictive biomarkers in a panel to achieve the highest diagnostic accuracy. It is a goal of present invention embodiments to develop a biomarker panel in combination with clinical factors, which may include additional inputs as well, which is cost-effective and can be deployed worldwide, even in areas of the world with medical systems constrained by costs using machine learning technology (e.g., neural networks or deep learning neural networks). Therefore, the development of a cost-effective platform would be beneficial.

The goals of the current study were to confirm the accuracy of a panel of biomarkers on an independent data set, to explore the accuracy relative to and in combination with clinical risk predictors with a focus on at risk patients relevant to lung cancer screening and to further investigate whether an advanced multi-parameter statistical algorithm can materially improve diagnostic accuracy of our lung cancer test.

Methods

Training Set Serum Samples.

All of the cancer and normal control samples used in the training set were IRB-approved, consented serum samples that were purchased from the Clinical Research Center of Cape Cod, Inc. (Cape Cod, MA), Asterand (Detroit, MI), Indivumed (Germany) or Bioreclamation IVT (New York, NY). All of the lung cancer samples were collected at physicians' offices or hospitals.

All lung cancer and control serum samples were from patients 50 years of age or older who were current or former smokers with a smoking history of greater than 20 pack years and less than 15 years of smoking cessation. Diagnosis of the lung cancer cohort was confirmed from surgical pathology reports. The control group had no evidence of current or prior cancer.

Testing Set Serum Samples.

All of the cancer and normal control samples used in the testing set were obtained from an IRB approved blood biorepository at the Cleveland Clinic. All patients had provided written informed consent. All lung cancer cases were biopsy confirmed and untreated. Control patient samples were obtained from patients attending the lung cancer screening clinic or general Pulmonary clinic.

Sample Analysis.

Multiplex magnetic bead-based immunoassay of CEA, CYFRA21-1, CA125 and HGF in patient sera was performed using reagents from EMD Millipore, Inc. as previously described (Mantovani et al., Chemo-radiotherapy in lung cancer: state of the art with focus on the elderly population. Ann Oncol. 2006; 17 (Suppl 2): ii 61-63.6.). The MILLIPLEX® MAP Human Circulating Cancer Biomarker Magnetic Bead Panel I was used. Four tumor proteins (CEA, CYFRA21-1, CA125 and HGF) were measured using the MAGPIX® instrument (Luminex Corporation, Austin, TX) as previously described [Moyer V A; US Preventive Services Task Force. Screening for lung cancer: US Preventive Services Task Force recommendation statement. Ann Intern Med. 2014; 160(5):330-338]. Using Median Fluorescent Intensity (MFI) values and a five-parameter logistic curve fitting method (xPONENT® software for the MAGPIX®) the concentrations of each tumor protein in the samples were calculated. The calculated protein concentration values were used for the subsequent analysis.

NY-ESO1 autoantibody detection was performed using an immunoassay developed at 20/20 Gene Systems, MD and the MAGPIX® reader as previously described [Id.]. Background subtracted MFI values were used for the subsequent analysis.

Statistical Analysis.

The study cohort was divided into two groups based upon the outcome of cancer or control. The demographics, comorbidities, and cancer characteristics were described using sample mean with standard deviation or proportion as appropriate.

Multivariate logistic regression analysis: To determine the direction and statistical significance of the effect of each biomarker on the outcome, we performed multivariate logistic regression (MLR) analysis for the full data set. Each MLR model included the five biomarkers. The AUC was calculated for the ROC curves that were constructed based on the models. Exploratory MLR analyses were performed on the testing set, divided by stage and histology, and after including clinical variables. Clinical variables included age, sex, a clinical diagnosis of COPD, and smoking history.

Random forests analysis: Random Forest (RF) models were used to identify the variables that were associated with and predictive of cancer (Bach P B, Mirkin J N, Oliver T K, Azzoli C G, Berry D A, Brawley O W, et al. Benefits and harms of CT screening for lung cancer: a systematic review. JAMA. 2012; 307(22):2418-29. doi: 10.1001/jama.2012.552). To avoid the possible overfitting of the MLR models, we used the repeated random-split cross-validation procedure (Croswell J M, Kramer B S, Kreimer A R, Prorok P C, Xu J L, Baker S G, et al. Cumulative incidence of false-positive results in repeated, multimodal cancer screening. Ann Fam Med. 2009; 7:212-22). Specifically, we randomly split the data into training (70%) and validation (30%) sets 100 times. The RF model was built on each training set and then evaluated on the corresponding test set. The validation results were reported as the average performance over all test sets. Exploratory RF analyses were performed on the testing set, divided by stage and histology, and after including clinical variables (as above).

Results

The training set consisted of 604 patient samples (268 with lung cancer, 336 controls). 151 of those with lung cancer (56.3%) had adenocarcinoma and 144 of the 268 lung cancers (53.7%) were stage I. The testing set consisted of 400 patient samples (155 with lung cancer, 245 controls). 74 (47.7%) of those with lung cancer had adenocarcinoma and 52 of the 155 lung cancers (33.5%) were stage I (Table 5).

TABLE 5

Clinical characteristics of the cancer and control patients in the training and testing sets

| | Training (604) | | Validation (400) | |
| --- | --- | --- | --- | --- |
| | Cancer (268) | Control (336) | Cancer (155) | Control (245) |
| Age | 64.0 | 64.5 | 65.3 | 68.3 |
| Sex (% F) | 43.7 | 39.9 | 40 | 51.9 |
| Smoking (C/F/N) | N/A | N/A | 20/129/6 | 95/142/7 |
| Pack years | >20 | >20 | 43 | 35 |
| Adenocarcinoma (%) | 56.3 | | 47.7 | |
| Squamous (%) | 33.2 | | 39.4 | |
| Stage I (%) | 53.7 | | 33.5 | |
| Stage II (%) | 24.3 | | 12.3 | |
| Stage III (%) | 17.9 | | 37.4 | |
| Stage IV (%) | 4.1 | | 16.8 | |

Training set results showed that combination of the biomarkers studied was more accurate than the individual biomarkers considered alone (panel AUC 0.80 vs. individual AUC 0.45-0.71). A logistic regression model was built on the training set using the biomarker values and then applied to the validation set. The diagnostic accuracy of the 4 biomarker panel in the validation set was comparable with that of the training set (AUC 0.81).

There was less meta-data available for the training samples for the algorithm development that combines clinical factors and biomarkers values. Therefore, to evaluate an algorithmic approach that combines biomarker and clinical data further analyses were performed only on the validation set samples (n=400).

TABLE 6

Logistic Regression (LR) and Random Forest (RF) model performance using biomarker panels and clinical factors

| | LR | Random Forest model (70:30 Split) | | |
| --- | --- | --- | --- | --- |
| Variable | model AUC* | Sensitivity (%) | Specificity (%) | AUC* |
| Clinical factors | 0.68 | 34 | 85 | 0.66 |
| Biomarkers | 0.81 | 66 | 86 | 0.84 |
| Combined | 0.86 | 80 | 80 | 0.87 |

In exploratory analysis, a Multivariate Logistic Regression (MLR) model built from clinical variables in the validation set (age, sex, COPD, smoking history) had an AUC of 0.68. When combined with the 4 biomarker panel the AUC was 0.86 (Table 6). Similarly, Random Forest (RF) modeling of the clinical factors and biomarker values alone yielded an average AUC of 0.66 and 0.84, respectively. When combined with the 4 biomarker panel, the AUC improved to 0.87 (Table 6).

The validation sample set from the Cleveland Clinic (n=400) has a significant number of samples that did not conform to the indication criteria of either the USPTF or PAULAs Test. "PAULAs test" (an acronym for Protein Analytes Used for Lung cancer Algorithms) measures the levels of serum antigens, an autoantibody, and several clinical factors including patient age, smoking history, and prior lung disease. The test is intended to be used as an initial screen for non-small cell lung cancer (NSCLC) in asymptomatic individuals from a high-risk population (e.g. 20 pack-year current smokers or past smokers who quit less than 15 years ago, and are over the age of 50) who are not receiving annual CT scans Specifically, samples are included with variations in smoking history, including some never smokers. Some patients have smoking histories with less than 20 pack years (and <30 pack years as per USPTF). Some patients are under age 50 (and under age 55 or over age 80 as per USPTF).

Using random forest statistical analysis we evaluated the improvements yielded by single predictor and identified the panel of classifiers that seem most significant out of both the biomarkers and the clinical factors: CEA, CA-125, CYFRA and NYESO-1, age, smoking history, pack years and COPD. The performance of this panel in the population conforming to PAULAs test inclusion criteria (e.g. 20 pack-year current smokers or past smokers who quit less than 15 years ago, and are over the age of 50) was better than in a broader population that included smokers under age 50 and with less than 20 pack years (Table 7). At approximately the same specificity (79% vs 80%) the sensitivity falls from 81% to 74% in a broader population. It should be noted, however, that sample size (400 vs 216) may also effect the difference between the results.

TABLE 7

Performance of the test in the population within PAULAs test inclusion criteria and in a broader population.

| | Cohort size | AUC* | Sensitivity % | Specificity % |
| --- | --- | --- | --- | --- |
| All patients | n = 400 | 0.845 | 74 | 79% |
| Patients within PAULAs test inclusion criteria | n = 216 | 0.887 | 80 | 80 |

Figure 16A:
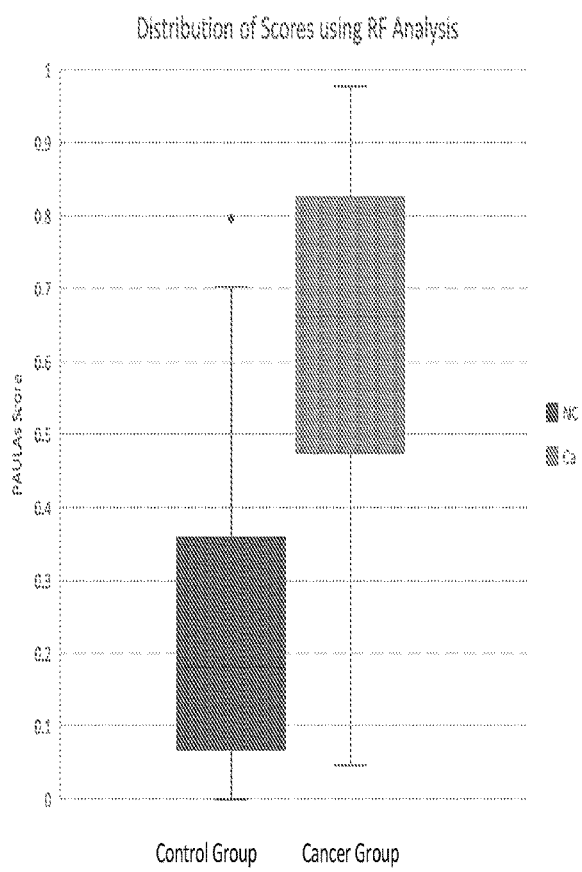
FIGS. 16A and 16B show the distribution of test scores in a patient cohort conforming to specific test inclusion criteria (older than 50 years, current and former smokers, greater than 20 pack years) using random forest analysis on a panel of markers (age, smoking status, pack years, COPD, CA-125, CEA, CYFRA and anti-NYESO), in accordance with example embodiments.
Figure 16B:
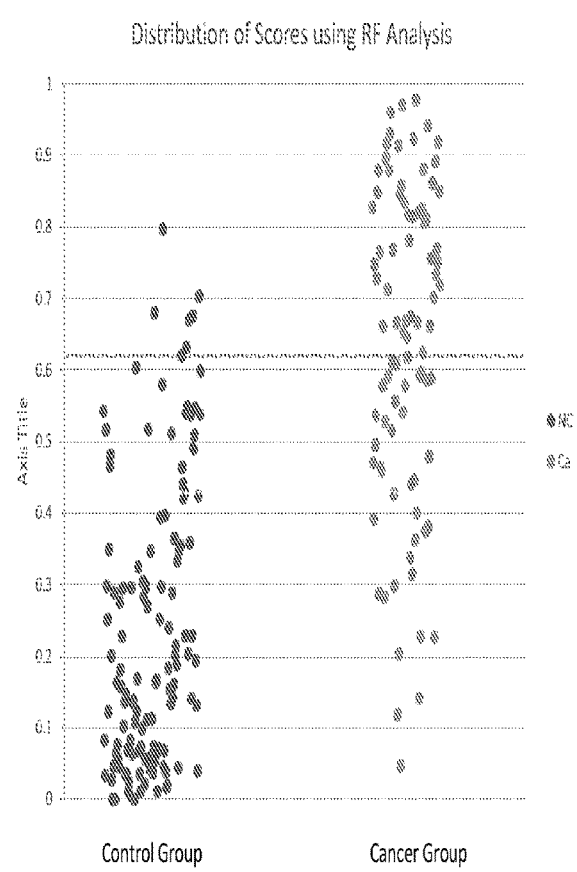

FIG. 16A-16B shows the distribution of test scores in a patient cohort conforming to PAULAs test inclusion criteria. For this analysis, we excluded never smokers and those with missing info, and limited the patient cohort to the PAULA's test inclusion criteria. These figures show distribution of PAULAs test scores using RF model (CEA, CA-125, CYFRA and NYESO-1, age, smoking history, pack years and COPD): 16A. box-and whiskers plot. 16B. scatter dot plot. The horizontal line in FIG. 16B shows the PAULAs test cut-off of 0.43 derived from the validation set results.

TABLE 8

Performance of the combined biomarker-clinical factors panel by lung cancer stage.

| | Sensitivity (%) at 80% Specificity | |
| --- | --- | --- |
| | All patients | Patients within PAULAs test inclusion criteria |
| I | 69.6% | 82.4% |
| II | 70.6% | 84.6% |
| III | 63.0% | 75.0% |
| IV | 82.4% | 90.0% |

Using the test cutoff that corresponds to 80% fixed specificity (0.43), we evaluated the accuracy of the combined panel by stage in both groups of patients. The detection sensitivity of the early stages (I and II) in patients corresponding to PAULAs test inclusion criteria was higher than in a broader population—83.5% vs 70.1% (Table 8).

We also explored deep neural network (DNN) modelling approaches for the test performance evaluation using the entire validation set from Cleveland Clinic (n=400). To build a DNN model, we first identified the input variables, which included both clinical factors and biomarkers. We then applied 2 hidden layers, 1000 nodes in the first layer, and 5000 nodes in the second layer. Tanh activation function was adopted in the DNN method. With 70% data points as the training dataset and 30% of data points as testing set, the DNN model produced a higher AUC (0.89) than random forest (0.88) and logistic regression (0.87) models (Table 9).

TABLE 9

Comparison of PAULAs test results using biomarkers and clinical variables and different modelling approaches (LR, RF and DNN)

| Method | AUC* | 95% CI# | Sensitivity, % | Specificity, % |
| --- | --- | --- | --- | --- |
| Logistic Regression | 0.86 | 0.80-0.94 | 75 | 80 |
| Random Forest | 0.88 | 0.81-0.95 | 80 | 80 |
| Deep learning (DNN) | 0.89 | 0.83-0.96 | 90 | 82 |

DISCUSSION

The current study validated the clinical accuracy of a combined protein and antibody panel in a population at risk of having lung cancer and explore the impact of combining clinical and biomarker variables on test accuracy. The intended use population for this study was patients at risk of having lung cancer. The results suggested that the combination of markers is more accurate than any of the markers alone. In exploratory analysis, the highest accuracy was achieved by combining clinical features and biomarker results for patients within PAULAs test inclusion criteria (50 years of age or older who were current or former smokers with a smoking history of greater than 20 packs per year and less than 15 years of smoking cessation). Based on the Random Forest statistical algorithm the test yielded the following performance: 80% sensitivity, 80% specificity, 0.88 AUC when both biomarker values (CEA, CYFRA, CA125 and NY-ESO1) and clinical factors (age, smoking history, pack-years and COPD status) were considered.

To pursue clinical utility testing it should be determined if the results of this study support further development of this biomarker as an early detection tool. The accuracy of the test should support the potential application. To estimate the accuracy required to justify investment in a clinical utility study, a formula has been suggested that incorporates the accepted benefit: harm balance of current standard practice [(Pepe M S, Janes H, Li C I, Bossuyt P M, Feng Z, Hilden J. Early-phase studies of biomarkers: What target sensitivity and specificity values might confer clinical utility? Clin Chem 2016; 62(5):737-742.) If we use this formula to determine a test accuracy that would allow us to use the results of this test to select patients for lung cancer screening from a population with a 0.2% incidence of lung cancer, and assume that we currently accept screening a population with a 0.83% incidence of lung cancer (the incidence during the screening years of the National Lung Screening Trial [The National Lung Screening Trial Research Team. Reduced lung-cancer mortality with low-dose computed tomographic screening. N Engl J Med. 2011; 365:395-409. doi: 10.1056/NEJMoa1102873]), TPR (True positive rate, or Sensitivity)/FPR (False positive rate, or (1-Specificity)) of the test would have to be at least 4. Based on this analysis, the accuracy of the biomarker panel in the current study (e.g. sensitivity of 80% at specificity of 80% (RF model) or sensitivity of 90% at specificity of 82% (DNN model) met the minimal biomarker panel performance (TPR/FPR=4) to support further development of the test as a screening tool. In addition, the cost of this test would be much lower than most omics-based testing platforms currently available. This is also important to consider when developing a screening test.

We also have developed a risk categorization tool based on the results from this study. This test generates a composite score from the Random Forest model comprising 4 clinical parameters and the levels of 4 biomarkers in patient serum. This score is an indicator of the level of risk for each patient of currently having lung cancer relative to others with a comparable smoking history. Using two cutoffs (0.43 and 0.62), the test results were broken down into three separate categories with increasing risk factors (Table 10). Table 10 indicated the probability of lung cancer for patients in a given score range at the time of testing. Positive predictive value (PPV) is the probability that a person with a positive test score above the chosen cutoff truly has the disease. Unlike sensitivity and specificity, the PPV is dependent on the population being tested and is influenced by the prevalence of the disease. For the PPV calculation we used 0.83% lung cancer prevalence from the NLST study [The National Lung Screening Trial Research Team. Reduced lung-cancer mortality with low-dose computed tomographic screening. N Engl J Med. 2011; 365:395-409.]. Table 10 shows that the higher patient's score on PAULAs test the greater the likelihood that this patient has cancer.

TABLE 10

Test PPV in 3 separate score categories

| Score Range | Sensitivity | Specificity | PPV |
|---|---|---|---|
| X ≥ 0.62 | 55.1% | 95.3% | 8.89% |
| 0.43 ≤ X < 0.62 | 62.2% | 84.0% | 3.16% |
| X < 0.43 | 100.0% | 0.0% | 0.83% |

Below the cutoff of 0.43, the test will not differentiate between cancer and non-cancer. Individuals whose scores fell within this range had the same likelihood of having lung cancer as those people currently recommended for LCDT by the USPTF (0.83%). Individuals whose scores fell within the middle range were 3.8× more likely to have lung cancer than individuals currently recommended for LCDT by the USPTF. Finally, individuals whose scores fell within the high range were 10.7× more likely to have lung cancer than individuals currently recommended for LCDT by the USPTF (US Preventative Services Task Force). The result of the test presented using such categorization table will inform the physician about the degree of the lung cancer risk a patient has after a positive result on the test.

The strengths of the current study included a reasonably large number of samples from a cohort relevant to the potential clinical application, with samples obtained from more than one source. The sample sets included a substantial portion of cases with early stage disease, and a diverse set of relevant patient comorbidities, supporting the robustness of the method. The results were compared to, and were more accurate than clinical prediction, and the combination of the marker results with clinical features improved the accuracy of both. Exploratory analysis was performed on only the validation set from the Cleveland Clinic.

In summary, this study validated the accuracy of a panel of proteins and an autoantibody in a population relevant to lung cancer screening, and suggested a benefit to combining clinical features with the biomarker results.

Example 8

Study of Lung Cancer Biomarker Expression and Clinical Parameter Variables

The National Lung Screening Trial ("NLST") showed that a low-dose CT (LDCT) screening program could reduce disease-specific mortality in high-risk patients by 20% and overall mortality by 7%, which proved that early lung cancer detection saves lives (and is believed to reduce lifetime disease-specific medical costs) [The National Lung Screening Trial Research Team. Reduced lung-cancer mortality with low-dose computed tomographic screening. N Engl J Med. 2011; 365:395-409. doi: 10.1056/NEJMoa1102873]. However, the major LDCT drawbacks include a high false-positive rate and the inability to unambiguously distinguish benign nodules that can involve expensive invasive follow-up procedures [Bach P B, Mirkin J N, Oliver T K, Azzoli C G, Berry D A, Brawley O W, et al. Benefits and harms of CT screening for lung cancer: a systematic review. JAMA. 2012: 307(22):2418-29; Croswell J M, Kramer B S, Kreimer A R, Prorok P C. Xu J L, Baker S G, et al. Cumulative incidence of false-positive results in repeated, multimodal cancer screening. Ann Fam Med. 2009; 7:212-22; Wood D E, Eapen G A, Ettinger D S, et al. Lung cancer screening. J Natl Cancer Compr Netw 2012; 10:240-265]. False-positive LDCT results occur in a substantial proportion of screened persons; 95% of all positive results do not lead to a diagnosis of cancer. Most pulmonary experts believe that biomarker testing is required to compliment radiographic screening as LDCT achieves its eventual steady-state utilization.

A cohort of 459 subjects of current and former (stopped within the last 15 years) smokers with pulmonary nodules and confirmed lung cancer (lung cancer test group), and 139 matched controls with confirmed benign lung nodules participated in the current study. All participants were 50 years or older with a 20 pack year, or more, smoking history. All subjects donated blood within 6 weeks of radiographic screening to be used for measurement of biomarkers. Radiographic screening was used to characterize the pulmonary nodules including size and number. The associated patient information comprised the ages, genders, races, final diagnoses including stage of lung cancer and histological type, family history of lung cancer, pack years, packs per day (e.g. smoking intensity), smoking duration (years), smoking status, symptoms, cough (yes or no) and blood in sputum.

Demographic and Clinical Information

For the control group the medium age was 58 years, 91% were male (9% female), 50% were asymptomatic and 9% had a family history of lung cancer. For the test group (confirmed lung cancer) the medium age was 62, 91% were male (9% female), 43% were asymptomatic and 8% had a family history of lung cancer. The smoking history between the test and control groups were similar with both groups having a median pack year of 40. In the control group 87% were current smokers with a median age of quitting at 53.5 years and 3 years since quitting, as compared to 89% in the test group with a median age of quitting at 60 and 4 years since quitting. In the lung cancer group, 44% were staged as early (stage I and II) and 56% as late (stages III and IV). The lung cancer was typed as adenocarcinoma 40%, squamous 34%, small cell 19%, large cell 4% and other 3%.

The serum biomarkers were measured using commercially available reagents and immunoassay techniques from Roche Diagnostics. The measured biomarkers included CEA, CA 19-9, CYFRA 21-1, NSE, SCC, and ProGRP and levels were reported as test values. The obtained clinical parameters included family history of lung cancer, nodule size, pack years, packs per day (or smoking intensity), patient age at time of study, smoking duration (years), smoking status, cough (binary), blood.

TABLE 11

Benign Nodules (Control group)

| Biomarker | Median (protein or unit) |
|---|---|
| CA 19-9 | 9 |
| CEA | 2 |
| CYFRA | 2 |
| NSE | 11 |
| Pro-GRP | 34 |
| SCC | 1 |

TABLE 12

Lung Cancer (Test group)

| Biomarker | Median (protein or unit) |
|---|---|
| CA 19-9 | 11 |
| CEA | 4 |
| CYFRA | 4 |
| NSE | 13 |
| Pro-GRP | 37 |
| SCC | 1 |

Analysis

Each of those variables (biomarkers or clinical parameters) was analyzed in a univariate logistic regression model and together in a multivariate logistic regression model. The variable analysis is provided below as area under the curve (AUC) of receiver operating characteristic (ROC) curves.

TABLE 13

Biomarker and clinical parameter analysis

| Model | Variable(s) | AUC |
|---|---|---|
| univariate | Nodule size | 0.69 |
| univariate | Pack years | 0.50 |
| univariate | Packs per day (smoking intensity) | 0.53 |
| univariate | Patient Age at time of Study | 0.66 |
| univariate | Smoking Duration (years) | 0.57 |
| univariate | Blood | 0.51 |
| univariate | Cough (yes or no) | 0.59 |
| univariate | CA 19-9 | 0.58 |
| univariate | CEA | 0.69 |
| univariate | CYFRA | 0.75 |
| univariate | NSE | 0.68 |
| univariate | ProGRP | 0.60 |
| univariate | SCC | 0.60 |
| Multivariate | CEA, CYFRA, NSE, ProGRP, nodule size, patient age, smoking duration (years) and cough (yes or no) | 0.87 |

The biomarkers were further analyzed comparing a 6-marker panel and a 5-marker panel with and without clinical parameters. The AUC value calculated from the biomarker panel and the clinical parameter panel was compared to the biomarker panel plus the clinical parameters demonstrating an improvement with the addition of the clinical parameter variables into the multivariate logistic regression model analysis. Of the biomarkers tested, four contribute to the analysis for distinguishing benign from malignant nodules; they are CEA, CYFRA, NSE and Pro-GRP. Of the clinical parameters tested, six contribute to the multivariate analysis for distinguishing benign from malignant nodules; they are patient age, smoking status, smoking history (including pack years, smoking duration in years and smoking intensity), chest symptoms (such as thoracalgia, blood in sputum, chest tightness), cough and nodule size.

TABLE 14

6-biomarker Panel and Clinical Parameter Analysis

| Model | AUC | Sensitivity at 80% Specificity | Sensitivity at 90% Specificity |
|---|---|---|---|
| Individual Markers | | | |
| CA19-9 | 0.58 | | |
| CEA | 0.69 | | |
| CYFRA | 0.75 | | |
| NSE | 0.68 | | |
| SCC | 0.60 | | |
| ProGRP | 0.60 | | |
| Clinical Parameters Only | 0.75 | 53.9% | 30.5% |
| 6-marker Panel[1] | 0.83 | 71.8% | 59.6% |
| 6-marker panel[2] | 0.84 | 70.5% | 64.7% |
| 6-marker panel + 7 clinical parameters[3] | 0.87 | 74.3% | 66.9% |
| 4 Best Markers + 6 Best Clinical parameters[4] | 0.87 | 75.8% | 70.2% |

TABLE 15

5-Biomarker Panel and Clinical Parameters Analysis

| Model | AUC | Sensitivity at 80% Specificity | Sensitivity at 90% Specificity |
|---|---|---|---|
| Individual Markers | | | |
| CA19-9 | 0.58 | | |
| CEA | 0.69 | | |
| CYFRA | 0.75 | | |
| NSE | 0.68 | | |
| SCC | 0.60 | | |
| Clinical Parameters Only | 0.75 | 53.9% | 30.5% |
| 5-marker panel[5] | 0.82 | 70.6% | 57.2% |
| 5-marker panel[6] | 0.84 | 68.8% | 63.8% |
| 5-marker panel + 7 clinical parameters | 0.87 | 74.7% | 64.2% |
| 3 Best Markers + 6 Best Clinical Parameters | 0.87 | 75.6% | 68.4% |

[1]Values normalized using MOM method
[2]Multivariate logistic regression analysis
[3]Age, Smoking Status, Smoking history (pack years and packs per day), chest symptoms, cough, family history of lung cancer and nodule size.
[4]Step-wise MLR analysis; CEA, CYFRA, NSE and Pro-GRP; Age, smoking status, pack years, chestsymptoms, cough and nodule size Example 9

A Multi-Marker Algorithm for Distinguishing Benign Vs Malignant Pulmonary Nodules The cohort of 459 subjects of current and former (stopped within the last 15 years) smokers with pulmonary nodules from Example 1 was expanded to a total cohort of 1005 subjects, wherein the objectives of this study were to screen a large amount of existing data in a cost effective and rapid approach for risk assessment algorithm development and to demonstrate the importance of using algorithms to generate results from a panel of markers rather than the "any marker high" method. We also explored using advanced machine learning models to classify lung nodules as benign or malignant. Herein, we report the development of models and calculators for predicting the probability of lung cancer in pulmonary nodules using data from LDCT screening cohort (n=1005).

Data from a cohort of 1005 subjects with radiographically apparent pulmonary nodules were obtained and analyzed as disclosed below and in Example 8, wherein 502 participants had malignant nodules "cancer" and 503 participants were a "control" group with begin nodules. The collected data was blinded prior to analysis. All subjects chosen for inclusion in the study were: a) age 50-80 at the time of initial evaluation; b) 20+ pack-year smokers, and c) current smokers or smokers that quit within the last 15 years and included both, symptomatic and asymptomatic subjects. All subjects were tested for the following cancer biomarkers: CEA, CYFRA 21-1, NSE, CA 19-9, Pro-GRP and SCC. The diagnosis of each cancer patient (those with radiographically apparent pulmonary nodules) was confirmed by clinical outcome, imaging diagnosis and histological examinations. The following clinical characteristics of each participant was also collected: age at time of blood draw, gender, smoking history (current or former), pack-years, family history of lung cancer, presence of symptoms, concomitant Illnesses, and number and size of nodules.

TABLE 16

Clinical characteristic of the cancer and control subjects

|  | Cancer (502) | Control (503) |
| --- | --- | --- |
| Age | 62 | 58 |
| Sex (% Male) | 91 | 91 |
| Symptomatic/Asymptomatic (%) | 57/43 | 58/42 |
| Median Pack years | 40 | 35 |
| Current/Former smokers (%) | 89/11 | 87/13 |
| Adenocarcinoma (%) | 41 |  |
| Squamous (%) | 34 |  |
| Small Cell (%) | 18 |  |
| Large Cell (%) | 3 |  |
| Stage I (%) | 54 |  |
| Stage II (%) | 24 |  |
| Stage III (%) | 18 |  |
| Stage IV (%) | 4 |  |

The protein biomarker concentrations were determined by a microparticle enzyme immunoassay using Abbott reagent sets (Abbott, USA) and measured by a chemical luminescence analyzer (ARCHITECT i2000SR, Abbott, USA) according to manufacturer's recommendations.

Statistical Analysis

Logistic regression was used to predict the binary (yes/no) cancer patient outcome using a vector of independent variables that were continuous (e.g. biomarker concentration values) or dichotomous (e.g. current or former smoker). In the logistic model the binary (yes/no) outcome is converted to a probability function [f(p)] using the following equation:

$$f(p) = \left(\frac{p}{1-p}\right)$$

Therefore, the probability function can then be used in a predictive model including an intercept ($\alpha$), and an estimate ($\beta$) for a predictor (X).

$$f(p) = \alpha + \beta X$$

When more than one predictor is used, the model is called a multivariate logistic regression:

$$f(p) = \alpha + \beta_1 X_{i1} + \beta_2 X_{i2} + \ldots + \beta_p X_{ip}$$

Stepwise logistic regression is a special type of multivariate logistic regression where predictors are iteratively included in the model if the predictive strength of the chi-square statistic for the predictor meets a pre-determined significance threshold (alpha=0.3).

The entire data set (N=1005) was treated as a training data set for model development. The panel of 6 biomarkers (CEA, CYFRA 21-1, NSE, CA 19-9, Pro-GRP and SCC) and 7 clinical factors (smoking status, pack years, age, history of lung cancer, symptoms (e.g., symptoms and signs associated with lung cancer: coughing, coughing up blood, shortness of breath, wheezing or noisy breathing, loss of appetite, fatigue. recurring infections, etc.), nodule size and cough) were analyzed. In the analysis, symptoms with no numerical value (e.g. coughing) are assigned a binary value, 1 or 0, either the symptom is present or it isn't whereas symptoms with a numerical value, e.g. age or pack years, are used in the analysis. The MLR models developed were compared to "any marker high" approach wherein if any individual biomarker value is above its respective cut-off point, the test is considered positive. For new model development, we added clinical parameters to the biomarker panel. In embodiments, the MLR is used to calculate a probability value (also referred to herein as a composite score or predicted probabilities) for the measured values of the panel of biomarkers and clinical parameters, that probability value is then compared to a threshold value to determine whether or not the probability value is above or below the threshold value, wherein the radiographically apparent pulmonary nodules in a patient are classified as malignant, if the probability value is above the threshold value, or the radiographically apparent pulmonary nodules in a patient are classified as benign, if the probability value is below the threshold value. In embodiments, that threshold value is simply a predictive value of 50% wherein a patient with a predictive value about 50% is either classified as having malignant pulmonary nodules or is considered to have an increased likelihood for malignancy pulmonary nodules. In other embodiments, the threshold is determined based on an 80% sensitivity wherein a ROC/AUC analysis is performed based on the predictive value to determine if it is above or below a set threshold value.

A series of alternative statistical methods to predict Lung Cancer (malignant pulmonary nodules) were tested in three runs each using 80% of the sample as the training data set and 20% as a testing set. The following methods were run side by side on the model with the following clinical parameter and biomarker panels: Smoking Status, Patient Age, Nodule Size, CEA, CYFRA and NSE. In this study, that panel was the most predictive (highest AUC) for correctly distinguishing benign from malignant pulmonary nodules.

1. Logit model: simple traditional logistic regression model;
2. Random forest: this is done using Breiman's random forest algorithm for classification and regression, which could avoid overfitting the training dataset. A total of 500 decision trees to run the random forests.
3. Neural network: Use the traditional backpropagation algorithm in the model, and 2 hidden layers.
4. Support vector machine (SVM): use the default setting of R package "e1071";
5. Decision tree: use recursive partitioning and regression trees in R package "rpart";

6. Deep learning: Use the default setting of R package "h2o" which has 200 hidden layers in the neural network.

All statistical analyses were performed using SAS® v9.3 or higher.

Results

Logistic regression (univariate, multivariate and stepwise multivariate) was used to develop an algorithm for lung cancer risk prediction. Results of the logistic regression analyses performed to predict malignant pulmonary nodules are reported in Table 17:

TABLE 17

Univariate and multivariate logistic regressions predicting lung cancer (N = 1005)

| Logistic Regression Method | Model | AUC | AUC (Area Under the Curve) Lower 95 CI | Upper 95 CI | Sensitivity at 80% Specificity |
|---|---|---|---|---|---|
| Univariate | Smoking Status | 0.51 | 0.49 | 0.53 | 20.5 |
| Univariate | Pack-years | 0.59 | 0.56 | 0.63 | 26.3 |
| Univariate | Age | 0.66 | 0.63 | 0.70 | 39.1 |
| Univariate | History of LC | 0.50 | 0.49 | 0.52 | 20.1 |
| Univariate | Symptoms | 0.52 | 0.49 | 0.56 | 21.9 |
| Univariate | Nodule Size | 0.71 | 0.68 | 0.74 | 47.3 |
| Univariate | CA 19-9 | 0.58 | 0.54 | 0.62 | 31.6 |
| Univariate | CEA | 0.71 | 0.68 | 0.74 | 50.2 |
| Univariate | CYFRA | 0.77 | 0.74 | 0.79 | 59.3 |
| Univariate | NSE | 0.70 | 0.67 | 0.73 | 49.1 |
| Univariate | SCC | 0.60 | 0.57 | 0.63 | 37.2 |
| Univariate | cough | 0.56 | 0.53 | 0.59 | 27.2 |
| Univariate | Any marker high | 0.74 | 0.70 | 0.77 | 46.0 |
| Multivariate | All 6 Biomarkers | 0.84 | 0.81 | 0.87 | 70.4 |
| Multivariate | All Predictors (6 Biomarkers and 7 Clinical Factors) | 0.87 | 0.85 | 0.90 | 75.2 |
| Multivariate | 3 Biomarkers and 3 Clinical Factors | 0.88 | 0.85 | 0.89 | 76.0 |

As shown in Table 17, the combination of the biomarkers in both, "any marker high" univariate model or multivariate model using all 6 biomarkers (Smoking Status, Patient Age, Nodule Size, CEA, CYFRA and NSE), was more accurate than the individual biomarkers considered alone (AUC 0.51-0.77 vs. 0.74 and 0.84). However, the univariate "any marker high" model with an 0.74 AUC was clearly not as good a predictive model as compared to the multivariate model with all 6 biomarkers (0.84).

For a new model development, we added clinical parameters to the biomarker panel combining all 6 biomarkers (CEA, CYFRA, NSE, Pro-GRP, SCC, CA 19-9) and 7 clinical variables (Family History of lung cancer, Nodule size, Recoded Symptoms (e.g., those associated with early or late stage lung cancer such as symptoms and signs associated with lung cancer: coughing, coughing up blood, shortness of breath, wheezing or noisy breathing, loss of appetite, fatigue. recurring infections, etc.), Pack-years, Patient Age, Smoking Status, Cough). This model yielded the highest AUC of 0.87. When specificity was fixed at 80%, the sensitivity for 1) "any marker high" model, 2) model with 6 biomarkers only, and 3) the combined 6 biomarkers and 7 clinical factors model was 46.0%, 70.4% and 75.2% respectively.

Figure 17:
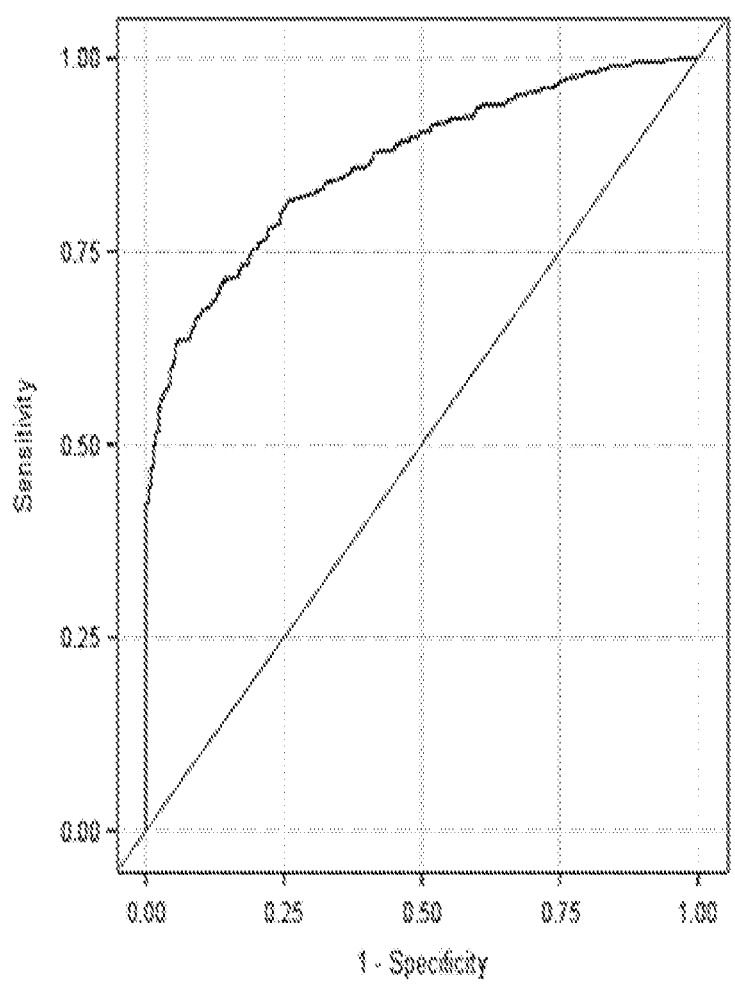
FIG. 17 shows a ROC curve analysis for discrimination of lung cancer and benign modules based on a MLR model (3 biomarkers and 3 clinical factors), in accordance with example embodiments.
Figure 18:
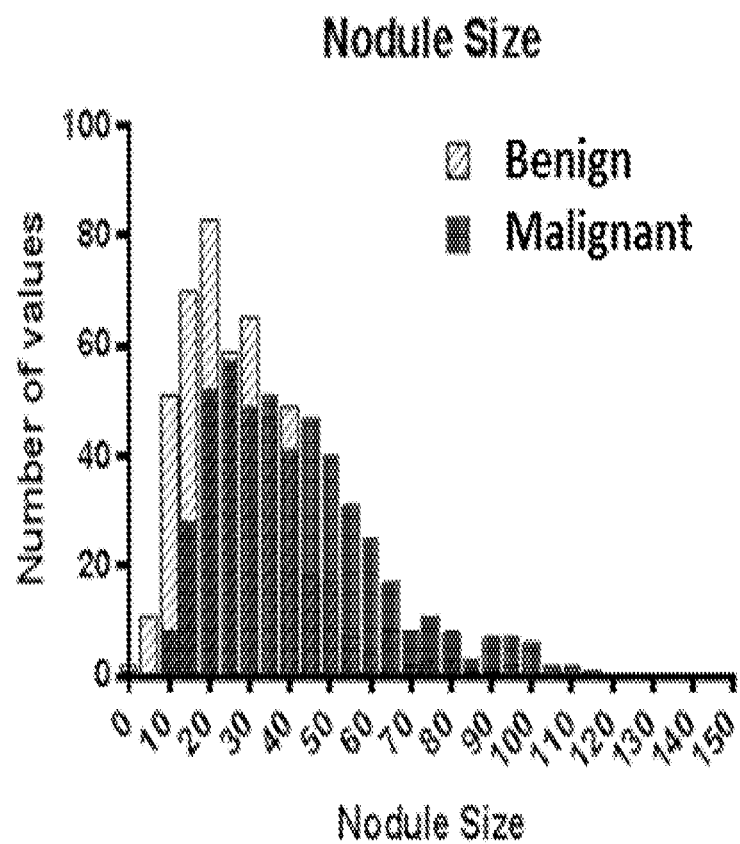
FIG. 18 shows a histogram of the nodule size in lung cancer cases and controls (benign nodules).

On the basis of both the univariate and multivariate results, the panel of six predictors (3 biomarkers and 3 clinical factors) was chosen: CEA, CYFRA, NSE, Smoking Status, Patient Age at exam, and Nodule Size. This panel of 6 predictors resulted in the best discrimination accuracy with 0.88 AUC and 76% sensitivity at 80% specificity (FIG. 17, Table 17).

The algorithm used for computing risk (i.e. probability of lung cancer) with this model was:

$$f(p) = \alpha + \beta_{SmokingStatus} X_{SmokingStatus} +$$
$$\beta_{PatientAgeAtExam} X_{PatientAgeAtExam} +$$
$$\beta_{NoduleSize} X_{NoduleSize} +$$
$$\beta_{TestValue\_CEA} X_{TestValue\_CEA} + \beta_{TestValue\_CYFRA} +$$
$$\beta_{TestValue\_NSE} X_{TestValue\_NSE}$$

Using the combined biomarker-clinical model, we performed evaluation of the test accuracy by cancer stage and histology. Table 18 shows that the test sensitivity was improved as the cancer stage increased. The most prevalent NSCLC type, adenocarcinoma and squamous cell carcinoma (SCC), demonstrated similar performance in this study (sensitivities 72% and 77%; AUC 0.85 and 0.87, respectively, p<0.0001) (Table 18). The small cell lung cancer (SCLC), a fast-growing type of cancer which represents challenges in early detection and diagnosis, was detected with 0.95 AUC and 82% sensitivity at 80% specificity.

TABLE 18

Multivariate logistic results including the variables Smoking Status, Patient Age, Nodule Size, CEA, CYFRA and NSE categorized by stage and Histological Subtype

| Sample | AUC* | | | Sensitivity at 80% Specificity | Sample |
|---|---|---|---|---|---|
| | AUC | Lower 95 CI# | Upper 95 CI | | |
| All cases and controls | 0.87 | 0.84 | 0.89 | 76.2 | cases = 502, controls = 503 |
| Stage I | 0.76 | 0.72 | 0.80 | 55.6 | cases = 180, controls = 503 |
| Stage II | 0.93 | 0.89 | 0.97 | 76.5 | cases = 51, controls = 503 |
| Stage III | 0.93 | 0.91 | 0.95 | 87.3 | cases = 158, controls = 503 |
| Stage IV | 0.97 | 0.95 | 0.99 | 92.0 | cases = 112, controls = 503 |
| Small Cell Lung Cancer | 0.95 | 0.93 | 0.98 | 82.4 | cases = 91, controls = 503 |

TABLE 18-continued

Multivariate logistic results including the variables Smoking Status, Patient Age, Nodule Size, CEA, CYFRA and NSE categorized by stage and Histological Subtype

| Sample | AUC | AUC* Lower 95 CI# | Upper 95 CI | Sensitivity at 80% Specificity | Sample |
|---|---|---|---|---|---|
| Squamous Cell Carcinoma | 0.87 | 0.84 | 0.91 | 77.2 | cases = 171, controls = 503 |
| Adenocarcinoma | 0.85 | 0.82 | 0.88 | 72.1 | cases = 208, controls = 503 |

Based on the 3 biomarkers plus 3 clinical factors model, relative risk of a patient having lung cancer (a comparison of the proportion of 'positive' outcomes in the cases vs. the controls) was calculated. A patient's measured biomarker concentrations and numerical clinical predictors (e.g. 0 or 1 for yes or no clinical parameters or a relevant number such as age, pack years, size of nodules) were multiplied by the maximum likelihood estimates from the logistic regression model. These values are then summed and multiplied by 100 to calculate a patient's probability of % risk of cancer. This could be a diagnostic tool to let doctors know the probability that their patient has lung cancer based on the model we are using. In addition, those patients with an increased risk for lung cancer can then either be screened using CT or provided with a therapeutic treatment.

Advanced Cognitive Computing Approaches Models

We also evaluated Deep learning Neural Networks (DNN) method, as well as other modelling approaches (random forest, classification and regression trees, support vector machine), using the entire data set (n=1005) (Table 19). These methods have been used to develop algorithms that combine measurements of the most predictive biomarkers and clinical parameters in a panel to achieve the highest diagnostic accuracy. The results summarized in Table 19 demonstrated that the DNN method provides better prediction accuracy in discrimination lung cancer and benign pulmonary nodules than the other methods.

TABLE 19

Comparison of results using 3 biomarkers and 3 clinical variables (Smoking Status, Patient Age, Nodule Size, CEA, CYFRA and NSE) from different modelling approaches (Random Forest, SVM, Decision tree and Deep Learning Neural Network) to predict lung cancer.

| Method | AUC* | 95% CI# | Sensitivity at 80% Specificity |
|---|---|---|---|
| Random Forest | 0.862 | 0.821-0.902 | 75 |
| SVM | 0.848 | 0.805-0.891 | 69 |
| Decision tree | 0.806 | 0.759-0.852 | 71 |
| Deep learning (DNN) | 0.890 | 0.832-0.910 | 79 |

Model cross validation: Cross validation is one important model validation technique for assessing how the results could be generalized to an independent data set. We applied repeated random sub-sampling validation, where we randomly split the dataset into training and validation set by different ratios. The results were averaged over the splits and provided in Table 19.

Relationship with Nodule Size

Further analyses of the data set from the cohort of n=1005 was focused on the relationship between nodule size and probability that a nodule is malignant.

The histogram (See FIG. 27) shows the distribution of nodule sizes for "cancer" and "control" participants in the cohort of n=1005. 535 patients in this set had nodules with 30 mm or higher in diameter. In general, the size of lung nodules was higher in patients with lung cancer (malignant nodules) than in benign nodules. The entire data set was categorized into 3 nodule sizes: 0-14, 15-29, and ≥30 mm. The univariate and then multivariate and stepwise multivariate logistic regression analyses was performed on 3 sub-samples of the n=1005 cohort data set. Based on the results, the best model combining biomarker values and clinical factors was chosen for each nodule size category. See Table 20. The MLR model for the first nodule category (below 14 mm) includes 4 biomarkers (CEA, CYFRA, NSE, Pro-GRP) and 4 clinical parameters (patient age at the time of exam, cough, smoking duration, presence of symptoms). Pro-GRP did not improve the test accuracy for nodule groups 2 and 3 and was omitted from the model.

TABLE 20

Model performance by nodule size category

| Variables in the model | Nodule size | Samples | AUC* | Lower 95% CI# | Upper 95% CI# | Sensitivity | Specificity |
|---|---|---|---|---|---|---|---|
| 4 Biomarkers (CEA, CYFRA, NSE, Pro-GRP) + 4 clinical parameters | 0-14 mm | cases = 23, controls = 54 | 0.84 | 0.73 | 0.95 | 60.9 | 88.9 |
| 3 Biomarkers (CEA, CYFRA, NSE) + 4 clinical parameters | 15-29 mm | cases = 148, controls = 193 | 0.79 | 0.75 | 0.84 | 62.8 | 77.2 |
| 3 Biomarkers (CEA, CYFRA, NSE) + 4 clinical parameters | ≥30 mm | cases = 331, controls = 204 | 0.91 | 0.89 | 0.94 | 83.7 | 81.9 |

Figure 19:
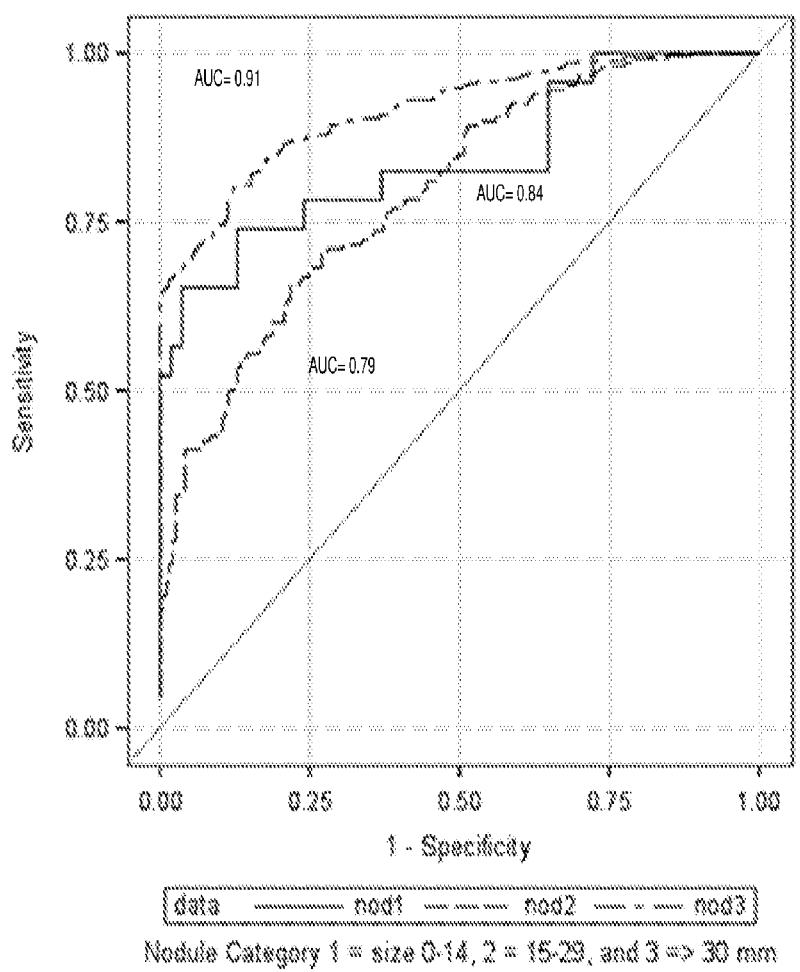
FIG. 19 shows ROC curves for each of the three nodule subgroups based on MLR models, in accordance with example embodiments.

FIG. 19 shows ROC graphs for the three nodule subgroups. As shown in Table 20 and FIG. 19, the AUC of the combined biomarker-clinical factors assessment in patients with small nodules (0-14 mm) was 0.84, with intermediate size nodules (15-29 mm) 0.79 and in those with large nodules (above 3 cm) 0.91.

The best model is a combination of 3 Biomarkers (CEA, CYFRA, NSE)+4 clinical parameters (Patient Age, Cough, and Smoking Duration)) to distinguished malignant intermediate size nodules (15-29 mm) from benign with 62.8% sensitivity and 77.2% specificity. See Table 20. The same combination of biomarkers and clinical parameters was used for the large size nodules (>30 mm) and classified the difference between benign and malignant nodules with higher sensitivity and specificity at 83.7% and 81.9%, respectively. See Table 20. For the smallest nodules (0-14 mm) the best model was 4 biomarkers (CEA, CYFRA, NSE, and Pro-GRP) and 4 clinical parameters (Symptoms, Patient Age, Cough and Smoking Duration).

Figure 20:
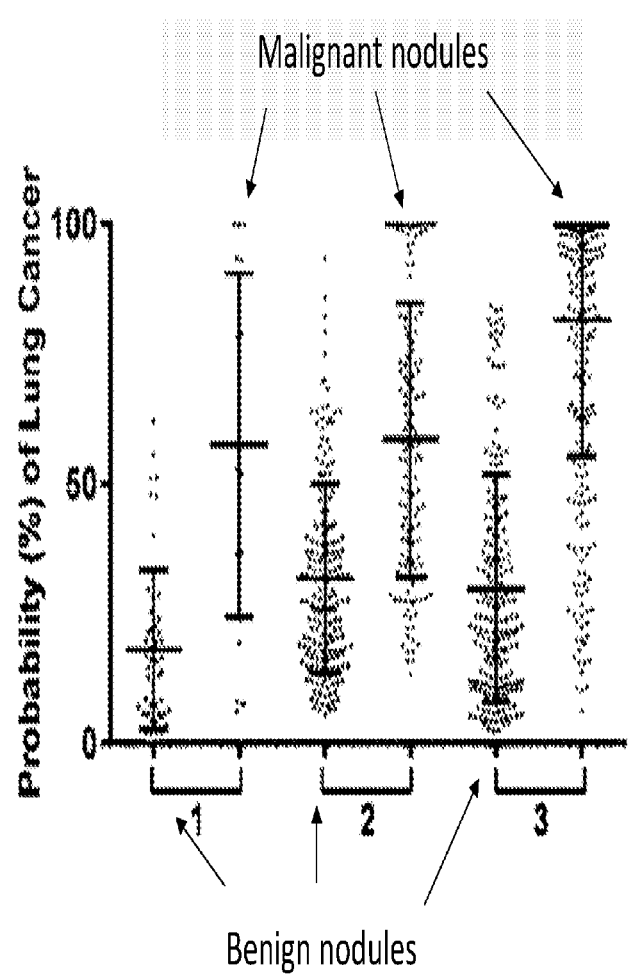
FIG. 20 shows a probability of lung cancer in accordance with example embodiments.

To calculate % probability of lung cancer in each nodule size category the maximum likelihood estimates from the MLR model were used. Scatter dot plot in FIG. 20 shows the lung cancer probability for each nodule size category.

DISCUSSION

The high sensitivity of LDCT comes at the cost of detecting many false positives, including benign pulmonary nodules. Studies indicated that radiologists have a difficult time effectively differentiating true (malignant) nodules from false positives. Moreover, the management of small lung nodules discovered on screening CT scans has become a very difficult problem. When nodules are found between 8 mm to 15-20 mm in size (Lung-RADS ver. 1.0 assessment categories 4A, 4B, and 4X), physicians face a wide array of choices and balance a complicated clinical picture. Patients categorized as Lung-RADS Category-4 (evident in about 6% of all LDCTs in the USA) present a quandary to physicians of whether to include additional LDCT, full-exposure CT with or without contrast, PET-CT, needle biopsy or resection. A blood biomarker test that can identify patients with higher-risk and alternatively, lower risk of lung cancer (with a significant gray-zone) would beneficially improve the care and cost of handling patients with lung cancer.

We now have compelling evidence that by using an algorithmic approach we can generate a risk score (increased risk of lung cancer) that is more accurate than a risk assessment obtained from any individual marker or by a "multiple cutoff" approach. In this study, we analyzed a large data set (n=1005) from a retrospective cohort of high risk patients from China and demonstrated in this training set that the accuracy of the biomarker test was significantly improved using an algorithm that integrates biomarker values and clinical factors. The overall sensitivity of the combined MLR-based biomarker-clinical model was 76% at a specificity of 80% and 0.88 AUC. This performance was significantly superior to that of the univariate "any marker high" model with an AUC of 0.74 and 46% sensitivity at 80% specificity. Sensitivity for early stage disease (I and II) in this study was approximately 66% at 80% specificity (based on 3 biomarkers plus 3 clinical factors MLR model) compared to ~90% sensitivity for late stage (III and IV). The use of deep learning neural networks method further improved the test performance resulting in the sensitivity of 77% at 80% specificity. These preliminary results showed that deep neural network provided better prediction accuracy results than the other methods.

We also established an algorithm in an intent-to-test population of patients with indeterminate single pulmonary nodules. Lung nodules that are more than 30 mm in size are presumed to be malignant and are removed by surgery. Nodules between 5-30 mm may be benign or malignant, with the likelihood of malignancy increasing with size. Therefore, the blood test that can reduce the number of false positives and to reduce the number of unnecessary biopsies would be desirable. The n=1005 cohort set included 371 patients with nodules between 15 and 29 mm. In the US, patients categorized into that group based on nodule size are followed aggressively because of the higher rate of lung cancer in patients with this size nodule (e.g., 15 to 29 mm) and because at less than 30 mm, they are not frequently sent to surgery to have the nodule removed. The present blood biomarker algorithm can identify lung cancer patients in this cohort (15-29 mm) with 63% sensitivity and 77% specificity. Almost 100 patients in the n=1005 cohort had nodules less than 15 mm in size. In the US, patients categorized into that group based on nodule size are conservatively managed. The present combined biomarker-clinical factors algorithm can identify a sub-population of patients in this group (0-14 mm nodules) that have a high risk of cancer with 61% sensitivity and 89% specificity. The use of such algorithm could potentially dictate further diagnostic and/or invasive procedures, such as a CT scan, needle biopsy or tissue resection.

In summary, this case-control study demonstrated that immunoassay marker performance can be significantly improved with the addition of clinical factors and advanced data processing (algorithms). We developed a discontinuous, multivariate model with biomarkers and clinical variables that discriminate between malignant and benign nodules.

The invention claimed is:
1. A computer implemented method configured to use a previously generated classifier, trained with a machine learning system, for use to identify a patient likely to have cancer, comprising:
  a) obtaining input parameters from the patient for the classifier comprising selecting at least two different biomarkers selected from AFP, CA125, CA 15-3, CA 19-19, CEA, CYFRA 21-1, HE-4, NSE, Pro-GRP, PSA, SCC, anti-Cyclin E2, anti-MAPKAPK3, anti-NY-ESO-1, and anti-p53 and at least one clinical parameter selected from age, gender or smoking status; and,
  b) using the classifier with the selected input parameters, wherein the classifier generates a composite algorithm value that is converted to a positive predictive score (PPS) relative to a cohort population using a set of data comprising a plurality of prospective patient records from more than 20,000 patients that assigns a risk of having cancer for the patient, wherein the PPS is divided by a reported incidence of cancer in the cohort population, wherein the classifier was trained using a set of data comprising a plurality of prospective patient records from more than 20,000 patients, each prospective patient record including a plurality of parameters and corresponding values for each patient included in the patient records, and a diagnostic indicator indicating whether or not the patient included in the patient records has been diagnosed with a specific cancer type after measurement of biomarkers, wherein at least five different cancer types are represented in the set of data.

2. The method of claim 1, wherein the patient is classified into a category indicative of a likelihood of having cancer or into another category indicative of a likelihood of not having cancer.

3. The method of claim 2, wherein the category indicative of a likelihood of having cancer is further categorized into quantitative groups.

4. The method of claim 3, wherein the quantitative groups are provided to the patient as a percentage, multiplier value, composite score or risk score for the likelihood of having cancer.

5. The method of claim 1, further comprising providing a notification to the patient recommending diagnostic testing when the patient is classified into the category indicative of a likelihood of having cancer.

6. The method of claim 5, wherein the diagnostic testing is radiographic screening.

7. The method of claim 1, wherein the biomarkers are selected from the group consisting of: CA125, CA 15-3, CA 19-19, CEA, CYFRA 21-1, Pro-GRP, PSA, and SCC.

8. The method of claim 1, wherein the biomarkers includes any three, any four, any five, or any six biomarkers.

9. The method of claim 1, wherein at least one additional clinical parameter is included and selected from the group consisting of:
   (1) number of pack years;
   (2) symptoms;
   (3) family history of cancer;
   (4) concomitant illnesses;
   (5) number of nodules;
   (6) size of nodules; and
   (7) imaging data.

10. The method of claim 1, wherein the classifier was further trained using biomarker velocity input parameters, wherein the biomarker velocity is determined by:
   (1) obtaining serial values for at least one of the at least two different biomarkers; and
   (2) determining a biomarker velocity for the at least one of the at least two different biomarkers based upon the serial values.

11. The method of claim 1, wherein the classifier is a neural net, a support vector machine, a decision tree, a random forest, a neural network, or a deep learning neural network.

12. The method of claim 11, wherein the neural net has any one or more of the following features:
   a. at least two hidden layers;
   b. at least two outputs, with a first output indicating that lung cancer is likely and a second output indicating that lung cancer is not likely; and
   c. 20-30 nodes.

13. The method of claim 1, wherein the classifier has a specificity of at least 80%.

14. The method of claim 1, wherein the classifier has a sensitivity of at least 80%.

15. The method of claim 1, wherein the cancer is selected from the group consisting of: breast cancer, bile duct cancer, bone cancer, cervical cancer, colon cancer, colorectal cancer, gallbladder cancer, kidney cancer, liver or hepatocellular cancer, lobular carcinoma, lung cancer, melanoma, ovarian cancer, pancreatic cancer, prostate cancer, skin cancer, and testicular cancer.

16. The method of claim 1, wherein the cancer is lung cancer.

* * * * *